US007015030B1

(12) United States Patent
Fouillet et al.

(10) Patent No.: US 7,015,030 B1
(45) Date of Patent: Mar. 21, 2006

(54) MICROFLUIDIC DEVICES AND USES THEREOF IN BIOCHEMICAL PROCESSES

(75) Inventors: Yves Fouillet, Voreppe (FR); Claude Vauchier, Saint-Egreve (FR); Jean-Frederic Clerc, Saint-Egreve (FR); Christine Peponnet, Tigery (FR)

(73) Assignees: Genset S.A., (FR); Commissariat a l'energie Atomique, (FR)

( * ) Notice: Subject to any disclaimer, the term of this patent is extended or adjusted under 35 U.S.C. 154(b) by 399 days.

(21) Appl. No.: 09/627,647

(22) Filed: Jul. 28, 2000

(30) Foreign Application Priority Data

Jul. 28, 1999 (FR) .................................. 99/09806
Sep. 17, 1999 (FR) .................................. 99/11652
Oct. 1, 1999 (FR) .................................. 99/12317

(51) Int. Cl.
C12M 1/34 (2006.01)
C12Q 1/68 (2006.01)
C12P 19/34 (2006.01)

(52) U.S. Cl. .................. 435/287.1; 435/6; 435/91.1
(58) Field of Classification Search .................. 435/6, 435/91.1, 91.2, 183, 287.2; 536/23.1, 24.33
See application file for complete search history.

(56) References Cited

U.S. PATENT DOCUMENTS

| 5,270,183 A | 12/1993 | Corbett et al. |
| 5,333,675 A | 8/1994 | Mullis et al. |
| 5,498,392 A * | 3/1996 | Wilding et al. ............ 422/68.1 |
| 5,508,197 A * | 4/1996 | Hansen et al. ............ 435/285.1 |
| 5,587,128 A * | 12/1996 | Wilding et al. ............ 422/50 |
| 5,589,136 A | 12/1996 | Northrup et al. |
| 5,605,662 A * | 2/1997 | Heller et al. ............ 422/68.1 |
| 5,716,825 A | 2/1998 | Hancock et al. |
| 5,716,842 A | 2/1998 | Baier et al. |
| 5,726,026 A * | 3/1998 | Wilding et al. ............ 435/7.21 |
| 5,736,314 A | 4/1998 | Hayes et al. |
| 5,736,614 A | 4/1998 | Saito et al. |
| 5,779,977 A | 7/1998 | Haff et al. |
| 5,795,976 A | 8/1998 | Oefner et al. |
| 5,858,804 A * | 1/1999 | Zanzucchi et al. .......... 436/536 |
| 5,866,345 A | 2/1999 | Wilding et al. |
| 5,872,010 A | 2/1999 | Karger et al. |
| 6,004,744 A | 12/1999 | Goelet et al. |
| 6,046,056 A * | 4/2000 | Parce et al. ................ 436/514 |
| 6,054,268 A | 4/2000 | Perlin |
| 6,054,277 A | 4/2000 | Furcht et al. |
| 6,136,212 A * | 10/2000 | Mastrangelo et al. ........ 216/49 |
| 2001/0041357 A1 | 11/2001 | Fouillet et al. |

FOREIGN PATENT DOCUMENTS

| EP | 0820432 A1 | 10/1994 |
| EP | 636 413 | 2/1995 |

(Continued)

OTHER PUBLICATIONS

Kopp et al., "Chemical Amplification: Continuous-Flow PCR on a Chip," Science, vol. 280, May 15, 1998, pp. 1046-1048.*

(Continued)

Primary Examiner—Bradley L. Sisson
(74) Attorney, Agent, or Firm—Saliwanchik, Lloyd & Saliwanchik

(57) ABSTRACT

Provided is a microfluidic device comprising a microfluidic substrate comprising at least one pathway for sample flow; and at least one thermal transfer member which is capable of cycling between at least two temperatures. The thermal transfer member is adapted to heat at least a portion of the sample pathway while a sample is flowing along said at least a portion of said sample pathway. Provided also are methods of carrying out biochemical protocols using such a device.

40 Claims, 13 Drawing Sheets

FOREIGN PATENT DOCUMENTS

| | | |
|---|---|---|
| GB | 2 325 464 | 11/1998 |
| WO | WO 93/22058 A1 | 11/1993 |
| WO | WO 96/15269 | 5/1996 |
| WO | WO 97/16561 | 5/1997 |
| WO | WO 98/22625 | 5/1998 |
| WO | WO 98/32535 | 7/1998 |
| WO | WO 98/45481 | 10/1998 |
| WO | WO 99/12016 | 3/1999 |
| WO | WO 99/17093 | 4/1999 |
| WO | WO 99/39005 | 8/1999 |
| WO | WO 99/41015 | 8/1999 |
| WO | WO 99/64848 A1 | 12/1999 |
| WO | WO 00/23190 | 4/2000 |

OTHER PUBLICATIONS

Kopp et al., "Chemical Amplificaiton: Continuous-flow PCR on a Chip," Science, vol. 280, May 15, 1998, pp. 1046-1048.*

Kopp et al. "Continuous Flow PCR on a Chip," Micro Total Analysis Systems, 1998, D.J. Harrison, A. van der Berg eds., Kluwer Academic Publishers, Dordrecht, pp. 7-10.*

Poser et al., "Chip elements for fast thermocycling," Sensors and Actuators A, vol. 62, 1997, pp. 672-675.*

Kopp et al, SCIENCE, "Chemical amplification: continuous flow PCR on a chip", vol. 280, pp1046-1048, May 15, 1998.

Woolley et al, Anal Chem, "Functional integration of PCR amplification and capillary electrophoresis in a microfabricated DNA analysis device", vol. 68, pp4081-4086, Dec. 1, 1996.

Ibrahim et al, Anal Chem, "Real-time microchip PCR for detecting single-base differences in viral and human DNA", vol. 70, pp2013-2017, May 1, 1998.

Northrup et al, Anal Chem, "A miniature analytical instrument for nucleic acids based on micromachined silicon reaction chambers", vol. 70, pp918-922, Mar. 1, 1998.

Cheng et al, Anal Biochem, "Degenerate oligonucleotide primed-polymerase chain reaction and capillary electrophoretic analysis of human DNA on microchip-based devices", vol. 257, pp101-106, 1998.

Wilding et al, Clin Chem, "PCR in a silicon microstructure", vol. 40, No. 9, pp1815-1818, 1994.

Daniel et al, Sensors and Actuators, "Silicon microchambers for DNA amplification", vol. A 71, pp81-88, 1998.

Cheng et al, Nucleic Acids Res, "Chip PCR. II. Investigation of different PCR amplification systems in microfabricated silicon-glass chips", vol. 24, No. 2, pp380-385, 1996.

Waters et al, Anal Chem, "Multiple sample PCR amplification and electrophoretic analysis on a microchip", vol. 70, pp5172-5176, Dec. 15, 1998.

Hadd et al, Anal Chem, "Microchip device for performing enzyme assays", vol. 69, pp3407-3412, Sep. 1, 1997.

Kopp et al, "Continuous flow PCR on a chip", Micro Total Analysis Systems '98, D.J.Harrison, A.van den Berg, eds., Kluwer Academic Publishers, Dordrecht, pp7-10, 1998.

Aarts, H.J., et al., "High-resolution genotyping of Salmonella strains by AFLP-fingerprinting", Lett. Appl. Microbiol. (1998), 26:131-5; PMID: 9569696.

Barany, F., "The Ligase Chaine reaction in a PCR World", PCR Methods and Applications (1991), 1:5-16; Cold Spring Harbor Laboratory Press.

Bolla, M.K., et al., "Rapid determination of apolipoprotein E genotype using a heteroduplex generator", J. Lipid Res. (1999), 40:2340-2345; PMID: 10588960.

Burns, M., et al., "An Integrated Nanoliter DNA Analysis Device", Science (1998), 282:484-487.

Chevalier, M., et al., "Substrate Binding Induces Deploymerization of the C-terminal Peptide Binding Domain of Murine GRP78/BiP", J. Biol. Chem. (1998), 273(41):26827-26835; The American Society for Biochemistry and Molecular Biology, Inc.

Goulding, J., et al., "Genome-Sequence-Based Fluorescent Amplified-Fragment Length Polymorphism Analysis of Mycobacterium tuberculosis", J. Clin. Microbiol. (2000), 38(3):1121-1126; PMID: 10699006; American Society for Microbiology.

Gzyl, A., et al., "Technical aspects of random amplified polymorphic DNA (RAPD) technique in genotyping of bacterial strains", Acta Microbiol. Pol. (1999), 48(3):243-59; PMID: 10756711.

Happ, G., et al., "DLA-DRB1 histocompatibilty genotyping using RT-nested PCR and cycle sequencing", Vet. Immunol. Immunopathol. (1999), 69:93-100; PMID: 10507296; Elsevier Science B.V.

Harwood, C., et al., "Degenerate and Nested PCR: a Highly Sensitive and Specific Method for Detection of Human Pappillomavirus Infection in Cutaneous Warts", J. Clin. Microbiol. (1999), 37(11):3545-3555; PMID: 10523550; American Society for Microbiology.

Hayashi, H., et al., "Temperature-dependent associating property of liposomes modified with a thermosensitive polymer", Bioconjug Chem (1998), 9:382-9; PMID: 9576813; American Chemical Society.

Hookey, J.V., et al., "Use of Fluorescent amplified fragment length polymorphism (fAFLP) to characterize methicillin-resistant Staphylococcus aureus", J. Microbiol. Meth. (1999), 37:7-15; Elsevier Science B.V.

Jensen, S.A., et al., "Domain 26 of tropoelastin plays a dominant role in association by coacervation", J. Biol. Chem. (2000); PMID 10862774; The American Society for Biochemistry and Molecular Biology, Inc.

Jonas, D., et al., "Comparative Evaluation of Three Different Genotyping Methods for Investigation of Nosocomial Outbreaks of Legionnaires' Disease in Hospitals", J. Clin. Microbiol. (2000), 38(6):2284-2291; PMID: 10834990; American Society for Microbiology.

Khandijan, E.W., "Heat Treatment induces dephosphorylation of pRb and dissociation of T-antigen/pRb complex during transforming infection with SV40", Oncogene (1995), 10:359-367; Stockton Press.

Kishore, N., et al., "A thermodynamic investigation of reactions catalyzed by tryptophan synthase", Biophys. Chem. (1998), 73:265-280; Elsevier Science B.V.

Kwok, P.-Y., et al., "Detection of Single Nucleotide Variations", Genetic Engineering (1998), 20:125-134; PMID: 10395459; Plenum Press, New York.

Metcalfe, P., et al., "HPA Genotyping by PCR-SSP: Report of 4 Exercises", Vox Sang. (1999), 77:40-43; PMID: 10474089; S. Karger AG, Basel, Switzerland.

Nelson, J.H., et al., "A novel and rapid PCR-based method for genotyping human papillomaviruses in clinical samples", J. Clin. Microbiol. (2000), 38(2):688-95; PMID: 10655368; American Society for Microbiology.

Poser, S., et al., "Chip elements for fast thermocycling", Sensors and Actuators (1997), A 62:672-675; Elsevier Science S.A.

Romppanen, E.L., et al., "Molecular diagnosis of medium-chain acyl-CoA dehydrogenase deficiency by oligonucleotide ligation assay", Clin. Chem. (1998), 44(1):68-71; PMID 9550560.

Ruano, M.L., et al., "Self-aggregation of surfactant protein A", *Biochemistry* (2000), 39:6529-37; PMID: 10828969; American Chemical Society.

Sauer, S., et al., "A novel procedure for efficient genotyping of single nucleotide polymorphisms", *Nucleic Acids Research* (2000), 28(5):e13-e13; Oxford University Press.

Sijbesma, R.P., et al., "Reversible Polymers Formed from Self-Complementary Monomers Using Quadruple Hydrogen Bonding", *Science* (1997), 278(5343):1601-1604; American Association for the Advancement of Science.

Sohda, T., "Allele-specific polymerase chain reaction for genotyping human cytochrome P450 2E1", *J. Clin. Lab Anal.* (1999), 13:205-8; PMID 1094127.

Speijer, H., et al., "Application of different genotyping methods for *Pseudomonas aeruginosa* in a setting of endemicity in an intensive care unit", *J. Clin. Microbiol.* (1999), 37(11):3654-61; PMID:10523569; American Society for Microbiology.

Walker, G.T., et al., "Strand Displacement Amplification—an Isothermal, in vitro DNA Amplification Technique", *Nucleic Acids Res.* (1992), 20(7):1691-1696; Oxford University Press.

Winzeler, E., et al., "Functional Characterization of the *S. cerevisiae* Genome by Gene Deletion and Parallel Analysis", *Science* (1999), 285(5429):901-906.

* cited by examiner

MICROFLUIDIC DEVICES AND USES THEREOF IN BIOCHEMICAL PROCESSES

RELATED APPLICATIONS

The present application claims priority to French patent application serial No. 99/09806, filed 28 Jul. 1999; French patent application serial No. 99/11652 filed 17 Sep. 1999; and French patent application serial No. 99/12317 filed Oct. 1, 1999 the disclosures of all of which are incorporated herein by reference in their entireties.

BACKGROUND

Microfluidics consist of using microchannels instead of test tubes or microplates to carry out analyses and reactions. These microchannels or microcircuits are etched into silicon, quartz, glass, ceramics or plastic. The size of these channels is on the order of micrometers, while the reaction volumes are on the order of nanoliters or microliters. The principle of a microfluidic device is to guide reaction media containing reagents and samples, over zones which correspond to the different steps of the protocol. The integration of reactors, chromatographic columns, capillary electrophoresis systems and miniature detection systems into these microfluidic systems allows the automation of complex protocols by integrating them into a single-system. These "laboratories on chips" have made it possible to obtain results which are efficient in terms of reaction speed, in terms of product economy and in terms of miniaturization which allows the development of portable devices. Complex protocols have been integrated and automated, including biochemical or molecular biology protocols which often require extensive manipulation. These manipulations include mixing reagents and samples, controlling the reaction temperature, carrying out thermal cycling, separation by electrophoresis, and detection of reaction products.

Wolley et al. (*Anal. Chem.* 68: 4081–4086 (1996), the contents of which is incorporated herein by reference in its entirety) discloses the integration of a PCR microreactor, a capillary electrophoresis system and a detector in a single device. The PCR reaction, separation of PCR products by electrophoresis, and detection of PCR products are carried out automatically. This device does not, however, integrate the mixing of reagents, and it does not allow large scale protocols to be performed.

A device or substrate allowing integration of the steps of reagent mixing and enzymatic reaction has been described by Hadd et al. (*Anal. Chem.* 69, 3407–3412, (1997), the contents of which is incorporated herein by reference in its entirety). This device provides a microcircuit of channels and reservoirs etched into a glass substrate. The moving and mixing of the fluids takes place by electrokinetics.

Microfluidic systems for the integration of protocols and of analyses have been described in international patent application WO 98/45481. One of the difficulties in implementing these devices resides in the movement of the fluids. The fluids are generally moved by electroosmosis or by electrokinetics, which requires a network of electrodes. Other systems use micropumps and microvalves which are integrated in the microfluidic substrate. In the majority of cases the reactions are carried out while stationary in a microreactor and then the fluids are thus moved from one reactor to another at each step of the protocol. These systems which integrate electrodes, microvalves or micropumps are very costly and their complexity does not allow large scale applications for simultaneously treating a very large number of samples. One of the major difficulties is the distribution, mixing and transport of a very large number of products in parallel or in series.

Thus, there exists a need to develop a device comprising a microfluidic substrate allowing the manipulation of a large number of fluids and/or allowing a large number of complex protocols, particularly protocols involving temperature treatment, to be carried out at a low cost.

SUMMARY OF THE INVENTION

The present invention provides a device comprising a microfluidic substrate which comprises at least one microchannel in which reactions or sequences of reactions, which make up a protocol, are carried out.

The present invention provides a microfluidic substrate which comprises at least one microchannel in which reactions or sequences of reactions, which make up a protocol, are carried out, where the channel is fed in continuous flow.

Combining the microfluidic substrate with a thermal support makes it possible to control the reaction temperature in the different zones of the channel corresponding to the various steps of the protocol. The invention relates to advantageous devices and processes for carrying out thermal cycling in continuous flow on thermal cycling zones.

The device is based on a system for distributing and moving the fluids by hydrostatic pressure. All steps of a protocol are carried out in continuous flow; wherein sequential injections of samples and of reagents make it possible to carry out a large number of reactions one after the other in the same channel. Reagents can be injected successively at different stages of the protocol. By arranging several channels in parallel, it is possible to carry out the same protocol in series in the same channel and in parallel in various channels. Synchronizing the reactions in the channels arranged in parallel makes it possible to distribute the reagents simultaneously into the various channels. This arrangement has a particularly advantageous application in improving the throughput and reducing the number of distributions to be carried out.

The microfluidic substrate of the present invention is preferably semi-disposable (used for a few hundred reactions or some tens of hours) and is added on, in a removable fashion, to the thermal support, the fluid feed devices and the detection means. The control of the temperature, the movement of the fluids, the injection of the reagents, the mixing of the solutions in continuous flow and the detection are entirely automated. In addition, the combination of a permanent device and a disposable but relatively inexpensive microfluidic substrate allows a considerable reduction in costs relative to systems in which everything is integrated on the same microfluidic device.

One embodiment of the present invention is a device comprising a microfluidic substrate comprising at least one pathway for sample flow and at least one thermal transfer member which is capable of cycling between at least two temperatures, said at least one thermal transfer member being adapted to bring at least a portion of said sample pathway to said at least two temperatures while a sample is continuously flowing along said at least a portion of said sample pathway. In some aspects of this embodiment, the device further comprises a force supplying member operably linked to said at least one pathway for sample flow wherein said force supplying member applies a force to said sample such that said sample travels along said at least one pathway. The device may further comprise a sample supplier which supplies a sample to said at least one pathway. The device may also further comprise at least one inlet basin positioned at a first end of said at least one pathway such that said sample supplier supplies said sample to said inlet basin and said sample travels from said inlet basin to said at least one pathway. The device of may also further comprise at least one outlet basin positioned at a second end of said pathway. In some aspects of the present invention, the device further comprises at least one reagent supplier positioned between said inlet basin and said outlet basin. In other aspects of the present invention, the device comprises a plurality of said pathways. The pathways may comprise channels arranged in parallel. The force generated by said force supplying member may be pressure. The microfluidic substrate may consist essentially of silicon. The device may further comprise a detector for measuring a physicochemical property of said biological sample. The thermal transfer member may comprise a metal bar in fluid communication with a plurality of water sources containing water at said at least two temperatures, said metal bar being in thermal communication with said at least a portion of said sample pathway.

Another embodiment of the present invention is a method for conducting a biochemical or chemical process comprising cycling at least a portion of at least one sample flow pathway between at least two temperatures while a sample comprising the reagents for said biochemical or chemical process is flowing through said at least a portion of said at least one sample flow pathway. The sample flow pathway may be located on a microfluidic substrate. The sample flow pathway may be in thermal communication with at least one thermal transfer member which cycles between said at least two temperatures while said sample is continuously flowing through said at least a portion of said at least one sample flow pathway. The thermal transfer member may cycle through said at least two temperatures a plurality of times while said sample is continuously flowing through said at least a portion of said at least one sample flow pathway. The thermal transfer member may cycle through said at least two temperatures from about 2 to about 35 times while said sample is continuously flowing through said at least a portion of said at least one sample flow pathway. In some aspects of this embodiment, at least a portion of a plurality of sample flow pathways are simultaneously cycled between said at least two temperatures while a plurality of samples are simultaneously flowing through said sample flow pathways. The biochemical or chemical reaction may comprise a nucleic acid amplification procedure.

The nucleic acid amplification procedure may comprise polymerase chain reaction. The method may further comprise determining the identity of at least one polymorphic nucleotide in the product of said nucleic acid amplification procedure.

Another embodiment of the present invention is a process for carrying out biochemical protocols on at least one sample, comprising feeding at least one channel with a continuous flow of a solution containing at least one sample, injecting at least one reagent from a reagent reservoir into said channel, thereby mixing said sample and said reagent, and transferring heat between at least one thermal support and at least one temperature regulated portion of said at least one channel. The feeding step may comprise applying a pressure difference between a feed basin of said at least one channel and an outlet basin of said at least one channel. The process may further comprise detecting at least one physicochemical parameter of said sample in said at least one channel. In some aspects of the process, a temperature of said solution is adjusted to a predetermined level when said solution runs through said at least one temperature regulated portion of said at least one channel. The process may further comprise cycling said at least one thermal support through at least two different temperatures. The cycling may be repeated 1 to 35 times while solution is running through said at least one portion of said at least one channel. In other aspects of the process, a plurality of samples separated by separators are sequentially introduced into said at least one channel. In some aspects of the process, said feeding, said injecting, and said transferring are carried out simultaneously on a plurality of channels arranged in parallel.

Another embodiment of the present invention is a process for carrying out in continuous flow at least one temperature cycle on a solution containing at least one sample comprising feeding at least one channel with a continuous flow of said solution, running said solution through at least one temperature regulated zone, and cycling said at least one temperature regulated zone successively through a temperature cycle of at least two temperatures in a predetermined temporal series, such that the solution undergoes said temperature cycle at least once in running through the at least one temperature regulated zone once. The process may further comprise detecting at least one physicochemical parameter of said sample in said channel. The feeding may comprise applying a pressure difference between a feed basin of said at least one channel and an outlet basin of said at least one channel. The feeding may be sequentially repeated with a plurality of samples separated by separators. In some aspects of the process, said feeding, said running and said cycling are carried out simultaneously on a plurality of channels arranged in parallel.

Another embodiment of the present invention is a process for amplifying nucleic acids, comprising: a) mixing at least one sample comprising said nucleic acids with reagents which are suitable for amplifying nucleic acids to form at least one reaction mixture, b) feeding at least one channel with a continuous flow of said at least one reaction mixture, c) running said at least one reaction mixture through at least one temperature regulated zone, and d) cycling said temperature regulated zone through a temperature cycle of at least two temperatures in a predetermined temporal series, wherein the at least two temperatures, a duration of the temperature cycle, and a rate of said running are preselected such that said at least one nucleic acid sample undergoes a denaturation-hybridization-elongation cycle one or more times while flowing through said at least one temperature regulated zone. The feeding may comprise applying a pressure difference between a feed basin of said at least one channel and an outlet basin of said at least one channel. The channel may be formed in a microfluidic substrate. The microfluidic substrate may consist essentially of silicon. In some aspects of the process, said feeding is sequentially repeated with a plurality of nucleic acid samples separated by separators. In other aspects of the process, steps a), b), c) and d) are carried out simultaneously on a plurality of channels arranged in parallel.

Another embodiment of the present invention is a process for identifying in continuous flow at least one nucleotide in at least one target nucleic acid, comprising: a) feeding a channel with a continuous flow of a solution comprising said at least one target nucleic acid, b) injecting a microsequencing reagent comprising a microsequencing buffer, at least one microsequencing primer, at least one ddNTP and a polymerase into said channel, thereby mixing said nucleic acid solution and said reagent, c) running the solution through at least one temperature regulated zone in such a way as to produce at least one cycle comprising denaturation of said at least one target nucleic acid, hybridization of said nucleic acid with said at least one microsequencing primer, and incorporation of a ddNTP which is complementary to the nucleotide to be identified at a 3' end of said primer, and d) identifying the nucleotide which has been incorporated at the 3' end of the microsequencing primer. The feeding may comprise applying a pressure difference between a feed basin of said channel and an outlet basin of said channel. The process may further comprise amplifying said at least one target nucleic acid using the method above prior to performing said method for identifying at least one nucleotide. The ddNTPs may be labelled with fluorophores and the fluorescence of the incorporated ddNTP may be detected. The feeding, said injecting and said running may be carried out simultaneously on a plurality of channels arranged in parallel.

Another embodiment of the present invention is a process for detecting in continuous flow at least one nucleotide in at least one target nucleic acid, comprising: a) feeding a channel with a continuous flow of a solution containing at least one target nucleic acid, b) injecting the reagent for amplifying a region of the at least one target nucleic acid which carries at least one nucleotide to be detected into said channel from a first reagent reservoir, c) running the solution through at least one temperature regulated zone in such a way that the nucleic acid undergoes a denaturation-hybridization-elongation cycle one or more times, d) injecting the reagent for purifying the amplification product into said channel from a second reagent reservoir, e) running the solution through at least one temperature regulated zone to carry out a purification reaction, f) injecting the microsequencing reagent comprising the microsequencing buffer, at least one microsequencing primer, at least one ddNTP and a polymerase into said channel from a third reagent reservoir, g) running the reaction mixture through at least one temperature regulated zone in such a way as to produce at least one cycle comprising the denaturation of the target nucleic acid, the hybridization of said nucleic acid with the at least one microsequencing primer, and the incorporation of the ddNTP which is complementary to the nucleotide to be detected, at the 3' end of said primer, and h) detecting at least one ddNTP which is incorporated at the 3' end of the microsequencing primer. The feeding may comprise applying a pressure difference between a feed basin of said channel and an outlet basin of said channel. In some aspects of the process, in steps c) and e), the temperature regulated zone is brought successively to at least two temperatures in a temporal series which forms at least one cycle. The ddNTPs may be labelled with fluorophores, and wherein in step h) the fluoresence of the incorporated ddNTP is detected. The reagent for the purification may comprise an exonuclease and an alkaline phosphatase. In some aspects of the process, steps a), b), c), d), e), f), g) and h) are carried out simultaneously on a plurality of channels arranged in parallel.

DETAILED DESCRIPTION OF THE INVENTION

Figure 1:
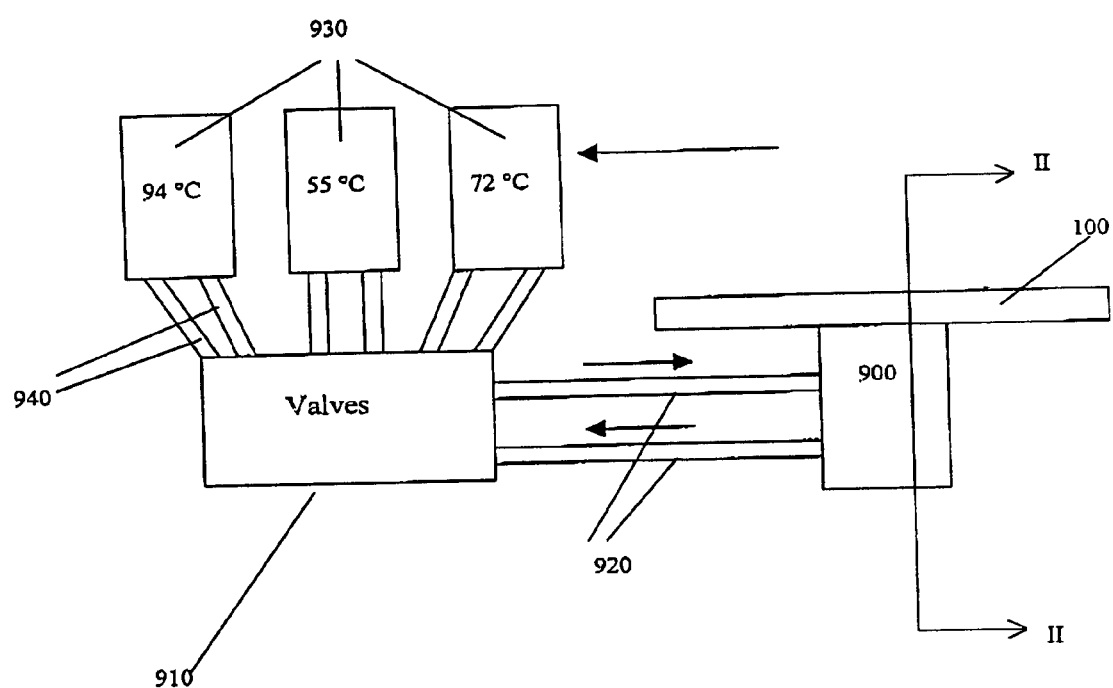
FIG. 1 is a schematic view of one embodiment of the invention.

The present invention relates to a device comprising a microfluidic substrate comprising at least one pathway for sample flow and at least one thermal transfer member which is capable of cycling between at least two temperatures. The thermal transfer member is adapted to heat or cool at least a portion of the at least one sample pathway to at least two temperatures while a sample is continuously flowing along a portion of the sample pathway. The thermal transfer member may heat or cool at least a portion of the at least one sample pathway to any desired temperature, including ambient temperature. In some embodiments, the pathway may be a channel. In various embodiments, the chemical, biochemical, and biological analysis device according to the invention comprises a microfluidic substrate comprising at least one channel which has a feed basin for injecting a sample and an outlet basin for collecting said sample, and means for feeding said channel in continuous flow. "Feed basin" and "outlet basin" are intended to mean any type of reservoir, connector or orifice at the inlet and at the outlet of the channel. As used herein, "biochemical" refers to reactions, processes, and protocols that employ at least one substrate and at least one enzyme. For example, the term "biochemical" can be used to refer to, but is not limited to protocols related to nucleic acid amplification such as the polymerase chain reaction (PCR), to genotyping such as microsequencing, or to the sequencing of nucleic acids. The term "biochemical" also includes other reactions catalyzed by an enzyme. As used herein, "chemical" refers to chemical reactions, processes, or protocols that, in at least one step, do not employ enzymatic catalysis. For example, the term "chemical" can be used to refer to organic or inorganic molecular syntheses or degradation reactions having at least one step which does not involve enzymatic activity. As used herein, "biological" refers to reactions, processes, or protocols that may comprise living material. For example, the term "biological" can be used to refer to processes including, but not limited to, a single cell, a culture of single cells, a mass of adherent cells, an organism comprised of a single cell or multiple cells, or portions of tissues or organs. The term "biological" as used herein encompasses eukaryotes, including single-celled or multicellular organisms, as well as prokaryotes, including bacteria, or viruses.

The term "microfluidic substrate" refers to a solid support in which sample pathways (such as channels), basins or reservoirs are micromanufactured. Typically, the solid support can comprise, consist essentially of, or consist of silicon glass or quartz or a plastic. The solid support can be made of a polymer material such as polymethyl methacrylate (PPMA), polycarbonate, polytetrafluoroethylene (Teflon™), polyvinyl chloride (PVC), polydimethylsiloxane (PDMS) or polysulphone. The term "microfluidic device", as used herein, refers to a device comprising a microfluidic substrate.

According to an advantageous embodiment of the invention, the microfluidic substrate is made of silicon. The techniques of micromanufacture and of etching of silicon are well known moreover, thus allowing the manufacture of channels with well defined dimensions and geometries. These techniques for machining the silicon substrate comprise in particular chemical etching techniques. Typically, microfluidic devices employ an integrated channel network fabricated into the surface of a planar substrate. A second substrate, which may or may not have complementary channels formed therein, is overlaid on the surface of the first to cover and seal the channels, thereby defining the channels.

Silicon also has advantages due to its thermal properties. Silicon is a very good heat conductor with a thermal conductivity of 150 W/mK. The high thermal conductivity allows fast temperature changes of a microfluidic substrate. By contrast, plastics are in general approximately 100 to 300 times less heat conductive than silicon. Glass and quartz are good heat conductors but are more difficult than silicon to etch with high precision. Thus, silicon is generally preferred to plastic due to its rapid response time upon contact with a heat source, and to glass and quartz due to ease of manufacturing. However, it will be appreciated that materials other than silicon may be employed.

While silicon is presented as an advantageous substrate material, substrate materials can be chosen from a wide range of suitable materials. In addition, the microfluidics substrate can be comprised of more than one zone, such that more than one type of material is used in the microfluidic susbtrate. In one embodiment, the microfluidic substrate is comprised of a first material, and a thermal zone of the microfluidic substrate is comprised of a second material. For example, a microfluidics substrate may be comprised of a material (eg. a plastic) that has lower thermal conductivity than a second material used in a thermal zone (eg. silicon). In this manner, heat exchange can be increased in temperature regulated zones and/or isolating zones can be formed between temperature regulated zones.

Substrate materials can be selected according to any desired criteria, depending on the application of the microfluidic device. In general, substrate materials can be selected according to their thermal and physicochemical properties.

As described further herein, thermal conductivity is an important characteristic of materials used for temperature regulated zones, for cycling temperature or constant temperature zones. A high thermal conductivity is particularly desirable for temperature regulated zones which must have short transition times between temperatures. Thermal conductivity is also important for the materials used to connect temperature regulated zones, or materials in which channels are disposed when not disposed in a temperature regulated zone, which should preferably be good thermal isolators, thereby decreasing the distance required between temperature regulated zones.

Materials used in the microfluidic substrate can also be selected based on thermal dilation and/or retraction upon heating or cooling. Particularly when two or more zones comprising a different type of material are used in a microfluidic substrate, the materials can be selected such that the coefficients of expansion upon heating are similar for the materials.

In addition to thermal properties, materials are also selected based on physicochemical properties. In particular, substrate materials are chosen such that they are biocompatible for a particular application of the substrate. Biocompatibility typically refers to the tendency of a material to interfere or affect a reaction or operation carried out in the microfluidic susbtrate. Interference with a reaction or operation generally involves the adsorption of reagents or dissolution of inhibitors of a reaction, such as the dissolution of metal ions that inhibit biological reactions. Due to the high surface-to-volume ratios of channels in microfluidic substrate, biocompatibility properties of the surface materials are an important aspect of substrate materials. Similarly, the total surface area relative to the reagent concentration can also be taken into account; for example, a material of lower biocompatibility having a relatively small total surface area will not be expected to significantly affect the total reagent concentration (due to adsorption phenomena) and may thus still be selected for use in a microfluidic substrate.

In further embodiments, a microfluidic susbtrate surface may be treated such that a desirable surface biocompatibility is achieved. In one example, the microfluidic substrate surface (eg. channel surface) is siliconized, as described further herein.

In another aspect, selection of a microfluidic substrate material may take into account surface wetting properties of a material. When using aqueous solutions in channels, biocompatible surfaces which are typically non-polar are suitable for use as microfluidics substrate materials. In other embodiments, when a microfluidic device is built from more than one material, the materials should be selected in such a way that they are mechanically resistant, for the application of interest, biocompatible and with similar polarities, thus a biological solution wets them similarly.

Additionally, substrate materials may be selected such that they are non-porous, thus avoiding materials favoring the formation of air bubbles in the channels and increased adsorption of reagents onto surface.

According to a particularly advantageous embodiment of the invention, the microfluidic substrate comprises a plurality of channels arranged in parallel, each feed basin being respectively connected to an outlet basin by means of the channel. Typically, several hundreds of channels are arranged in parallel on the same microfluidic substrate. A given protocol can thus be carried out in parallel in each of the channels. It is also possible to carry out different protocols in each of the channels. However, to facilitate in particular the automation of the injection of the reagents, it is more advantageous to carry out the same protocol in all the channels.

While the substrate is typically a channel disposed in a planar support, other embodiments of the substrate include, for example, capillary channels disposed in thin supports, such as the tubular capillaries having a thin substrate layer, where the capillaries can be free or physically linked in parallel. A wide range of formats for use of the capillaries with a thermal support may be used; for example, freestanding capillaries can be positioned around a thermal support capable of bringing a solution in the capillary to at least 2 different temperatures.

The device according to the invention comprises a force supplying member which supplies a force which moves the sample through the channels. Preferably, the device comprises components for feeding at least one channel in continuous flow. Various methods have been described for moving fluids in microfluidic substrates. Electrokinetic-based techniques such as electroosmosis and electrophoresis are also very widely used in microfluidics. In a preferred embodiment of the invention, the components for feeding said channels in continuous flow involve generating a pressure difference between the feed basin and the outlet basin. Preferably, this pressure difference is created by injecting volumes of fluid into a channel, the displacement of fluid allowing precise control of the flow rates. The pressure-imposed flow rate is independent of the composition of the fluids, whereas in the case of electrokinetic pumping, all the factors influencing the zeta potential (e.g. the salt concentration, the solution pH, the viscosity of the solution in the close proximity of the microfluidic device surface, adsorption of impurities on surfaces, etc.) have an effect on the flow rate and complicate the control of the flow rates. Importantly, the adsorption of impurities on the surface is difficult to control rendering the electrokinetic approach less reliable and/or more complex to control. Using pressure also makes it possible to use channels of variable geometry. In addition, the control of the fluids by pressure is not based on a complex system of electrodes, unlike electrophoresis and electroosmosis. In the device according to the invention, all the components used for injecting the fluids into the microfluidic substrate and for controlling the flow rate of the fluids are, preferably, independent of the microfluidic substrate and added on to it in a removable manner.

The device also includes a sample supplier which supplies samples to the channels. In an advantageous embodiment of the invention, the flow rate and the injection of fluids in the plurality of channels arranged in parallel are synchronized. This synchronization facilitates the automation and the integration of the various steps of the protocol. For example, the reagents can thus be injected simultaneously into all the channels.

In a particularly advantageous embodiment, the channels are fed in series with samples which are separated from each other by "separators". This "separator" which separates two samples can consist of a buffer solution or of reagents which contain(s) no sample; preferably this "separator" consists of a non-miscible inert fluid. A multitude of reactions in series (or sequential reactions) can thus be carried out "one after the other" in the same channel of the microfluidic substrate. As an example, the number of samples injected in series into the channel is between 1 and 1000, or mor preferably 1 and 100. The device according to the invention thus makes it possible to carry out large scale protocols on a large number of samples, since the samples are treated both in parallel and in series. Any suitable protocol can thus be carried out in large scale, including but not limited to biochemical reactions such as nucleic acid amplification or various genotpying, sequencing or enzymatic reaction protocols.

Generally, the injection of the samples and of the reagents into the microfluidic substrate and the movement of the fluids in continuous flow are obtained either by applying a positive pressure at the inlet or by applying a negative pressure at the outlet. Any device which allows such a pressure to be applied can be used; moreover, such devices are known.

In some embodiments, the supplying of the samples to be analysed and the placing of the reagents in the reservoirs can take place by micropipetting.

In a particular embodiment of the invention the injections of fluid into the microfluidic substrate are carried out by pneumatic injection. The samples or reagents are placed in reservoirs connected to at least one channel. The injection into the channels is performed by application of a pressure from a gas or from an incompressible liquid onto the reservoir. Such a pneumatic injection system can be used to impose a precise flow rate on all the channels.

In another embodiment of the invention syringe-driver systems arranged in parallel make it possible to regulate the flow rates in the channels. These syringe drivers can be positioned either at the inlet or at the outlet of the channel, or at both the inlet and the outlet of the channel.

In certain embodiments, it is desirable to apply pressure at both the inlet and the outlet ends of the channel. For example, one syringe driver may be used to push at the inlet end and another driver may be used to suck at the outlet end of the channel at the same flow rate as that realized by the input driver. This prevents the expansion of air bubbles formed in a channel during a reaction that could disrupt the flow of fluid in the channel. A thorough degassing of the reagents prior to injection is important in biochemical reactions such as those involving thermal cycling in which significant levels of gas are produced at high temperatures.

Optionally, fluid supply is carried out using injection device as described in French patent application No. 99 11889, filed 23 Sep., 1999, the disclosure of which is incorporated herein by reference in its entirety. An example of a suitable injection device may for example comprise a layer or set of flexible capillaries, each of which can contain or store a fluid to be injected into a channel. The capillaries are thus open at one end, which can be linked to an opening in a channel of a microfluidic device. A means for pressuring the capillaries, such as by pressing the flexible capillaries, can be used to move the fluids toward the open end of the capillary and into the channel.

In some embodiments, the fluid supply to the microfluidic substrate can be provided by a combination of the methods described above. For microfluidic substrates with a large number of channels, the fluid supply can be automated by means of a robot for high resolution distribution or dispensing. Moreover, the injections in series, or sequential injections, which assume the replacement in time of at least one solution with another, can be automated by sequentially introducing into the corresponding reservoir several different solutions. A non-miscible neutral buffer can be introduced into the reservoir between two solutions.

The precise control of the reaction temperature is an important element in carrying out chemical, biochemical and biological protocols.

In a preferred embodiment of the invention, the microfluidic device comprises at least one thermal support which has a heat exchange face which is in contact with at least one face of the microfluidic substrate such that the sample running through the channel is brought to a given temperature. In an advantageous embodiment of the invention the microfluidic substrate is placed in contact with the thermal support in a removable fashion. When carrying out complex protocols, it is often valuable to carry out various steps or reactions at different predetermined temperatures. Controlling the reaction temperature is particularly important for enzymatic reactions which must be performed at specific temperatures. The device according to the invention makes it possible to carry out protocols which comprise various steps at various fixed temperatures, as well as protocols which comprise thermal cycling steps. The capacity for performing such temperature cycles is particularly valuable for nucleic acid amplification reactions.

In one aspect, the heat exchange face of the thermal support is in contact with a face of the microfluidic substrate in the vicinity of the channels.

The dimensions of the face of the microfluidic substrate which is in contact with the thermal support can also be varied depending on the properties of the substrate and substrate materials. While most heat-conductive substrate materials will typically not require such modifications, the face of the microfluidics substrate, for example, may have a thin wall (eg. thinner than a wall separating the channels mutually or from the reservoirs) facilitating heat exchange with the thermal support.

The thermal support comprises at least one temperature regulated zone, but it can also comprise several temperature regulated zones which are brought to different temperatures. For example, the temperature regulated zones may be in thermal communication with a thermal transfer member. The thermal transfer member may be comprise a heat source, a cooling source, or both a heat source and a cooling source or may comprise a material adapted to transfer heat or cold from a heat or cooling source to the temperature regulated zones. The thermal transfer member may cycle between two or more temperatures while the sample is flowing through the temperature regulated zones.

The various temperature regulated zones are arranged in such a way as to coincide with portions of channels of the microfluidic substrate. These temperature regulated zones define zones in which a specific step of the protocol is carried out. The temperature regulated zones may be positioned at any location with respect to the microfluidic substrate such that the temperature in the microfluidic substrate can be regulated to facilitate a desired protocol. In some embodiments, the temperature regulated zones coincide for example with at least one zone of the microfluidic substrate, which is situated downstream of a connector between a reagent reservoir and a channel. By combining for example a temperature regulated zone of the thermal support with a corresponding zone of the microfluidic substrate, for example downstream of each reagent reservoir, it is possible to selectively control and adapt the temperature of the reaction mixture circulating in the channel as a function of each reagent used and as a function of the reaction performed. The term "downstream" used here is understood to be relative to the direction of outflow of the samples from the feed basin to the outlet basin. In one embodiment of the invention the thermal support comprises at least two temperature regulated zones at different temperatures, constructed such that the sample running through the channel is brought successively to at least two predetermined temperatures. The temperature can be regulated by using various temperature regulated zones at constant temperature or by varying the temperature of the temperature regulated zone. The reaction mixture running through the channel is thus brought successively to the various temperatures required.

According to the invention, a device is also provided, comprising at least one temperature regulated zone which is brought to at least two different temperatures such that the sample running through this zone once is brought to at least two predetermined temperatures. Alternatively, the device according to the invention comprises at least one temperature regulated zone which is brought to at least two different temperatures following a temporal series which forms a predetermined cycle, such that the sample undergoes the temperature cycle at least once in running through the temperature regulated zone once. In some embodiments, the sample may go through a plurality of temperature cycles as it travels through the temperature regulated zone. Preferably, the portion of the channel which crosses the temperature regulated zone is rectilinear.

Various systems can be envisaged for the thermal support and the temperature regulated zones. In a first embodiment of the invention Peltier-effect elements are used for the thermal support. Such Peltier-effect elements are familiar to those skilled in the art. Junctions of different metals, which are crossed by an electric current, make it possible to cool or heat a small surface. A temperature probe on the Peltier element makes it possible to regulate the power, which is proportional to the electrical intensity, and thus makes it possible to regulate the temperature. Alternatively or additionally, the thermal support can also comprise one or more channels which are crossed by a heat-conveying fluid. This fluid can be used to locally heat or cool the analysis support.

Preferably, the means for heating as well as the means for injecting and for controlling fluids are not integrated into the microfluidic substrate. In such embodiments, the microfluidic substrate is added onto these elements for heating and injecting fluids, in a removable fashion. This property consequently makes it possible to considerably reduce the cost of the microfluidic substrate. Thus, this support can be of the single use or multiple use type, i.e. it can be discarded after one or several uses. "Use" is intended to mean the execution of a large scale protocol in series or in parallel on the channels of the microfluidic substrate on a large amount of samples or tests but also for a single sample on one test for diagnostic use.

In a particularly advantageous aspect of the invention, the device in accordance with the invention comprises detection means for measuring a physicochemical or biological property of the samples running through the channels. In one embodiment these detection means can be located in the outlet basins of said channels. In another embodiment, the detection means are located directly in the channels or at the exit of the channel, in a second microfluidic device. Preferably, the detection is carried out in continuous flow.

Advantageously, the injection of the samples, the addition of reagents, the mixing of the solutions, the regulation of the reaction temperature and the detection can be automated in the device according to the invention. The device according to the invention is thus a totally integrated system in which manual interventions are reduced. Various protocols can thus be totally integrated in the continuous flow device according to the invention.

The invention also relates to the integration of complex protocols in a continuous flow microfluidic device and to the carrying out of protocols in continuous flow.

According to one embodiment of the invention, a process is provided for carrying out chemical, biological or biochemical protocols on at least one sample, which comprises the following steps:

a) a channel is fed in continuous flow with a solution containing at least one sample. In some embodiments, the sample is supplied by applying a pressure difference between the feed basin and the outlet basin of said channel; and b) at least one reagent is injected from at least one reagent reservoir into said channel, in such a way as to mix said sample and said reagent.

The sample can then be removed from the outlet basin of said channel.

In another embodiment of the invention the process for carrying out chemical, biological or biochemical protocols on at least one sample comprises the following steps:

a) a channel is fed in continuous flow with a solution containing at least one sample. In some embodiments, the sample is supplied by applying a pressure difference between the feed basin and the outlet basin of said channel;

b) at least one reagent is injected from at least one reagent reservoir into said channel, in such a way as to mix said sample and said reagent; and c) at least one physicochemical parameter of said sample is detected. In some embodiments, the at least one physicochemical parameter is detected in said channel.

The processes in accordance with the invention preferably have at least one of the following properties:

the solution runs through at least one temperature regulated zone such that the solution is adjusted to a given temperature when it runs through said temperature regulated zone;

the solution runs through at least one temperature regulated zone which is brought successively to at least two given temperatures such that the solution is adjusted successively to said temperatures when it runs through said temperature regulated zone once;

the solution runs through a temperature regulated zone which is brought successively to at least two given temperatures following a temporal series which forms a predetermined cycle, such that the solution undergoes the temperature cycle at least once in running through the temperature regulated zone once; and the solution undergoes the temperature cycle a plurality of times, such as at least 1 to 50 times, or preferably 1 to 35 times, in running through the temperature regulated zone once.

Generally, the processes in accordance with the invention can be carried out according to a wide range of cycling protocols. A solution can undergo even temperature cycles where a temperature cycle is repeated essentially unchanged, or assymetric cycles where successive temperature cycles differ in some characteristic (time of cycle, flow rate, temperature transition time, temperature, etc.). Also, as described herein, temperature cycling can easily be varied by selecting a flow rate of the fluid, or cycle speed of the temperature regulated zone. In preferred embodiments, a computer program is used to select and control temperature cycling characteristics.

Controlling the temperature and carrying out thermal cycling are important elements for many enzymatic reactions and in particular for nucleic acid amplification reactions. The processes in accordance with the invention make it possible to integrate the mixing of the samples and reagents, as well as the various thermal treatments, and do not require manipulation.

To carry out very large scale protocols, the processes in accordance with the invention will preferably comprise one of the following steps:

the at least one channel is fed sequentially with a plurality of samples separated from each other by separators consisting of an inert fluid; and the various steps of the process are carried out simultaneously on a plurality of channels arranged in parallel.

The processes in accordance with the invention are also very advantageous for all the reactions which involve temperature cycling.

With a view to carrying out such protocols in one embodiment, a process is provided, according to the invention, for carrying out in continuous flow at least one temperature cycle on a solution containing at least one sample, which comprises the following steps:

a) a channel is fed in continuous flow with said solution containing at least one sample; and b) said solution is run through at least one temperature regulated zone which is brought successively to at least two given temperatures following a temporal series which forms a predetermined cycle, such that the solution undergoes the temperature cycle at least once in running through the temperature regulated zone once.

In another embodiment of the invention, a process is provided for carrying out in continuous flow at least one temperature cycle on a solution containing at least one sample, which comprises the following steps:

a) a channel is fed in continuous flow with said solution;

b) said solution is run through at least one temperature regulated zone which is brought successively to at least two given temperatures following a temporal series which forms a predetermined cycle, such that the solution undergoes the temperature cycle at least once in running through the temperature regulated zone once; and c) at least one physicochemical parameter of said sample is detected downstream of said channel.

Preferably, in some embodiments, the channel is fed in continuous flow by applying a pressure difference between the feed basin and the outlet basin of said channel.

Preferably, in some embodiments, the solution undergoes the temperature cycle at least 1 to 50 times, or more preferably 1 to 35 times in running through the temperature regulated zone once.

To carry out very large scale thermal cycling protocols, the processes in accordance with the invention will preferably comprise one of the following steps:

the channel is fed sequentially with a plurality of samples separated from each other by separators; and the various steps of the process are carried out simultaneously on a plurality of channels arranged in parallel.

The processes in accordance with the invention are also very advantageous for any nucleic acid amplification techniques.

In one embodiment of the invention, the process for amplifying nucleic acids in accordance with the invention comprises the following steps:

a) said nucleic acid is mixed with reagents which are suitable for amplifying nucleic acids;

b) a channel is fed in continuous flow with the reaction mixture;

c) this reaction mixture is run through at least one temperature regulated zone which is brought successively to determined temperatures following a temporal series which forms a predetermined cycle; and d) the temperatures and duration of the temperature cycle of the temperature regulated zone, as well as the time taken for the mixture to run through the temperature regulated zone, are chosen in such a way that the nucleic acid can undergo a denaturation-hybridization-elongation cycle several times while running through the at least one temperature regulated zone.

In another embodiment of the invention, the process for amplifying nucleic acids in accordance with the invention comprises the following steps:

a) a channel is fed in continuous flow with a solution comprising said nucleic acid;

b) at least one reagent which is suitable for amplifying nucleic acids is injected from at least one reagent reservoir into said channel, in such a way as to mix said nucleic acid and said reagent;

c) this reaction mixture is run through at least one temperature regulated zone which is brought successively to determined temperatures following a temporal series which forms a predetermined cycle; and d) the temperatures and duration of the temperature cycle of the at least one temperature regulated zone, as well as the time taken for the mixture to run through the temperature regulated zone, are chosen in such a way that the nucleic acid can undergo a denaturation-hybridization-elongation cycle several times while running through the at least one temperature regulated zone.

Preferably, the processes in accordance with the invention also have at least one of the following properties:

the channel is fed in continuous flow by applying a pressure difference between the feed basin and the outlet basin of said channel;

the channel is formed in a silicon substrate;

said channel is fed sequentially with a plurality of nucleic acids separated from each other by separators; and steps a), b), c) and d) are carried out simultaneously on a plurality of channels arranged in parallel.

The processes and devices in accordance with the invention make it possible to integrate, in continuous flow, large scale genotyping protocols and in particular microsequencing protocols.

With a view to detecting, in continuous flow, at least one nucleotide in at least one target nucleic acid, a process is provided which comprises the following steps:

a) a channel is fed in continuous flow with a solution comprising said nucleic acid;

b) the microsequencing reagent comprising the microsequencing buffer, the microsequencing primer, at least one ddNTP and a polymerase is injected into said channel in such a way as to mix said nucleic acid and said reagent;

c) the solution is run through at least one temperature regulated zone in such a way as to produce at least one cycle comprising the denaturation of the target nucleic acid, the hybridization of said nucleic acid with the microsequencing primer, and the incorporation of the ddNTP which is complementary to the nucleotide to be detected, at the 3' end of said primer; and d) at least one ddNTP is detected, which is incorporated at the 3' end of the microsequencing primer.

Optionally, this microsequencing process in accordance with the invention can comprise at least one of the following steps:

the channel is fed in continuous flow by applying a pressure difference between the feed basin and the outlet basin of said channel;

the temperature regulated zone is brought successively to determined temperatures following a temporal series which forms at least one cycle;

the ddNTPs are labelled with fluorophores, and in step d) the fluorescence of the incorporated ddNTP is detected; and steps a), b), c) and d) are carried out simultaneously on a plurality of channels arranged in parallel.

Advantageously, the microsequencing protocol is preceded by an amplification reaction to amplify a sequence comprising the nucleotide to be detected and, in yet another embodiment, a reaction for purification of amplification products. Reaction steps are integrated in the same microfluidic device in accordance with the invention.

In some embodiments, the process for detecting in continuous flow at least one nucleotide in at least one target nucleic acid comprises the following steps:

a) a channel is fed in continuous flow with a solution containing at least one target nucleic acid;

b) the reagent for amplifying the region of the target nucleic acid which carries at least one nucleotide to be detected is injected into said channel from a first reagent reservoir;

c) the solution is run through at least one temperature regulated zone in such a way that the nucleic acid may undergo a denaturation-hybridization-elongation cycle several times;

d) the reagent for purifying the amplification product is injected into said channel from a second reagent reservoir;

e) the solution comprising the amplification product is run through at least one temperature regulated zone to carry out the purification reaction;

f) the microsequencing reagent comprising the microsequencing buffer, the microsequencing primer, at least one ddNTP and a polymerase is injected into said channel from a third reagent reservoir;

g) the reaction mixture is run through at least one temperature regulated zone in such a way as to produce at least one cycle comprising denaturation of the target nucleic acid, hybridization of said nucleic acid with the microsequencing primer, and incorporation of the ddNTP which is complementary to the nucleotide to be detected, at the 3' end of said primer; and h) at least one ddNTP is detected, which is incorporated at the 3' end of the microsequencing primer.

The process in accordance with the invention can also comprise the following steps:

the channel is fed in continuous flow by applying a pressure difference between the feed basin and the outlet basin of said channel;

in steps c) and e) the at least one temperature regulated zone is brought successively to given temperatures following a temporal series which forms at least one cycle;

the ddNTPs are labelled with fluorophores, and in step h) the fluorescence of the incorporated ddNTP is detected;

the reagent for the purification comprises an exonuclease and an alkaline phosphatase; and steps a), b), c), d), e), f), g) and h) are carried out simultaneously on a plurality of channels arranged in parallel.

The processes in accordance with the invention are also very advantageous for carrying out chemical, biochemical, and biological reactions wherein changes in temperature of the reaction solution comprise a means of initiating, regulating, stopping, or otherwise affecting the reaction. In one embodiment of the invention, a process is provided for carrying out in continuous flow on a reaction solution at least one temperature cycle, wherein a) a channel is fed in continuous flow with said solution;

b) said solution is run through at least one temperature regulated zone which is brought successively to at least two given temperatures following a temporal series which forms a predetermined cycle, such that the solution undergoes the temperature cycle at least once in running through the temperature regulated zone once; and c) at least one physicochemical parameter of said reaction sample is detected. In some embodiments, the at least one physicochemical parameter is downstream of said channel.

A particularly advantageous aspect of the invention is the miniaturization of the reaction volumes. Typically, the reaction volumes are of the order of 0.01 µl to 10 µl. In a preferred embodiment of the invention, the reaction volumes are of the order of 0.1 µl to 5 µl. Preferably, the volume of the reaction volume is 0.1 to 2 µl.

Preferably, a chemical, biochemical, or biological reaction can be initiated when the reaction solution enters a temperature regulated zone having a given temperature. Equally advantageously, a chemical or biochemical reaction can be accelerated, or decelerated, or stopped, when the reaction solution enters a temperature regulated zone having a given temperature. In a further embodiment, the reaction products of a chemical or biochemical reaction may vary with the temperature at which a reaction is carried out, such that reaction products may be varied when the reaction solution enters a temperature regulated zone having a given temperature.

Equally advantageously, reaction products may undergo further manipulations in accordance with the invention including separation, purification, detection, identification, recovery, or further modification. Advantageously, components of a reaction solution are mixed in a single step; in another advantageous embodiment, components of a reaction solution are added sequentially, such that components may be added at any step or at any location as the mixture moves through the microfluidic device.

Thus, any number of further operations on a sample may be carried out in a variety of different formats. The sample may be further treated in the same microfluidic substrate as described above, or in another device or microfluidic substrate.

When a sample is further treated in another device or microfluidic substrate, said device or substrate may or may not be operably linked to the microfluidic substrate described above. In one embodiment, several microfluidic substrates are connected to a common support, such that samples from one substrate can flow directly to another substrate for further manipulation. As above, further manipulation can involve for example a separation, purification, detection, identification, recovery, or further modification step. In one preferred embodiment, products of a temperature cycling reaction are subjected to an enzymatic purification step in a microfluidic substrate comprising at least one temperature regulated zone, typically for activation or deactivation of said enzyme. In other embodiments of the invention, reaction products are purified by electrophoretic or chromatographic separation.

Other characteristics and advantages of the invention will appear in the description of preferred embodiments, which are given as examples and are non-limiting.

In the following descriptions identical, similar, or equivalent parts of the figures are referred to with the same numerical references to facilitate the reading thereof.

The Thermal Device

FIG. 1 schematically illustrates one embodiment of a microfluidics device according to the invention. A microfluidic substrate 100 is mounted upon a metal bar 900 which transfers heat to temperature regulated zones in the microfluidic substrate. The metal bar 900 contacts at least a portion of the microfluidic substrate to form at least one temperature regulated zone in the microfluidic substrate, as described below with reference to FIG. 2. The metal bar 900 is in communication with a system of valves (such as electrovalves or pressure valves) 910 through a system of pipes 920. The pipes 920 may be made of any conventional materials such as, for example, those used in traditional plumbing. The valves 910 may be actuated either manually or by an automated system controlled by a central processing unit. The valves 910 are, in turn, in communication with a plurality (three in the embodiment of FIG. 1) of reservoirs 930 by another set of pipes 940. The reservoirs 930 may be large tanks capable of holding a fluid. Each reservoir 930 is capable of maintaining the temperature of a fluid therein at a specified level by, for example, any of well-known heating or refrigeration means. The fluid in each reservoir 930 is maintained at a different temperature. In the present embodiment, the three reservoirs are maintained at 55° C., 72° C. and 94° C. However, the number and temperatures of the reservoirs may be any combination consistent with the protocol to be performed. Thus, the fluid in the reservoirs may heat or cool the temperature regulated zones to any desired temperature. For example, in some embodiments, a reservoir at 37° C. may be present in addition to the reservoirs at 55° C., 72° C. and 94° C. It will be appreciated that in embodiments employing more than one temperature regulated zone, each of the reservoirs may be in fluid communication with all of the temperature regulated zones or only with a portion of the temperature regulated zones in accordance with the protocol to be performed.

In a preferred embodiment of the invention, the fluid used is water. However, other liquids or gases, such as heated or cooled air, may also be used. Water, however, is an inexpensive and readily replenishable source and is, therefore, preferred.

The fluid is circulated from the reservoirs 930 via the pipes 940 through the valves 910. The valves 910 are actuated to allow fluid from only one reservoir 930 to pass to the metal bar 900 at the location of a temperature regulated zone in the microfluidic substrate. The fluid is then passed via the pipes 920 into the metal bar 900. The fluid passes through the metal bar, as described below with reference to FIG. 2, and is then returned to the reservoirs by way of the valves.

Figure 2:
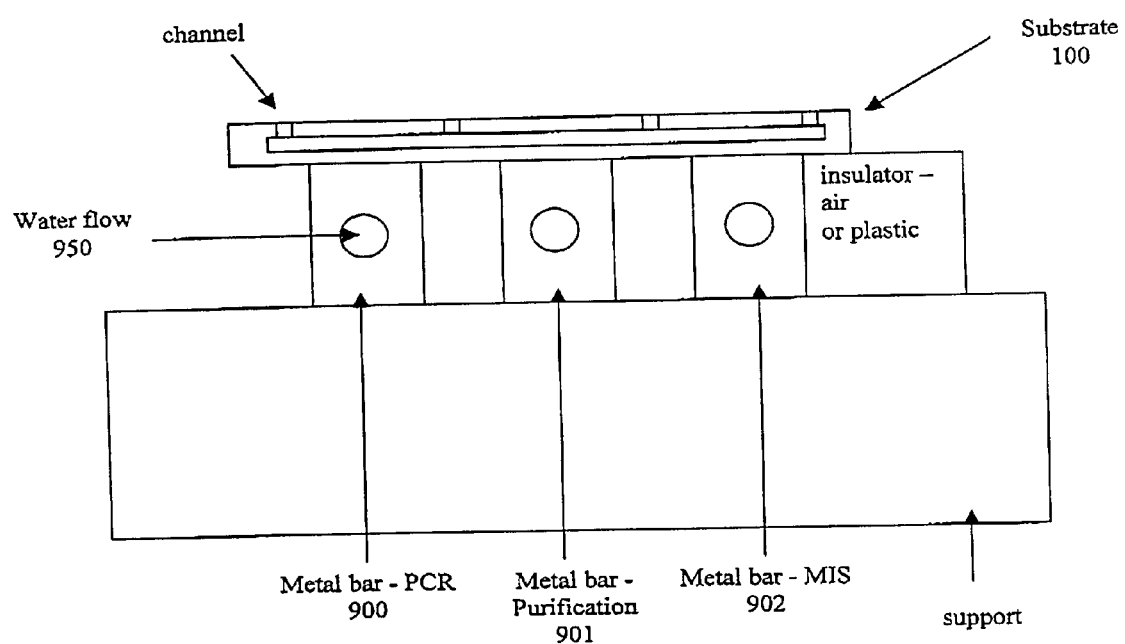
FIG. 2 is a cross-sectional view of the substrate-thermal support assembly taken along II—II of FIG. 1.

FIG. 2 is a cross-sectional view illustrating three metal bars 900, 901 and 902 and the microfluidic substrate 100 of FIG. 1. Each of the metal bars, as illustrated for metal bar 900 has a channel 950 formed therein. Each of the bars will provide thermal regulation (i.e., heating or cooling) to a temperature regulated zone of the microfluidic substrate. The channel 950 is in communication with the pipes 920 illustrated in FIG. 1. The fluid is passed through one pipe 920 into one end of a channel 950, through the channel 950 and to a return pipe 920. The return pipe 920 then directs the fluid back to the reservoirs by way of the valves.

In the present embodiment, in order to provide sufficient thermal regulation, water is flowed through each channel at a flow rate of approximately 400 liters per hour. This flow rate is maintained primarily by a system of pump and valves. However, the rate may also be controlled by installing pumps between the reservoirs and the electro-valves.

FIG. 2 illustrates the channel 950 in the metal bar 900 as having a circular cross section. The circular cross section is simple to form by, for example, drilling through the metal bar. However, other cross sections offer other advantages. For example, a flatter cross section across the face of the metal bar in contact with the microfluidic substrate exposes a larger area of the fluid to the microfluidic substrate, thereby increasing the rate of heat transfer or cooling. These preferred cross sections allowing increased heat transfer or cooling are more difficult to manufacture by, for example, molding or welding the metal bar.

The temperature in the temperature regulated zones may be more precisely controlled by installing temperature sensors in the zones. For example, two thermocouples and a platinum sensor may be used in combination to provide an accurate temperature. The thermocouples have a very fast response time but are not precise, while the platinum probe responds slowly but measure temperature more precisely compared to the thermocouples. Thus, the two types of readings provide a better reading of the temperature than would any individual reading. The temperature sensors allow an operator to monitor the temperature in the zones and, if needed, adjust the flow of fluid through the channels to adjust the temperature. Alternatively, the output from the temperature sensors may be routed to a central processing unit to automatically control the temperature via a feedback loop system.

As the fluid passes through the channels in the thermal device positioned below the microfluidic device, heat is transferred between the fluid in the thermal device, and a reaction mixture in the microfluidic device. The structure of the microfluidic device and substrate will be described below with reference to FIGS. 3A–12.

Microfluidic Substrate

Figure 3A:
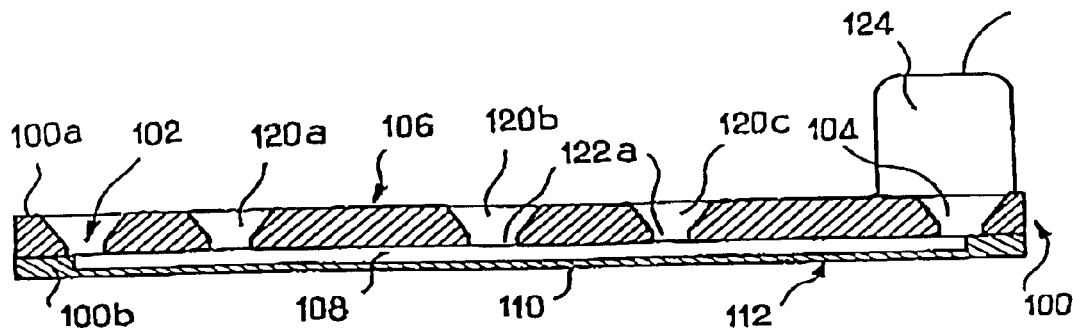
FIGS. 3A and 3B are cross-sectional views of embodiments of a microfluidic substrate according to the present invention.

FIG. 3A is a section of a microfluidic substrate 100 in accordance with the invention. In this figure is represented an inlet basin 102 which is formed essentially by a through-opening made in a substrate 100a, in the vicinity of one of its ends. Similarly, an outlet basin 104 is made in the vicinity of a second end. The basins 102, 104 open onto a first face 106 of the substrate 100. An internal channel 108 connects the inlet and outlet basins.

The channel 108 is in the form of a groove which is etched in a second substrate 100b which is bonded to the first substrate such that the latter covers the groove.

It is observed that in the illustrated embodiment the depth of the groove is practically equal to the thickness of the second substrate 100b, such that only a thin wall 110 separates the channel 108 from a second face 112 of the microfluidic substrate 100.

In the example illustrated, the substrate 100 is of parallelepipedic general form and the first and second faces 106, 110 are the principal faces, which are opposite and parallel. The figure also represents, in section, reagent reservoirs 120a, 120b, 120c which are arranged between the inlet or feed basins 102 and the outlet basins 104. The device may have any number of reagent reservoirs consistent with the protocol to be performed. The reservoirs also open onto the first face 106 of the analysis support 100. Connectors, or passages, 122a are provided to connect each of the reservoirs to the channel 108.

For reasons of simplification, the passages 122a are represented in the plane of the figure such that the reservoirs are not different from the feed and outlet basins in FIG. 3A.

Fluid Feed Systems

Figure 3B:
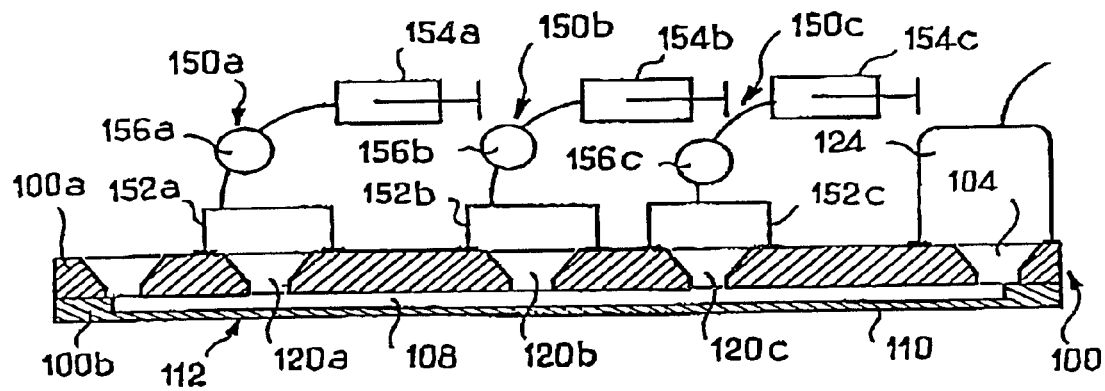

FIG. 3B shows a microfluidic substrate in accordance with FIG. 3A, whose reservoirs 120a, 120b and 120c are respectively associated with fluid supply components, 150a, 150b and 150c.

These components comprise feed separators or caps 152a, 152b, 152c which are tightly applied over the reservoirs and which are connected to syringe drivers 154a, 154b and 154c which contain reagents. The caps can be bonded to the surface of the microfluidic substrate or tightened against the surface using a water-tight seal.

The references 156a, 156b and 156c refer respectively to pressure sensors which are arranged on pipes connecting the syringe drivers to the caps 152a, 152b and 152c, in such a way as to control the pressure and/or the flow rate of the reagents.

Although not represented, a similar feed system can also equip the feed or inlet basins.

Figure 4:
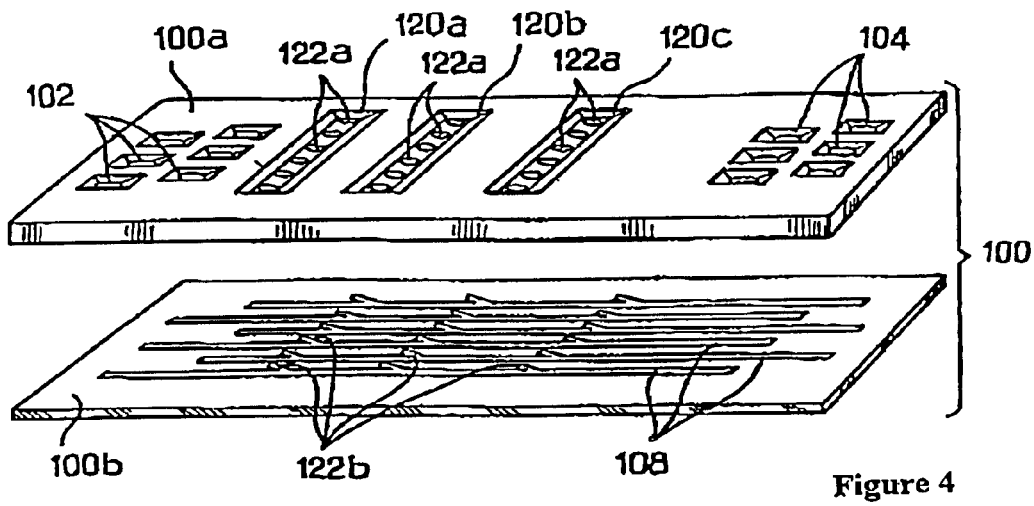
FIG. 4 is an exploded view of a microfluidic substrate according to the invention.

As is shown in FIGS. 3A and 3B, the inlet basins and the reservoirs are subjected to atmospheric pressure or a pressure which is fixed by the feed system, whereas a vacuum line 124 is applied to the outlet basins. FIG. 4 shows more precisely, and separately, the two substrates 100a and 100b which form the microfluidic substrate.

It is observed that the microfluidic substrate comprises a plurality of feed basins 102 and a plurality of outlet basins 104.

The basins have the form of through-openings made in the first substrate 100a. These openings have a splayed V-shape, which forms a funnel. Moreover, in the example in FIG. 4 each inlet basin 102 is individually connected to an outlet basin 104 by a channel 108. The microfluidic substrate comprises three reagent reservoirs 120a, 120b, 120c. In this example, each reservoir is common to several channels 108 to which it is connected by means of connectors 122a, 122b. The reference 122a refers more specifically to perforations in the first substrate 100a which connect a reservoir to corresponding branches 122b, which are made in the second substrate 100b and are connected respectively to the channels. Of course, reservoirs can also be separated for the various channels.

The amounts of fluid (samples and reagents) which mix at the junction of the branches 122b and the channels 108 depend on the respective size of these branches and of the channels 108.

Thermal Support

Figure 5:
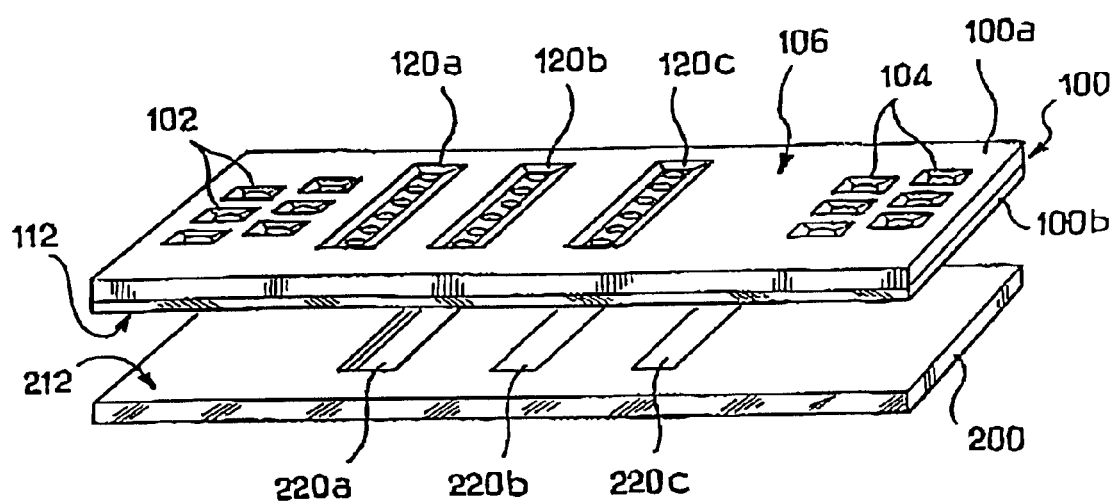
FIG. 5 is an exploded view of the microfluidic substrate and the thermal support according to the invention.

As described above, the microfluidic substrate may also comprise a thermal support. FIG. 5 shows a microfluidic substrate 100, in accordance with that of FIG. 4, whose substrates 100a and 100b are permanently bonded to each other. The microfluidic substrate is represented above a corresponding thermal support 200.

The thermal support 200 has a heat exchange face 212 which faces the second face 112 of the microfluidic substrate 100, in the vicinity of which the channels are located. The heat exchange face 212 has three temperature regulated zones 220a, 220b, 220c, each equipped with one or more heat sources (not represented).

The three temperature regulated zones 220a, 220b, 220c are arranged in such a way as to coincide with portions of channels of the microfluidic substrate which are situated in the vicinity, respectively, of the reservoirs 120a, 120b, 120c, or more precisely of the branches which supply the reagents.

Figure 6:
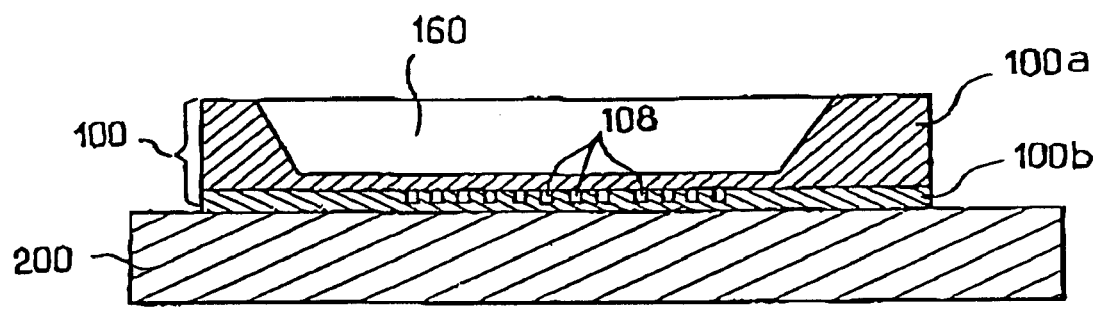
FIG. 6 is a cross-sectional view of another embodiment of a microfluidic substrate and thermal support system.
Figure 7:
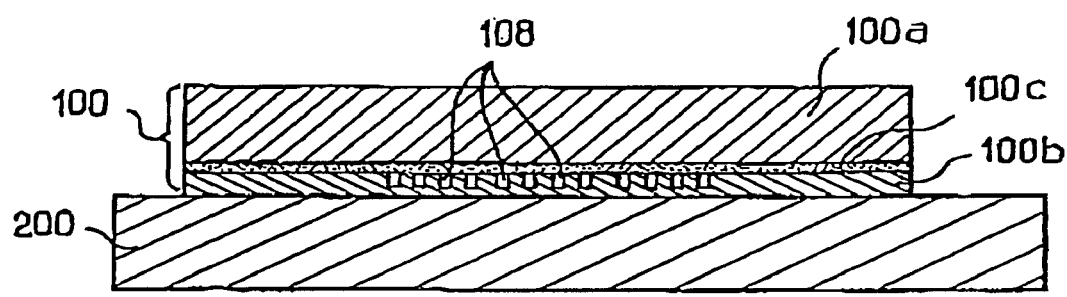
FIG. 7 is a cross-sectional view of yet another embodiment of a microfluidic substrate and thermal support system according to the invention.

Generally, but not by way of limitation, it is advantageous if the microfluidic substrate comprising the channels is thermically isolated from the top (ie. not in contact with a good thermal conductor). In this regard, FIGS. 6 and 7 show two embodiment variants of the device which make it possible to improve the regularity of the temperature in the channels by isolating their upper face, i.e. the face opposite said second face 112 of the microfluidic substrate. A first solution, represented in FIG. 6, consists in making a cavity 160 (with or without an opening) in the upper part 100a of the support. This cavity coincides with at least one part of the channel 108. A second solution, represented in FIG. 7, consists in positioning a layer 100c of heat-insulating material between the upper and lower parts 100a, 100b of the microfluidic substrate. Access holes are formed in the insulating layer 100c corresponding with the reagent reservoirs 120a, 120b, 120c.

As described above for the microfluidic substrate, the thermal support may comprise, consist essentially of, or consist of any suitable material, including but not limited to a plastic, silicon, glass or quartz.

Processes for Manufacturing a Microfluidic Substrate

In a particular embodiment of the microfluidic substrate, it can comprise a first substrate, which has through-openings which form respectively the basins, the connectors and the reservoirs, and a second substrate, which is bonded to the first substrate, which has grooves which are covered by the first substrate to form channels, and which coincide respectively with the through-openings. This particularly simple structure makes it possible to reduce the costs of manufacturing the microfluidic substrates. The manufacture of the microfluidic substrate can take place, in accordance with the invention, according to a process comprising the following successive steps:

forming, in a first substrate, through-openings, said through-openings corresponding respectively to feed basins or to outlet basins or to reagent reservoirs;

forming, in a second substrate, grooves according to a pattern which makes it possible to mutually connect at least two openings of the first substrate; and bonding the first substrate onto the second substrate in such a way as to cover the grooves FIGS. 8 to 11 described below, give an example of a process for preparing a microfluidic substrate as described above.

Figure 8:
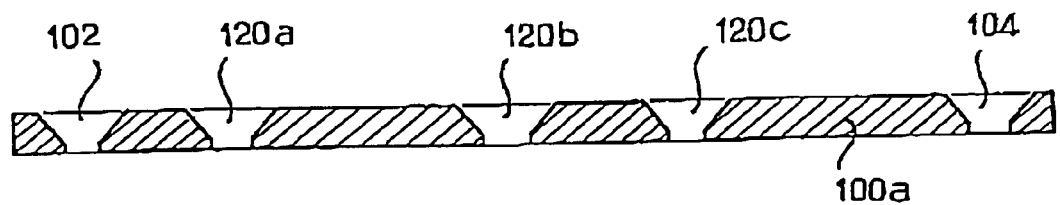
FIGS. 8–11 are cross-sectional views of the microfluidic substrate at various phases of assembly.

As is shown in FIG. 8, through-openings are made in a first substrate plate 100a, for example made of silicon. These through-openings constitute the basins or the reservoirs 102, 104, 120a, 120b, 120c. The openings, which are chemically etched, are prepared with sloping sides by anisotropic chemical etching, for example using KOH, in such a way as to confer thereon a splayed shape. The positioning of the openings is defined by an etching mask (not represented) which coincides with the pattern of the grooves. The perforating of the layer 100c of heat-insulating material, for example $SiO_2$ in the case of the embodiment provided in FIG. 7, can be performed, for example, by dry etching with $CHF_3$, the size of the perforation being defined by an etching mask or by using the walls of the chemically created hole as a mask.

Figure 9:
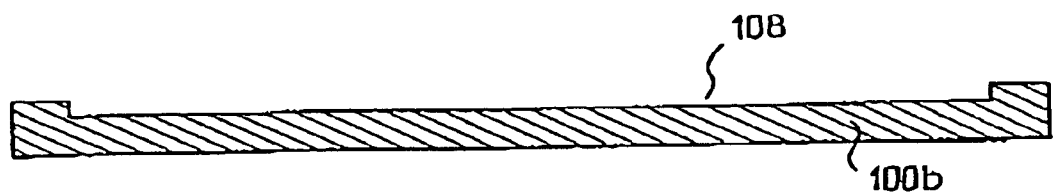

FIG. 9 shows the etching of grooves which form the channels 108, in a second substrate 100b, for example of silicon. The etching is performed through an etching mask (not represented) having a pattern which corresponds to the desired channels. It is for example a chemical etching using (KOH). The depth of the grooves is for example of the order of 100 $\mu$m for a substrate 100b with a thickness of 250 to 450 $\mu$m. It can also be a dry etching SF6 which makes it possible to prepare grooves which are deeper than they are wide, for example 100 $\mu$m×20 $\mu$m.

Figure 10:
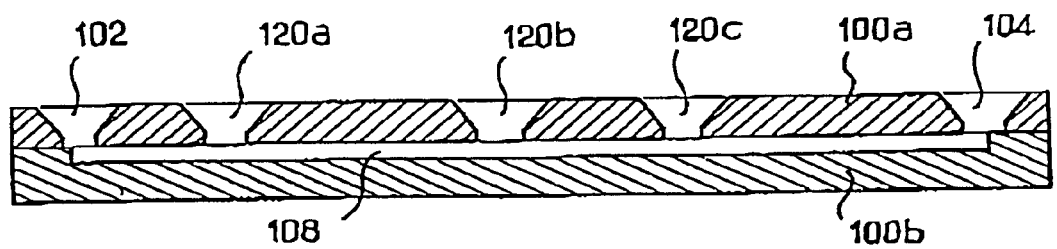

A third step, represented in FIG. 10, comprises the sealing of the first and second substrates 100a and 100b, in such a way as to place the basins or reservoirs 102, 104, 120a, 120b, 120c in communication with the corresponding channels (grooves) 108. The sealing occurs, for example, by direct (molecular) bonding of the two substrates.

During this operation, the grooves 108 of the second substrate 100b are covered by the first substrate 100a to form the channels.

Figure 11:
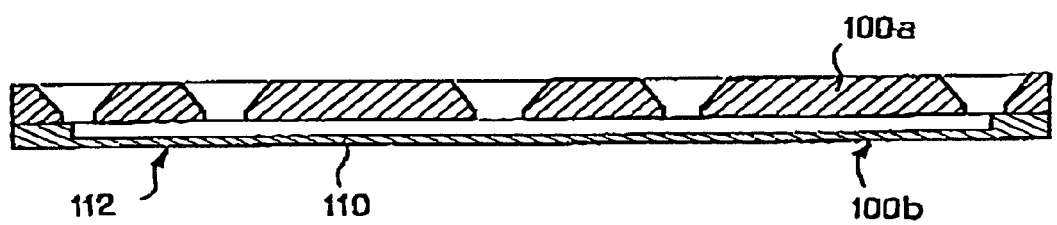

A final step, represented in FIG. 11, comprises the thinning of the second substrate 100b in such a way as to preserve only a thin wall 110 between the channel 108 and the outside surface 112.

This wall 110 has a thickness of the order of about 50 $\mu$m in such a way as to promote good thermal isolation between two temperature regulated zones. As described above, optionally, the wall 110 can be thinned to promote heat exchange by etching and/or by mechanochemical polishing.

A plurality of microfluidic substrates in accordance with the invention can be manufactured simultaneously and together, according to the above process, in two silicon wafers (corresponding to the first and second substrate). In this case, the process is completed by cutting up the wafers with a saw, to separate the microfluidic substrates.

Devices and Processes for Carrying out Chemical, Biochemical, and Biological Protocols with Thermal Cycling The devices and processes in accordance with the invention make it possible to carry out, in continuous flow, chemical, biochemical, and biological protocols which include a step involving thermal cycling. Chemical, biochemical, and biological protocols envisioned for use in accordance with the invention comprise protocols in which changes in temperature are useful for initiating, accelerating, decelerating, stopping, quenching, diverting, or otherwise affecting chemical or biochemical processes. The present invention relates to, inter alia, the polymerase chain reaction (or PCR), which is widely used in genetic analysis. The invention, which can be used in genetic analysis, can also be used for numerous protocols in the domain of biochemistry and of molecular biology.

Polymerase Chain Reaction

The polymerase chain reaction (PCR) is well known in the art. PCR utilizes the fact that two complementary DNA strands are capable of reversibly hybridizing to form a double-stranded molecule, and separating into single DNA strands. The double- or single-stranded state depends on the conditions of stringency (pH, salt, temperature).

PCR relies on the fact that in cells, DNA is duplicated in such a way as to ensure the transmission of the genetic information. Synthesis of DNA involves the action of DNA polymerase enzymes. Starting from a matrix DNA strand, DNA polymerases incorporate opposite each nucleotide another nucleotide which is complementary to it, thus creating a new strand of DNA by a process known as elongation.

To carry out DNA synthesis in vitro, the polymerase must be supplied with, in addition to the matrix and the dNTPs, a primer which will initiate the polymerization. This primer is a short fragment of DNA (preferably about twenty nucleotides) which is complementary to one end of the matrix DNA fragment. To obtain double-stranded DNA, two primers are required: one complementary to each strand, on either side of the target sequence whose amplification is desired.

To make multiple copies of a strand of DNA, PCR utilizes the denaturing and hybridizing capacities of DNA, in combination with elongation by a polymerase. The temperatures at which each of the steps is performed may be selected as appropriate for the primers and target sequences being used. For example, the steps for one method for performing PCR are as follows:

denaturation of the DNA by heating the solution to 94° C., to completely separate the two strands of DNA and to remove the secondary structures;

hybridization of the primer onto the single strand, achieved by lowering the temperature to allow specific pairing; and elongation of a strand of DNA by setting the temperature to the optimum for activity of the heat-stable polymerase, for example 72° C. for certain enzymes.

After these three steps, which are herein defined as constituting a "cycle," denaturation is again carried out, and the newly synthesized DNA will be used as matrix. Cycles are repeated twenty to forty times, leading to an exponential increase in the amount of matrix. It will be appreciated that the number of cycles and the temperatures at which the various steps in the cycles are performed may be any value consistent with the desired amplification.

An example a protocol for amplification by PCR which has been carried in a microfluidic substrate according to the invention is provided in Example 1.

Temperature Cycling and Genetic Analysis

In genetic analysis, numerous protocols exist which require temperature cycling. Amplification techniques which are derived from the PCR are known, such as RT-PCR, allele-specific PCR and Taq Man PCR (White, B. A., Methods Mol Biol 67:481–486 (1997); Delidow, B. C. et al., Methods Mol Biol 58: 275–292 (1996), the contents of which are incorporated herein by reference in their entireties). Ligase chain reaction (LCR) techniques are also well known, including LCR, gap LCR, asymmetric gap LCR, reverse transcription LCR (RT-LCR), the oligonucleotide ligation assay (OLA) and PCR-OLA (Nikiforov, T., Anal Biochem 225: 201–209 (1995); Marshall, R. L., PCR Methd Appl 4: 80–84 (1994); Nickerson, D. A. et al., Proc Natl Acad Sci USA 87: 8923–8927 (1990), the contents of which are incorporated herein by reference in their entireties). Cyclic sequencing reactions using clones or PCR reactions are known. Cyclic microsequencing (single nucleotide primer extension) reactions are known (Cohen, D., International patent publication no. WO 91/02087, incorporated herein by reference in its entirety). Further exemplary protocols include reverse-transcriptase and nested PCR (RT-nested PCR) of expressed sequences, followed by cycle sequencing (Happ et al., Vet Immunol Immunopathol, 69: 93–100, (1999), incorporated herein by reference in its entirety); a degenerate PCR technique can be used as a first step to identify and amplify the actual sequence when it is not completely known (Harwood et al., Clin Microbiol 37: 3545–3555, (1999), incorporated herein by reference in its entirety); random amplified DNA (RAPD) analysis, often useful as a exploratory approach (Speijer et al, Clin Microbiol 37: 3654–3661, (1999), incorporated herein by reference in its entirety); and arbitrarily primed PCR (AP-PCR), often useful as a preliminary step to find potential polymorphisms (Jonas et al., Clin Microbiol 38: 2284–2291, (2000), incorporated herein by reference in its entirety).

Although various devices have been designed for implementing chemical, biochemical, and biological protocols comprising steps that include at least one thermal cycle, these devices have serious drawbacks. Advantages provided by the present invention are apparent from comparing other devices with the present invention.

In one type of known device, the biological sample is placed in a reservoir which is brought successively to the required temperatures for obtaining the desired heat treatments. Certain devices use a system of thermostatting or thermal regulation by Peltier effect. The heat response time of these devices is on the order of 3° C. per second (3° C./s). Although the method used by these devices is simple to implement, the cycle times resulting therefrom are very long for carrying out the entire protocol. This approach does not make it possible to increase the reaction throughput or yield.

Other techniques use a reservoir etched in a silicon substrate. The heating of the reservoir is obtained by an electrical resistor which is formed by a platinum deposit. The cooling of the reservoir is obtained by permanent conduction on a cold plate. To improve the heat response time during the temperature cycles, the reservoir (or reaction chamber), is suspended by silicon beams which are produced by chemical etching in the substrate. The heat response time is greater than about ten degrees per second. The technique used is however relatively incompatible with the integration of the protocols in a "laboratory on a chip", i.e. in a microfluidic substrate where the principle is to make the liquids circulate between various biological or biochemical reactions zones. In this device, it is not possible to achieve continuous flow and thus to integrate a protocol adapted to high throughput screening.

Figure 12:
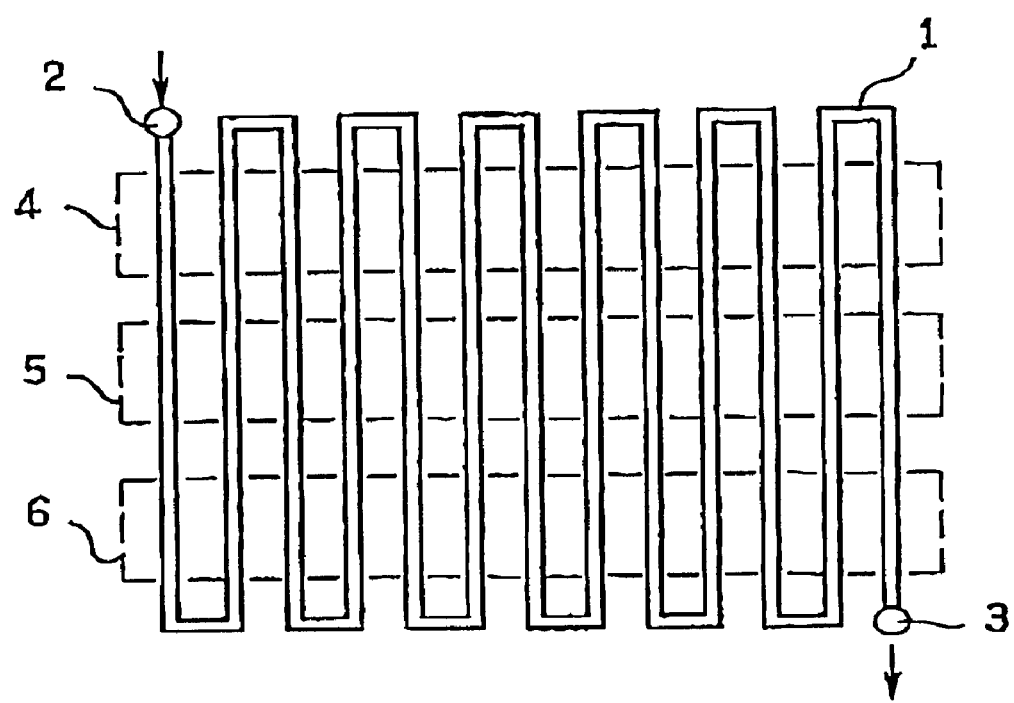
FIG. 12 is a schematic view of a microfluidic system in the prior art.

In another type of known device, microchannels which make it possible to circulate biological fluids are micromachined on a substrate made of silicon, glass or polymer material. These microchannels or capillaries make it possible to continually circulate the samples. The fluid successively crosses zones at temperatures which are fixed according to the heat treatments required. This solution leads to the production of microchannels in the form of coils. FIG. 12 illustrates a device of this type, presenting a view from above of a substrate in which a microchannel 1, represented figuratively, has been formed. The microchannel 1 forms a coil between an inlet orifice 2 and an outlet orifice 3. The references 4, 5 and 6 represent zones which are subjected to temperatures T1, T2 and T3 respectively. The coil comprises active sections in which the fluid to be treated undergoes the denaturation-hybridization-elongation cycle; these active sections alternate with sections not subject to temperature regulation which are used to bring the fluid back into the zone which is at denaturation temperature.

A major drawback of this arrangement is that it imposes limits which are prohibitive for miniaturization, flexibility and throughput (in the sense that it is not feasible to have a large number of parallel chennels). In fact, it is necessary to have as many heat zones as there are different temperatures in a thermal cycle. In addition, each heat zone should be separated by a sufficient distance from another heat zone to guarantee a standardized temperature in the isothermal zones. Another obstacle is due to the number of loops of the coil, which corresponds to the number of thermal cycles desired, making it difficult to miniaturize, run in parallel and change the number of cycles if a different reaction is to be carried out, for example. Furthermore, due to the length of the channels, significantly higher channel pressure must be used, representing a potentially difficult implementation. The miniaturization involves a decrease in the width of the channels, which poses fluidic problems (risk of blockage and heat losses and, potentially, increased adsorption). In addition, at the liquid flow rate necessary for such a device, the outflow speeds become considerable, since the length of a heat zone should be equal to the time of the reaction multiplied by the speed of the liquid, which means the dimensions of the heat zones have to be increased.

UK Patent Application no. GB-2 325 464-A (Bruken-Franzen Analytik GmbH) discloses yet another type of device. In this device the reaction chamber comprises a plurality of parallel microchannels, having a common inlet and outlet. The fluid to be treated enters into the reaction chamber and is subjected to three different temperatures, either in three separate zones or in the same zone. The device is not designed to work in continuous flow since the fluid is maintained stationary during the steps of the process. At best, the circulation of the fluid can be resumed during the elongation step. This solution involves sequential means of circulating the fluid which are quite complex, and which must be perfectly coordinated with the temperature cycles.

U.S. Pat. No. 5,736,314 describes a device in which it is possible to implement PCR. The solution runs through a tube which is surrounded by circular heating elements. Each element heats the segment of tube which it surrounds to a given temperature. As it flows through the tube, the solution is subjected to suitable temperatures make it possible to implement PCR. A drawback of this device is that it requires having as many heat zones as there are different temperatures in a cycle, and as many heat zones as there are cycles. This renders the circuit of the solution particularly long. In addition, each heat zone must be isolated as well as possible from the adjacent zones, to guarantee as far as possible a standardized temperature in each zone. However, this is difficult to achieve in practice and/or very costly, and it also lengthens the circuit.

None of the devices of the prior art makes it possible to treat a sample with a continuous flow thermal protocol while optimizing the following parameters:

minimal active surface for the device;
   maximum flow rate of treated substance (reaction volume per unit time); and
   maximal channel section for a minimal internal surface of the channels.

An object of the present invention is to produce a thermal cycling device which makes it possible to reduce the length of the circuit of the solution and to obtain, at low cost, the temperatures which are exactly those required for the thermal cycling.

With a view to achieving this aim, a device is provided according to the invention for carrying out chemical, biochemical, or biological reactions with thermal cycling, which comprises at least one channel, at least one means for continuously feeding the channel with a solution and at least one means for providing the channel with at least two predetermined temperatures such that the solution is adjusted to these temperatures when it runs through the channel once, the device comprising components for transferring the channel from one to another of the temperatures over time, while the solution runs through the channel.

Thus, the entire solution circulating in the channel (or in the segment of channel under consideration), is brought successively to the different temperatures required by the thermal cycling. By choosing the flow speed, the number of times that the solution undergoes the cycling in the channel is thus determined. The lower the flow speed of the solution, the greater will be the number of cycles.

The present invention makes it possible to reduce the dimensions of the device, which reduces the cost of production. Using a single heat zone for the channel eliminates the difficulties which appear in the prior art with neighbouring heat zones at different temperatures. All the thermal isolating zones between each temperature of each cycles are suppressed, which reduces considerably the size of the circuit. The invention makes it possible for the channel to have a linear configuration, which is easy, and thus relatively inexpensive, to manufacture. It is very advantageous to eliminate bends and decrease the length of the channels. Firstly, when the fluid circulation is effected by an electrokinetic means, channels with curves and bends dramatically influence the fluid profile of the sample in the channel. Maintaining the fluid profile of the sample essentially perpendicular to the channel wall allows the advantage of maintaining an identical flow speed in all the sections of the channel. Secondly, when the fluid circulation is effected by a pressure-based means, channels with small diameters and curves and bends require high pressure, increasing the stress on the whole system in particular on connections. Very slow flow rates can be used since the length of the circuit can be short. Shorter and straighter channels provide many advantages, in particular when the liquid is moved by pressure, because the (pressure) head losses are much smaller. The present invention makes it possible to rapidly treat a large amount of solution since the thermal cycling takes place with a continuous flow of liquid.

The invention makes it possible to perform numerous protocols including, but not limited to:

all the types of PCR such as PCR, RT-PCR, allele-specific PCR, Taq Man PCR, etc.;
   all the types of LCR (Ligase Chain Reaction) such as LCR, Gap LCR, Asymmetric Gap LCR, RT-LCR, Oligonucleotide Ligation Assay (OLA) and PCR-OLA;
   cyclic sequencing reactions from clones or from PCR reactions;
   cyclic microsequencing reactions (single nucleotide primer extension);
   genotyping protocols including OLA;
   any other biological operation requiring thermal cycling;
   any other biochemical process in which exposure of the reaction mixture to at least one thermal cycle will produce a desired effect; and
   any chemical process in which exposure of the reaction mixture to at least one thermal cycle will produce a desired effect
   any biological process in which exposure of the sample mixure to at least one thermal cycle will produce a desired effect.

In some embodiments, the invention has at least one of the following properties:

the microfluidic device is constructed such that the solution is adjusted to the desired temperatures following a temporal series which forms a predetermined temperature cycle, and such that the solution undergoes the cycle at least once when it runs through the channel once;
   the microfluidic device is constructed such that the solution is adjusted to at least two different temperatures when it runs through the channel once;
   the microfluidic device comprises at least two mutually communicating channels and allows each channel to be provided with at least a first and a second predetermined temperature, further allowing a solution in a channel to be transferred from the first to the second temperature such that the solution is brought to the first and second temperature of the given channel only once when it runs through each channel;
   the microfluidic device comprises at least one channel which is at constant temperature during a predetermined period and which communicates with a primary channel, wherein the temperature in the primary channel can be modified.
   the microfluidic device comprises several channels arranged in parallel with each other, the channels having mutually identical temperatures at any given instant;
   the microfluidic device comprises a substrate into which the one or more channels are formed; and
   the substrate comprises, consists essentially of or consists of silicon, glass, quartz and/or plastic.

A process is also provided according to the invention for carrying out chemical or biochemical reactions involving thermal cycling, in which at least one channel is fed continuously with a solution, and the solution is provided with at least two predetermined temperatures such that the solution is adjusted to the desired temperatures when it runs through the channel once, and in which the channel is transferred from one to another of the temperatures over time while the solution runs through the channel.

In one embodiment, the process has at least one of the following properties:
  the reaction comprises DNA or DNA fragments;
  the reaction implements a synthesis of DNA or of a fragment of DNA; and
  the reaction comprises a polymerase chain reaction.

A product is also provided according to the invention, which has undergone a chemical or biochemical reaction which is carried out according to a process in accordance with the invention.

We will describe, with reference to FIGS. 13 to 17, the principles of five embodiments of the device of the invention, applied herein to the implementation of a PCR protocol with thermal cycling.

Figure 13:
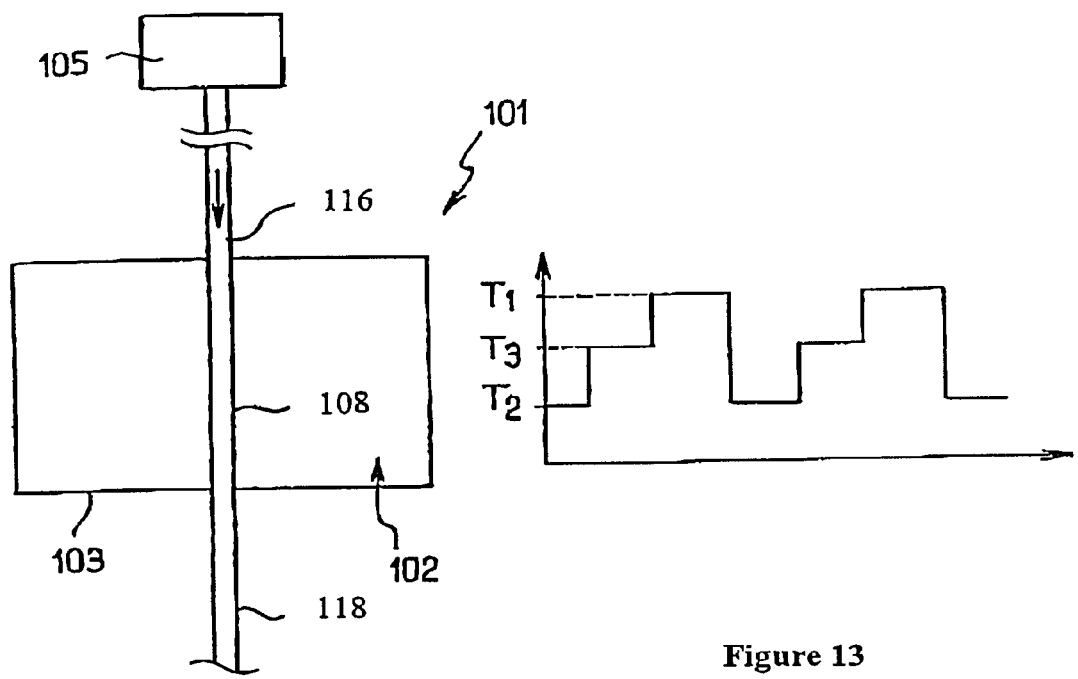
FIGS. 13 to 17 are schematic views of devices according to five embodiments respectively.

In the first embodiment illustrated in FIG. 13, the device 101 comprises a thermal cycling unit 102 comprising a substrate 103. The substrate will be described below in greater detail with reference to FIGS. 18 to 20. The substrate 103 has a channel 108 which is in fluid communication, via its upstream end, with an upstream feed pipe 116 and, via its downstream end, with a downstream outlet pipe 118.

The device 101 comprises components 105 for continuously running through the channel 108 a solution which is supplied via the pipe 116 and which leaves via the pipe 118, the solution thus running through the channel 108 a single time throughout its length during the entire protocol. The solution contains the reagents required for carrying out the PCR.

The unit 102 comprises components for heating or cooling the substrate 103 at will, these components being conventional and known per se. In some embodiments, the heating components comprise reservoirs containing solutions at the desired temperatures which are in fluid communication with channels in a metal bar which contacts the microfluidic substrate as illustrated in FIGS. 1 and 2. In the following and for simplicity, these components will be termed heating components, it being understood that they are used for heating and for cooling, and thus make it possible to raise or to lower the temperature of the substrate and of the channel. The heating components are constructed so as to heat or cool the substrate 103 in its entirety, such that whatever the temperature that they confer on the channel 108 at a given instant, all the segments of the channel 108 are at the same temperature.

The unit 102 comprises components for controlling the heating components, so that they provide the channel 108 with different successive temperatures over time. These temperatures herein number three, and are those which are known and which are used during the PCR. Thus, the channel 108 is first placed at a temperature T1, then cooled to a temperature T2, then reheated to an intermediate temperature T3. This temporal series forms a temperature cycle. This cycle is repeated numerous times over time, as is illustrated by the graph in FIG. 13. Thus, after a period at the temperature T3, the channel 108 is once more placed at the temperature T1 for the start of a new cycle and so on.

This cycling is performed while the solution runs through the channel from the feed pipe 116 as far as the outlet pipe 118. The section of the channel 108 and the speed of the solution are chosen herein such that the solution which is brought to the different temperatures T1, T2 and T3, between entering and leaving the channel, undergoes the cycle twenty to thirty times for example. Consequently, the different PCR reactions follow one after another in the same channel in a serial manner due to the continuous flow. The various segments of the channel which from upstream to downstream have, at a given instant, the same temperature, are different only in that they are crossed by respective fractions of solution, or different PCR reactions, which have already undergone a number of thermal cyclings which increase as these fractions of solution approach the outlet pipe.

Figure 14:
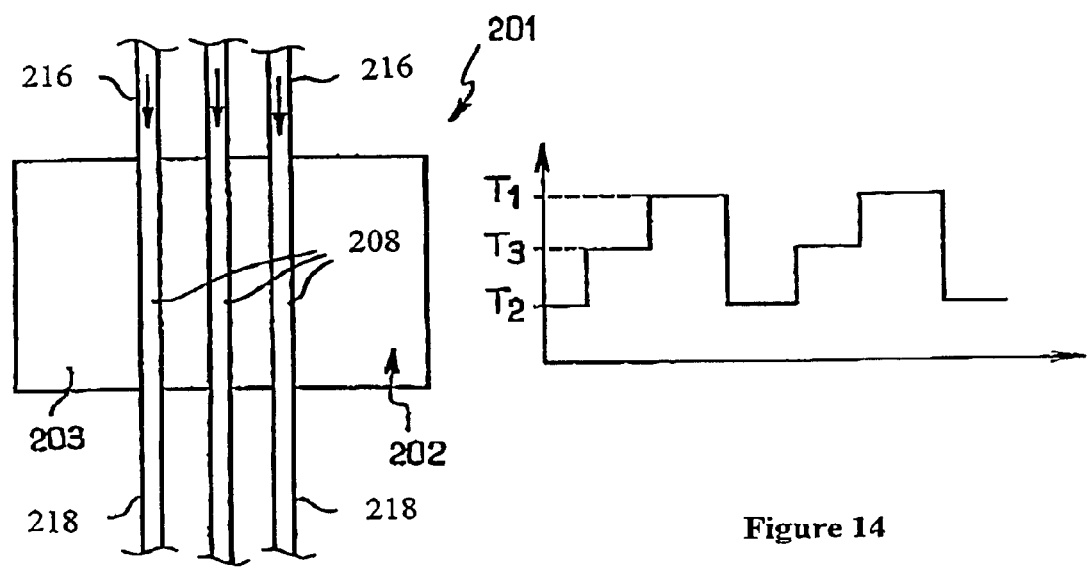

The second embodiment, illustrated in FIG. 14 with references increased by 100, is different from the previous embodiment only in that several channels 208 stretching out in parallel are made in the substrate 203. In each channel 208 of this embodiment the same thing happens as happened in the channel 108 of the first embodiment. In particular, the heating components perform the same thermal cycling over the entire substrate. In this second embodiment, at any instant, all the segments of all the channels 208 have the same mutual temperature. The channels 208 each have herein their own feed and outlet pipes. Different solutions can thus be treated at the same time. Alternatively, the channels 208 might be associated with common feed and outlet pipes, for example if the same solution runs through the various channels.

Figure 15:
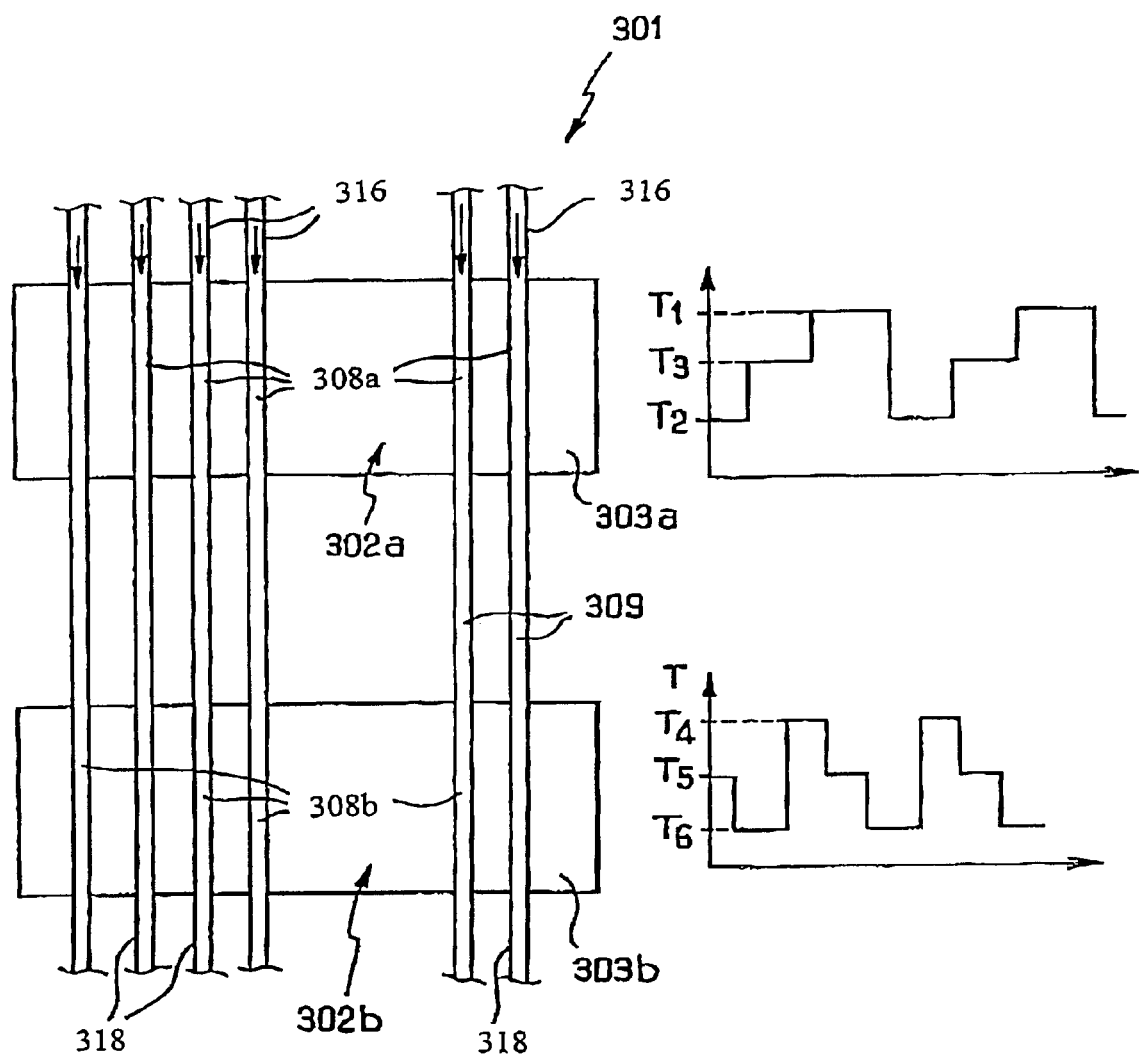

In the third embodiment, illustrated in FIG. 15, and for which the references of the analogous elements are increased by 200, the device comprises several channels once again. In addition, this time it no longer comprises one single unit of thermal cycling 302 (with a substrate, heating components and control components), but several units 302a, 302b of this type, for example numbering two. The two units 302a, 302b are arranged in series such that the channels 308a, 308b of the upstream unit 302a communicate through their downstream end and, via respective transfer pipes 309, with the upstream ends of the channels 308b of the downstream unit 302b. Each set of mutually communicating channels forms a circuit.

The upstream unit 302a is identical per se to that of the second embodiment and subjects the solution to the thermal cycling already described associated with the temperatures T1, T2 and T3. The downstream unit 303b performs, in this particular case, a thermal cycling whose parameters are different from those of the cycling of the upstream unit. Thus this downstream cycling is associated with three temperatures T4, T5 and T6, which are different from the temperatures T1, T2 and T3. In addition, the duration and the series of the temperatures, illustrated in the graph below in FIG. 15, are different from those of the first cycling. Consequently, the solution running through each circuit first undergoes the cycling of the upstream unit 302a several times, as it runs through this unit, then crosses the transfer pipe 309 and arrives at the downstream unit 302b where it undergoes this unit's own cycling, and this happens several times as long as the speed of the solution in this unit is sufficiently slow. The solution finally leaves the device 301 via the outlet pipe 318.

Figure 16:
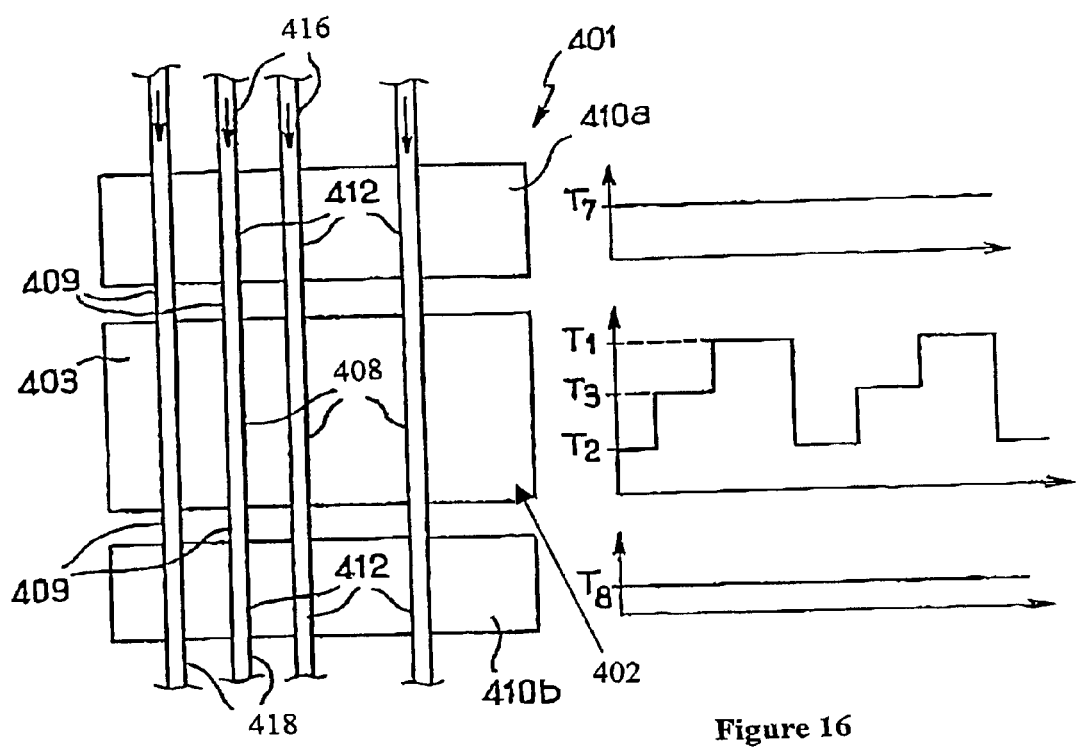

In the device according to the fourth embodiment, illustrated in FIG. 16, the numerical references of the analogous elements have been increased by 300. The device 401 comprises a thermal cycling unit 402 which is similar to that of the second embodiment. It also comprises two units 410a and 410b which each comprise a substrate 403 and means for maintaining in the channels 412 which cross these units, a temperature, T7 and T8 respectively, which is constant over time. The three units 410a, 402 and 410b are arranged in series and in this order, with their respective channels in communication from upstream to downstream. Thus, the solution introduced into a feed pipe 416 runs through a channel 412 of the upstream unit 410a, where it is placed at the constant temperature T7 for a predetermined period, in particular longer than the duration of one cycle of the unit 402. Next it clears the transfer pipe 409 and then arrives at the thermal cycling unit 402 where it undergoes the thermal cycle several times. Then, passing through the second transfer pipe 409, the solution runs into the downstream unit 410b, which is at constant temperature T8, where it remains at this temperature for another predetermined period. It is then evacuated from the device via the outlet pipe 418.

Figure 17:
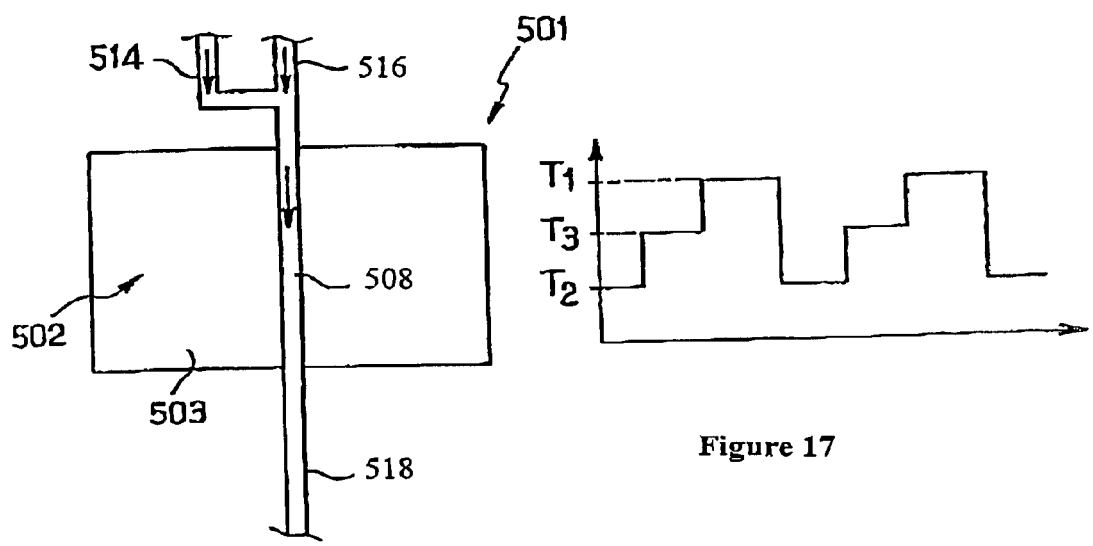

With reference to FIG. 17, in which the analogous elements bear references which are increased by 400, a fifth embodiment has been illustrated in which a secondary pipe 514 runs into the feed pipe 516.

Thus, the solution to be treated is formed, for example with a mixture of reagents, just before arrival at the thermal cycling unit 502, which is identical to that of the second embodiment. An upstream mixer is thus formed. Alternatively, or additionally, a downstream separator can be arranged by putting the outlet pipe in lateral communication with a derivation pipe.

Naturally, it will be possible to mutually combine these different embodiments, for example by adding at least one fixed temperature unit to the device in FIG. 15.

It is important to note that these various embodiments implement the protocol with an uninterrupted continuous flow solution.

Figure 18:
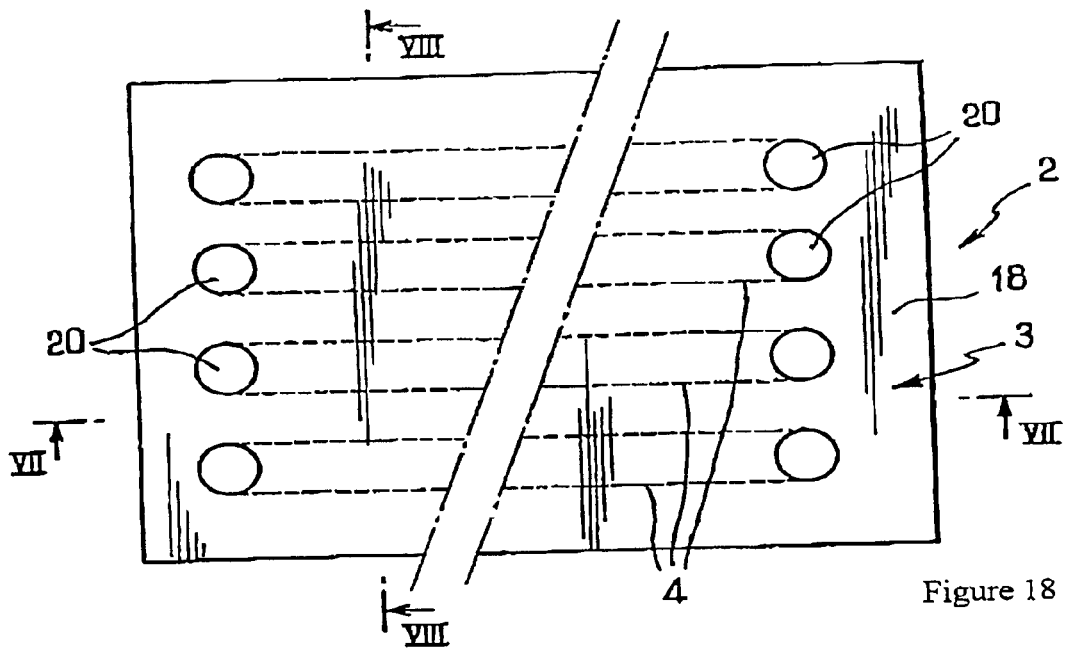
FIG. 18 is a plan view of a substrate which can be used for these five embodiments.
Figure 19:
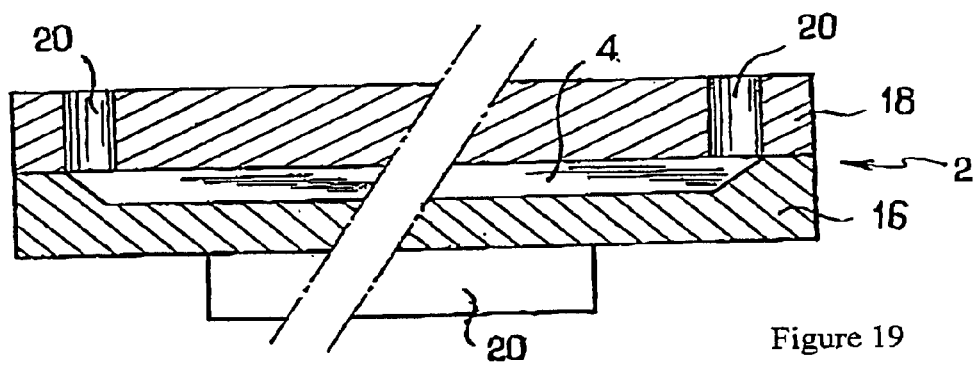
FIGS. 19 and 20 are transverse views in section along the respective planes VII—VII and VIII—VIII of FIG. 18.
Figure 20:
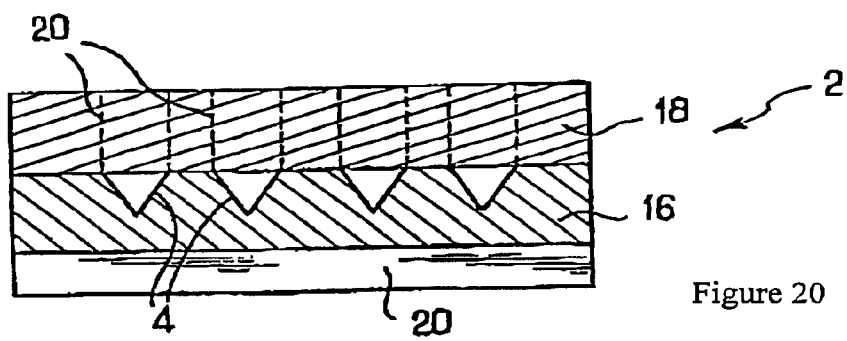

FIGS. 18 to 20 show, in detail, a thermal cycling unit 2 with several channels 4 which can be used in the embodiments presented. The substrate 3 comprises herein a silicon substrate 16, but this plate might be made of another material, for example glass, quartz, polymer material or plastic. Channels 4 are prepared by chemical etching of microgrooves (in a manner known per se) in an upper face of the substrate. Each channel 4 is rectilinear and has an isosceles triangle (or "V") profile in which one side extends in the plane of the face of the substrate. A sloped ramp connects the bottom of the channel to the face of the substrate at each end of the channel. At this stage, each channel 4 is open in the upper part of the substrate. The substrate 3 comprises a second substrate 18 having orifices 20 able to coincide with the ends of the channels. This substrate extends onto the substrate 16. It thus blocks off the upper face of the channels and provides access thereto.

The solution circulates in one of the orifices, then in the associated channel 4 and then in the other orifice. The second substrate 18 can be prepared from the same type of material as the first 16. The two plates are sealed or bonded one onto the other for example.

The channel dimensions may be any dimensions compatible with the intended use of the device. An example of channel dimensions is as follows:

channel width: 100 µm (from a few microns to a few or several hundreds of microns is also envisaged);

channel length: up to several centimeters.

The heating components 20 are positioned under the plate 16 against its lower face, which is opposite to the upper one which bears the channels. They perform the heating and the cooling of the plate in a way which is known per se, for example by Peltier effect, Joule effect, radiation or convection. The heating components may comprise the structure illustrated in FIGS. 1 and 2.

It should also be noted that it is possible to integrate the heating components 20 directly on the silicon, for example by machining heating resistors at the surface of one of the two plates 16, 18 and placing the whole thing on a cold source to evacuate the heat.

During the passing of the solution over the unit 2 the number of cycles is a function of the time spent by the solution over the unit. It is thus important to have good control over the flow rate of the solution. This control may be obtained by means of a syringe driver or by pumping (pressure force or electroosmosis for example).

The various channels of the same device can for example be used for running through solutions comprising various DNAs.

The channel may also be formed by a capillary tube, as long as the control of the temperature of the solution remains possible.

It goes without saying that the temperatures T1 to T8 will in general be different from room temperature and that the device preferably comprises in each embodiment automated means for controlling the temperature of the thermal cycling unit so as to execute the cycling.

Nucleic Acid Typing in a Continuous Flow Device

The present device may be used for conducting genotyping analyses. Genotyping a large number of DNA polymorphisms such as single nucleotide polymorphisms (SNPs), in families or in case/control groups makes it possible to find associations between certain polymorphisms or groups of polymorphisms, and certain phenotypes. In addition to sequence polymorphisms, length polymorphisms such as triplet repeats are studied to find associations between polymorphism and phenotype. Association studies linking polymorphisms with phenotypes lead to the identification of genes involved in pathologies, in responses to therapeutic products, and in other complex phenotypes. Until now, a limiting factor for association studies has been the necessity to genotype several hundreds of individuals for several thousands or tens of thousands of polymorphisms.

Forensic uses of genotyping include establishing the identity of an organism or individual from which a sample is extracted, as well as determining pedigree or parentage. Identification of polymorphisms corresponding to deletions or repeats in open reading frames can be useful for diagnosing defects associated with that polymorphism. (Winzeler et al. (Science 285: 901–906 (1999), the contents of which is incorporated herein by reference in its entirety).

Genotyping may also be used to identify an organism or strain of an organism which is responsible for an individual's disease condition. In such methods, a sample containing the nucleic acid from the organism or strain are obtained from the individual. The nucleic acid sample is genotyped to determine the identities of polymorphic sequences characteristic of different organisms or strains.

Single Nucleotide Polymorphisms (SNPs)

Approximately 80% of human DNA polymorphisms are sequence polymorphisms, while only about 20% are length polymorphisms. About 90% of sequence polymorphisms are single nucleotide polymorphisms (SNPs). Sites having three polymorphic nucleotides have also been detected. SNPs appear to be the most widely distributed genetic markers in the human genome, occurring approximately every kilobase. Since SNPs represent the most common type of DNA sequence variation, the ability to discriminate between variants of these genetic markers is a very important tool in genetic research. Many inherited diseases are the result of single point mutations at SNP sites. In some cases, the single point mutation causing nucleotide substitution in a protein-encoding gene is sufficient to actually cause the disease, as in sickle cell anemia and hemophilia. For diseases influenced by a large number of genes, including diabetes, heart disease, various cancers, and certain psychiatric disorders, SNPs are studied as markers to aid scientists in creating detailed maps of genetic variation to help find disease-linked genes.

SNP markers can be used to identify genes involved in disease or associated with any detectable phenotype by identifying the variant bases of one or more SNPs that correlate with the presence, absence, or degree of severity of the condition. DNA samples are isolated from individuals with and without the disease, and the identity of the polymorphic bases of one or more SNPs from each population are determined. The variants having a statistical association with the disease or phenotype are identified. Thereafter, samples may be taken from individuals and the variant bases of one or more SNPs associated with a disease or phenotype can be identified to determine whether the individuals are likely to develop a particular disease or phenotype, or whether they already suffer from a particular disease or possess a particular phenotype. Mapping SNP markers associated with a disease or phenotype to their chromosomal locations can identify the genes in which they occur, or indicate nearby genes having a role in the development or severity of the disease. By developing a high-density SNP map of the human genome, scientists hope to be able to pinpoint the genetic origins of diseases, the genetic differences that predispose some individuals to disease and underlie variations in individual responses to treatment and, potentially, to predict the most appropriate drugs to treat disease in individuals of a given genetic makeup.

Both the high frequency and wide distribution of SNPs in the human genome makes them a valuable source of biallelic markers for identity testing, genome mapping, and medical diagnostics. SNPs are densely spaced in the human genome, with an estimated number of more than $10^7$ sites scattered along the $3 \times 10^9$ base pairs of the human genome. Because SNPs occur at a greater frequency and with more uniform distribution than other classes of polymorphisms such as variable number of tandem repeat (VNTR) polymorphisms or restriction fragment length polymorphisms (RFLPs), there is a greater probability that SNP markers will be found in close proximity to a genetic locus of interest. SNPs are also preferred as markers because they are mutationally more stable than VNTRs, which have a high mutation rate. In addition, genome analysis using VNTRs and RFLPs is highly dependent on the method used to detect the polymorphism, while new SNPs can easily be detected by sequencing—either random sequencing to detect new SNPs or targeted sequencing to analyze known SNPs.

The different forms of a characterized SNP are easy to distinguish and can therefore be used on a routine basis for genetic typing based on polymorphisms within and between individuals. SNPs correspond to a locus where the sequence differs by a single nucleotide and has only two alleles, making SNPs suitable for highly parallel detection and automated scoring. These features offer the possibility of developing rapid, high-throughput genotyping using SNP analysis.

Devices and Processes for Genotyping in Accordance with the Present Invention

One embodiment of the present invention provides a device and processes for very large scale genotyping, where the genotyping protocol is integrated in continuous flow in a microfluidic device in accordance with the invention. The distribution of the reagents can be entirely automated and temperature cycling is integrated in the device. The microfluidic substrate constitutes a closed system, and the risks of evaporation of the reaction mixture are thus removed. Miniaturization of the reaction volumes is thus obtained, which is accompanied by reduced consumption of sample and reagent. The protocol is carried out in parallel and in series over hundreds of channels, to permit high throughput genotyping. In addition, the combination of a semi-disposable and removable microfluidic substrate with fixed external elements (fluid feed systems, thermal support) provides a reduction in costs.

In one aspect of the present invention, temperature cycling of a sample is performed by passing appropriate reagents over heating elements which cycle in temperature while the flow rate is adjusted to expose a sample to a desired number of cycles. Temperature cycling is important in numerous techniques developed for detecting or typing mutations and polymorphisms. Some genotyping techniques are based on hybridization and ligation. Strand displacement and self-sustained sequence replication are isothermal methods that can be used or modified to amplify stretches of DNA for subsequent genotyping in accordance with the present invention. Other genotyping techniques utilize PCR-based extension to determine the sequence of a stretch of DNA, or to determine the identity of a single nucleotide at a site. Ligation and PCR can also be combined, as disclosed by Barany et al. (*PCR Meth Appl* 1: 5–16, 1991).

At present, SNPs can be characterized using any of a variety of methods, any of which can be utilized in the device provided in the present invention. These methods include sequencing of the site, oligonucleotide ligation assays (OLAs), ligase/polymerase analysis, PCR—RFLP assays, Taq man PCR assays molecular beacon assays, hybridization assays with allele-specific hybridization probes, primer extension assays such as microsequencing utilising nucleotides that have been otherwise modified to aid in detection such as dideoxyribonucleoside triphosphates (ddNTPs).

Other assays can also be adapted totally or in parts to the microfluidic device such as methods based on chemical modification or protein binding, and/or cleavage of heteroduplex DNA formed with a target sample is exposed to a probe of known sequence include mismatch repair detection (MRD) using the *E. coli* methyl-directed mismatch repair system and chemical cleavage of mismatch (CCM) Methods based on DNA sequencing include both direct sequencing and UNG-mediated T-sequencing utilizing uracil N-glycosylase to remove the uracil base from DNA amplified in the presence of dUTP followed by cleavage of the molecule at the "abasic" sites created by UNG, which because it involved the "T" base on either strand allows detection of 10 out of 12 possible single nucleotide variations. (Kwok and Chen, *Genetic Engineering* 20: 125–134 (1998), the contents of which is incorporated herein by reference in its entirety).

After various reactions associated with genotyping have been performed in accordance with the present invention, sample mixtures in channels flow past a detector for determining which polymorphisms are present. The present invention thus further provides means for detection of the products of genotyping reactions. As described above, the detection zone or device may be located on or positioned to directly detect from the microfluidic substrate, or may be provided as a separate device or in a separate microfluidic substrate. Detection means may be selected from a wide range of suitable embodiments, including means for carrying out generally any enzymatic, optical, electrical, or radioactivity based detection protocol. Preferred detection methods comprise the detection of a fluorescent dye by detecting fluorescence intensity directly, by detecting the polarization of fluorescence or by detecting fluorescence resonance energy transfer (FRET).

Depending on the protocol chosen, a separation step may also be carried out. Separation steps may include electrophoretic or chromatographic separation of reaction products. As described above for detection steps, separation steps may be carried out in the microfluidic substrate, or may be carried out on a separate device or in a separate microfluidic substrate. Separation can be integrated in the device of the present invention by incorporating media suitable for a given separation purpose, systems of electrodes for electrophoretic separation or pumps for chromatographic separations. For example, media for ion-exchange chromatography, size-exclusion chromatography, or electrophoresis can be incorporated into channels or other structures of the apparatus of the present invention. Reagents and media for separation may already by embedded in channels when sample is introduced into the device via feed basin. Alternately, reagents and media for separation may be introduced later, for example they may be added to a sample mixture via reagent reservoir, downstream of amplification or sequencing reactions. Samples in continuous flow in channel can enter a medium in said channel and be separated according to the principles of the separation method chosen. Separated samples may be detected in situ in channel by a suitable method including visual detection of stained bands or detection of fluorescent bands by a fluorescence detector attached to or integrated into an embodiment of the present device; or by detection of electrical properties of the reaction products or by detection of radioactively or non-radioactively labelled reaction products. Alternately, the sample separated over a separation medium may be eluted into outlet basin 104 and samples collected for further analysis at another site.

Microsequencing in Accordance with the Present Invention

The microsequencing technique makes it possible to identify the nucleotide present at a given position in a nucleic acid. Early applications of the microsequencing technique include typing SNPs (single nucleotide polymorphisms) and detecting point mutations, but this technique can also be used for detecting more complex polymorphisms. This technique is more specific than the SNP-typing techniques which are based on hybridization, because it combines the specificity of the hybridization with the specificity of the enzymatic recognition of the nucleotide by a polymerase. The nucleotide of interest is detected by the extension of a primer with a ddNTP (blocking nucleotide base). A primer which is complementary to the region directly upstream of the nucleotide of interest is used. This primer is paired with the target nucleic acid in such a way that the 3' end of the primer is adjacent to the specific nucleotide base to be detected. This primer initiates the synthesis of the complementary strand by a polymerase in the presence of ddNTPs and allows the elongation of this primer with a single ddNTP which is the complement of the nucleotide which is present in the target nucleic acid. The incorporated ddNTP is then detected. Preferably, the ddNTPs are labelled to facilitate their detection.

For detecting a specific nucleotide, or SNP, in a sample such as genomic DNA for example, this microsequencing technique should be preceded by a step for amplifying the region which carries the polymorphism to be analysed. After the amplification reaction (in general, it is a PCR reaction); a purification of the amplification product is required to remove the excess dNTPs and the PCR primers.

After the microsequencing reaction a second purification step is often used to remove the excess labelled ddNTPs before detecting the ddNTP incorporated at the 3' end of the microsequencing primer. This latter purification generally involves a gel separation. However homogenous phase detection methods are preferred in order to avoid this later purification step. The protocol for genotyping by microsequencing is thus complex; it involves various steps which each comprise the mixing of reagents and long reaction times. The various enzymatic reactions of the protocol should be performed at specific temperatures; the PCR and the microsequencing reaction are carried out by thermal cycling.

A homogeneous phase protocol has been developed in which the PCR, the purification, the microsequencing reaction and the detection are carried out in solution in the well of a microplate (Chen et al., *Proc. Natl. Acad. Sci. USA*, 1a, 94/20: 10756–10761, (1997), the contents of which is incorporated herein by reference in its entirety). In this homogeneous phase protocol the incorporated ddNTP is detected by fluorescence by energy transfer. The microsequencing primer is therefore labelled. Despite the integration of all the steps in a microplate, this method does not allow very large scale genotyping. Specifically, the successive addition of the reagents in the microplate imposes a very large number of distributions at each step of the protocol. These distributions can be automated with the aid of a dispensing robot, but the distributions are then extremely slow and the risks of evaporation become considerable. The reaction volumes thus remain sizeable (10–100 $\mu$l), which involves a considerable consumption of sample which is often available in minute quantities and of reagents which are often very costly. In addition, a manipulation of the microplates even in a highly automated fashion is impossible at such a high throughput.

Figure 21:
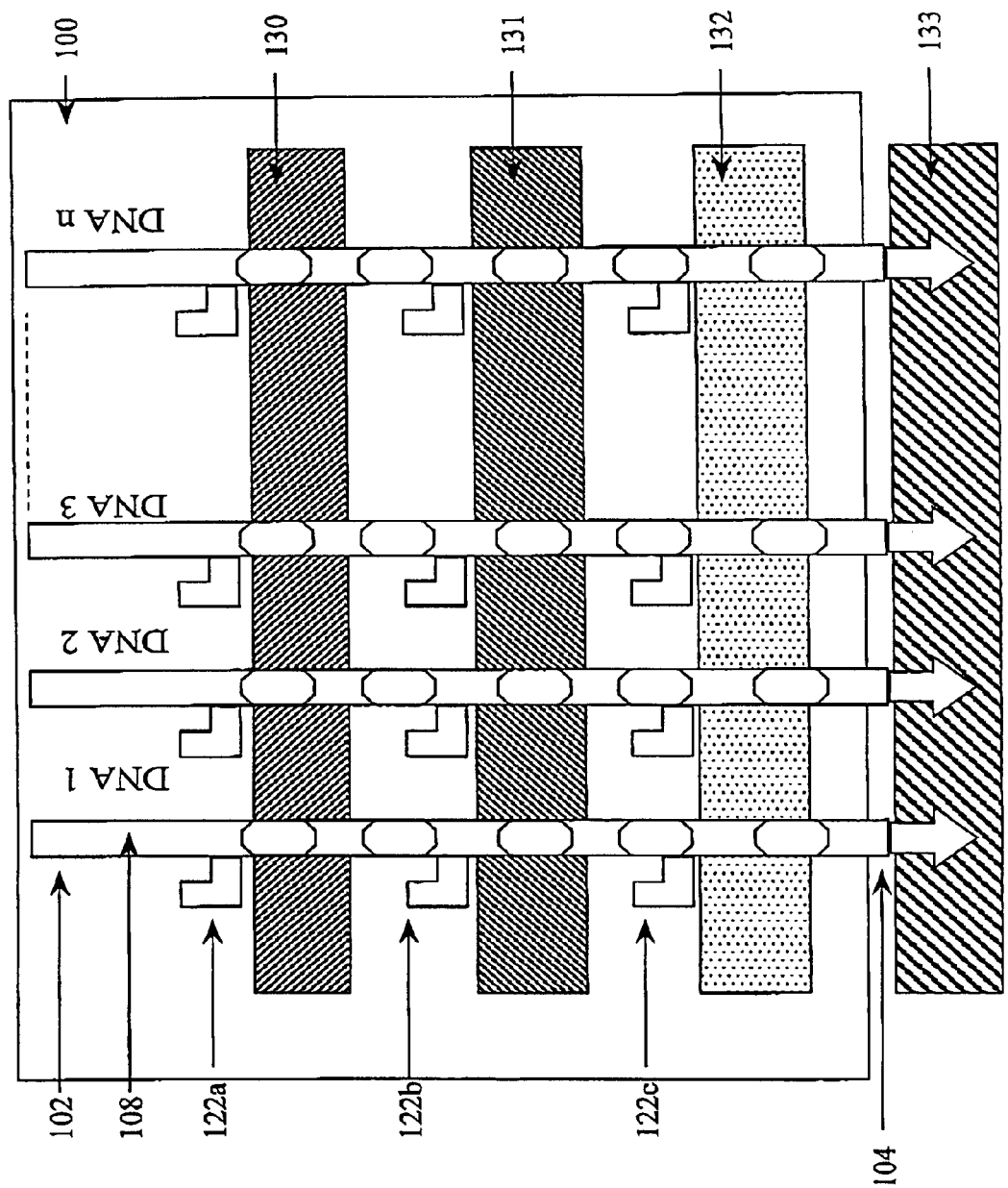
FIG. 21 is a an overview of a genotyping protocol to be carried out on a microfluidic substrate.

FIG. 21 describes a general scheme for a specific exemplary genotyping protocol which can be carried out in accordance with the present invention. FIG. 21 shows a representation of a microfluidics substrate 100 for integrated genotyping in continuous flow. In this protocol, DNA samples to be typed are injected into an inlet basin 102 feeding a channel 108, with continuous flow proceeding in the direction indicated by the arrows. As shown in the Figure, each channel 1 to n receives sequential injections of a given DNA sample such that each channel only contains a single sample of DNA. DNAs 1 to n are thus run in parallel. PCR reagents are injected through reagent basins or reservoirs 122a. A different PCR reagent is injected for each sequential DNA sample in a channel, but this PCR reagent is injected across all channels 1 to n in parallel at the same time. The samples mixed with the PCR reagents cross a PCR zone 130, where a thermal support cycles the temperature of the samples to carry out the PCR reaction. Purification reagents, preferably enzymes, are injected into reagent basins or reservoirs 122b. The same purification reagent is injected both sequentially and in parallel for all DNAs. The purification reaction mix then cross a purification zone 131, where a thermal support brings the samples to a first temperature for the purification reaction and a second temperature for inactivation of the purification enzymes. Microsequencing reagents are then injected into reagent basins or reservoirs 122c. The microsequencing reaction mix then crosses a microsequencing zone 132, where a thermal support cycles the temperature of the reaction solution to carry out the microsequencing reaction. As with PCR reagents, a different microsequencing reagent is injected for each sequential DNA sample in a channel, and each microsequencing reagent is injected across all channels 1 to n in parallel at the same time. The completed reaction then proceeds through outlet basin 104, and continue to a detection zone 133, where the identity of the nucleotide base incorporated into the microsequencing primers is determined by a detection device. Optionally, the detection zone can be located on the substrate 100.

Figure 22:
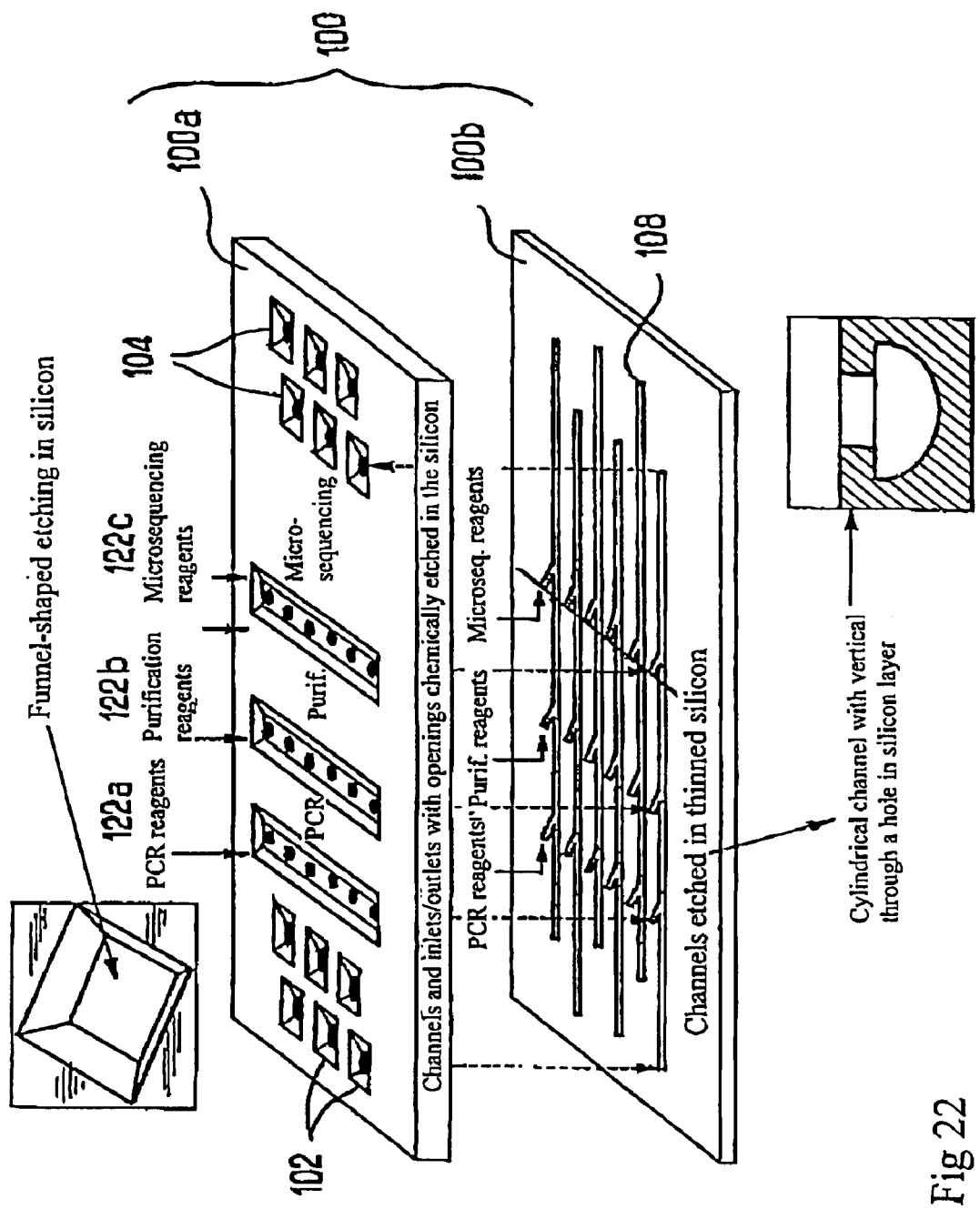
FIG. 22 is a perspective exploded view of the microfluidic substrate.

FIG. 22 describes a particular embodiment in which genotyping is carried out in accordance with the present invention. FIG. 22 shows a section of a microfluidic substrate 100 for integrated genotyping in continuous flow. Inlet basins 102 and outlet basins 104 are represented in this figure. Internal channels 108 arranged in parallel connect a feed basin and an outlet basin respectively. The feed basins and the outlet basins are essentially formed by a through-opening made in a substrate 100a. The channels 108 are in the form of grooves etched in a substrate 100b. The figure also represents reagent reservoirs 122a, 122b, 122c constructed between the feed basins 102 and the outlet basins 104. Connectors make it possible to connect each of the reagent reservoirs to all of the channels 108. It is observed that the microfluidic substrate comprises a plurality of channels in parallel. Typically, at least 100 channels are arranged in parallel.

Although not represented in the figure, the feed basins and the reservoirs are respectively associated with fluid feed systems for continuously feeding the channels with samples and for distributing the reagents.

The thermal support onto which the microfluidic substrate is added is not represented. This thermal support comprises several temperature regulated zones, including zones which can be cycled. These temperature regulated zones coincide with the sections of the channels 108 which are positioned between the reagent reservoirs 122a and 122b, as well as with the sections of the channels 108 which are positioned between the reagent reservoir 122c and the outlet basins 104.

The device in accordance with the invention also comprises a detection system in the outlet basins. The detection is performed in parallel and in series on all the channels 108. Alternatively, the detection is not performed in the outlet basins, but slightly upstream, at the outlet of the final temperature regulated zone. In this case, a plate of transparent material (glass, quartz or a plastic for example) can locally replace the substrate 100a, to directly detect the samples running through the channel.

Particularly advantageously, the injection of the samples and of the reagents, the regulation of the reaction temperatures and of the temperature cycles, as well as the detection are entirely automated.

The samples are injected in continuous flow into the channels 108 via the feed basins 102. Preferably, the same DNA is injected in series into a channel 108, the DNA injections being separated from each other by "separators" of an inert, optionally non-miscible fluid. The injections are synchronous over all the channels 108 arranged in parallel. The samples injected at a time t run through the channels synchronously, in such a way that the injections of reagents and the detection are performed simultaneously in parallel over all the channels.

The PCR reagents are injected in parallel into all the channels in the reagent reservoir 122a. The same reagent is injected at one time and into all the channels in parallel. On the other hand, with the aim of typing the same DNA for 100 polymorphic sites, 100 different reagents are injected in series into a given channel. Given that 100 channels are arranged in parallel on the microfluidic substrate, 100 DNAs are typed in parallel on the same substrate. The injections into the same channel are separated from each other by injections of "separators".

The reaction mixture then runs through a temperature regulated zone which can be cycled, where the amplification reaction is performed. It should be noted that the channel is rectilinear and that the reaction mixture runs through only one heat zone. The advantages of this specific arrangement according to the invention are described above. It should also be observed that given the characteristics of the PCR reaction, the cycle temperature of the temperature regulated zone at the moment when a fraction of the sample enters this zone, is of little importance. Finally, it should be observed that this arrangement makes it possible to vary, at will, the number of thermal cycles performed (typically between 15 and 40 cycles for one PCR) by regulating the cycling times and the flow rate of the solution running through the channel.

The second step of the protocol, the PCR-product purification reaction, begins with the injection of the purification reagent into the reservoir 122b. The same reagent is injected in parallel and in series into all the channels 108.

The reaction mixture then runs through a first zone which is temperature regulated at 37° C. for the purification reaction, and a zone which is temperature regulated at 94° C. for the inactivation of the purification enzymes.

The microsequencing reaction begins with the injection of the microsequencing reagents. As previously for the PCR reagents, a different reagent is used for typing each polymorphism. For typing 100 polymorphisms, 100 different reagents are injected in series into the same channel 108.

The reaction mixture then runs through a second temperature regulated zone which can be cycled, where the microsequencing reaction is performed.

At the outlet of this temperature regulated zone the detection is performed, in continuous flow, in parallel and in series, of the ddNTPs which are incorporated at the 3' end of the microsequencing primer. Typically, the ddNTPs are labelled with fluorophores.

The detection is performed in solution by measuring the fluorescence, polarised fluorescence, or the temporal correlation of fluorescence, or by spectropolarimetry. Moreover, these detection means are known.

An example of an integrated protocol for amplification by PCR and microsequencing in a microfluidic substrate according to the invention is provided in Example 2.

Genotyping by the Method of Allele-Specific Ligase Chain Reaction (LCR)

High-resolution genotyping can be carried out in accordance with the present invention, using thermostable ligase in the allele-specific ligase chain reaction (allele-specific LCR). (Barany et al. (*PCR Meth. Appl.* 1: 5–16 (1991), the contents of which is incorporated herein by reference in its entirety). Allele-specific LCR employs four oligonucleotides two of which hybridize to one strand of target DNA and a complementary set of adjacent oligonucleotides, which hybridize to the opposite strand. Thermostable DNA ligase will covalently link each set, provided there is complete complementarity at the junction. Oligonucleotide products from one round of hybridization and ligation may serve as substrates during the next round, permitting exponential amplification of oligonucleotides analogous to PCR amplification. A single-base mismatch at the oligonucleotide junction will not be amplified and is therefore distinguished; a second set of mutant-specific oligonucleotides is used in a separate reaction to detect or confirm the mutant allele(s).

Detection and analysis of the products of the allele-specific ligation are carried out in accordance with the present invention. In preferred embodiments, said products are detected directly from the reaction product flowing in or from the microfluidic substrate, without an additional separation step, such as by measuring fluorescence resonance energy transfer, or polarized fluorescence. In other embodiments of the present invention, the ligation products are analyzed by passing the reaction mixture through a separation medium contained in a region of the device or in another device connected to the microfluidic device and detecting the elution of ligated and unligated oligonucleotides from the separation medium. In another embodiment, the reaction mixture is introduced by continuous flow into a medium for electrophoretic separation preferably located in a device connected to the microfluidic device, electrophoresis is performed, and the products are detected by their position within the medium or by the order of their elution from the medium. In yet another embodiment, the reaction mixture moves by continuous flow into a collection chamber from which it is removed and analyzed.

In one embodiment of the present invention using the ligase chain reaction, sample is introduced into a feed basin 102, and is distributed to a channel 108. Reagents for the ligase chain reaction, containing the oligonucleotides specific for one allele, are introduced into reagent reservoir 122a and mixed with the sample flowing through channel 108, and thereafter flow into a separation medium located at the distal end of channel 108. A separation procedure is performed and samples are collected as they elute into outlet basin 104. In this embodiment, a second, identical sample is then introduced into feed basin 102 and into channel 108, separated by "separators" from the previous sample; reagents for the ligase chain reaction, containing the oligonucleotides specific for another allele are introduced into reagent reservoir 122a and mixed with the second sample and the procedure is performed as described above. Example 3 below describes the use of devices of the present invention for genotyping by LCR.

PCR Based Genotyping Methods: the TaqMan™ Method

Preferentially for diagnostics applications, the present invention may also be used with the TaqMan™ (PE Applied Biosystems) method of determining the identity of a nucleotide base. The TaqMan™ PCR system provides for the detection of PCR products without further processing for detection, by monitoring the increase of fluorescence of a dye-labelled DNA probe. The TaqMan™ PCR system is a homogeneous phase detection system.

The method is based on a target specific probe which exploits the 5'–3' exonuclease activity of DNA polymerase (Holland et al., PNAS USA 88: 7276–7280 (1991); Lawyer et al., J. Biol. Chem. 264: 6427–6437 (1989) the disclosures of which are incorporated herein by reference in their entireties) to allow detection of PCR product by the release of a fluorescent reporter (Holland et al. (1991); Lee et al., Nuc. Acid. Res. 21: 3761–3766 (1993) the disclosures of which are incorporated herein by reference in their entireties) during the PCR. The probe consists of an oligonucleotide labelled with a 5' reporter dye (eg. FAM, TET, JOE, HEX) and a 3' quencher dye (TAMRA) generally attached via a linker arm. When the probe is intact, the proximity of the reporter dye to the quencher dye results in suppression of the reporter fluorescence. During PCR, if the target of interest is present, the probe specifically anneals between the forward and reverse primer sites. The 5'–3' nucleolytic activity of the polymerase (AmpliTaq Gold™) cleaves the probe between the reporter and the quencher only if the probe hybridizes to the target. The polymerase does not digest free probe. The probe is then displaced from the target and the polymerization of the strand continues. This process occurs in every cycle and does not interfere with the exponential accumulation of the the PCR product. The separation of the reporter dye from the quencher dye results in an increase of fluorescence emission from the reporter, which can be measured and is a direct consequence of target amplification during PCR. The TaqMan™ system is further described in *TaqMan™ PCR Reagent Kit Protocol*, PE Applied Biosystems (1996).

Any suitable device for the detection of reporter fluorescence can be used to monitor the increase in reporter fluorescence. In one embodiment, a device such as the ABI Prism Sequence Detection System (PE Applied Biosystems) is used. In other embodiments, a detection device is integrated into the microfluidic device of the invention, or is integrated into a further microfluidic substrate operably linked to the microfluidic substrate of the invention.

In one embodiment of the present invention using the TaqMan™ PCR system, sample is introduced into a feed basin 102, and is distributed to a channel 108. Reagents for the TaqMan™ PCR reaction, containing the oligonucleotides specific for an allele, are introduced into reagent reservoir 122a and mixed with the sample flowing through channel 108, and thereafter flow into a detection zone located at the distal end of channel 108. A fluorescence detection step is performed and samples are collected as they elute into outlet basin 104. Alternatively, and samples are collected as they flow into outlet basin 104, and a fluorescence detection step is performed upon flowing terminated reactions in another or preferably an operably linked detection device. In this embodiment, a second, identical sample is then introduced into feed basin 102 and into channel 108, separated by "separators" from the previous sample; reagents for TaqMan™ PCR reaction, containing the oligonucleotides specific for another allele, or another polymorphic site or specific sequence are introduced into reagent reservoir 122a and mixed with the second aliquot of the sample and the procedure is performed as described above. Example 5 below describes the use of devices of the present invention for genotyping by TaqMan™ PCR.

PCR Based Genotyping Methods: Molecular Beacons

Preferentially for diagnostics applications, the present invention may also be used with molecular beacons to determine the identity of a nucleotide base.

Molecular beacons are oligonucleotide probes that can report the presence of specific nucleic acids in homogenous solutions (Tyagi and Kramer, Nature Biotech. 14: 303–308 (1996); Tyagi, S., et al. Nature Biotech. 16: 49–53 (1998)). These beacons are hairpin shaped molecules with an internally quenched fluorophore whose fluorescence is restored when they bind to a target nucleic acid. They are designed in such a way that the loop portion of the molecule is a probe sequence complementary to a target nucleic acid molecule. The stem is formed by the annealing of the complementary arm sequences on the ends of the probe sequence. A fluorescent reporter dye (eg. FAM, TET, JOE, HEX) is attached to the end of one arm (5' or 3') and a quencher dye (TAMRA, DABCYL) to the end of the other arm. When the stem keeps the two dyes in close proximity, the proximity of the reporter dye to the quencher dye results in suppression of the reporter fluorescence. When the probe encounters a target molecule, it forms a hybrid that is longer and more stable than the stem, and its length and rigidity preclude the simultaneous existence of the stem hybrid. When the molecular beacon undergoes this conformation change that forces the stem apart, the reporter dye and the quencher dye move away from each other and fluorescence is restored. A wide variety of fluorophores can be used to detect multiple target nucleotides; additionally, DABCYL, a non-fluorescent chromophore can be used as a universal quencher for many different fluorophores. Molecular beacon methods are further described in Tyagi et al. protocol for Molecular Beacons: hybridization probes for detectin ofo nucleic acid in homogenous solutions, Department of Molecular Genetics, New York University (1997).

Molecular beacons are designed such that (a) the nucleotide sequence of the probe is compementary to a target sequence or to the sequence containing a target nucleotide, (b) the length of their arm sequences allows a stem to be formed at the annealing temperature of a PCR reaction, and (c) the length of the loop sequence allows the probe-target hybrid to be stable at the annealing temperature. This can be determined by obtaining thermal denaturation profiles. Beacons are included with the PCR primers in the PCR reaction. Beacons fluoresce both during the denaturation step and at the annealing temperature, but not during the lowering of the temperature from the denaturation step to the annealing temperature, and not during the primer extension steps, since the beacons dissociate from the template at the primer extension temperature.

Two allele-specific molecular beacons, each labeled with a different fluorophore, are included in the genotyping reaction, thus allowing one to distinguish between homozygotes and heterozygotes. For example, the molecular beacon specific to the wild-type allele is labeled with a fluorophore (eg tetrachlorofluorescein (TET)), and the molecular beacon specific to the mutant allele is labeled with the another fluorophore 6carboxyfluorescein (FAM). DABCYL is used as the quencher on both molecular beacons. By using two different molecular beacons in each PCR reaction, three possible allelic combinations (genotypes) of two sequence variants can be distinguished simultaneously by the type of fluorescence detected: TET fluorescence indicates homozygosity for the wild-type allele, FAM fluorescence indicates homozygosity for the mutant allele, and both TET and FAM fluorescence together indicates heterozygosity.

The fluorescence can be measured upon collecting samples from the channel after the PCR reaction. In certain embodiments, fluorescence can be monitored in real time, preferably at annealing temperature. Any suitable device for the detection of reported fluorescence can be used to monitor the increase in reporter fluorescence. In one embodiment, a device such as the ABI Prism Sequence Detection Systen (PE Applied Biosystems) is used. In other embodiments, a detection device is integrated into the microfluidic device of the invention, or is integrated into a further microfluidic substrate operably linked to the microfluidic substrate of the invention. Example 6 below describes the use of devices of the present invention for genotyping using molecular beacons.

PCR-Sequence-Specific Primers (SSP)

Genotyping may be carried out in accordance with the present invention using the method of sequence-specific primers (PCR-SSP) (Metcalfe et al., Vox Sang 77: 40–43 (1999), the contents of which is incorporated herein by reference in its entirety) also called allele-specific PCR (AS-PCR), a competitive multiplex PCR method using parallel reactions in which PCR amplification can be successfully performed only by using the primers whose 3' ends are an exact match to an allele. Sohda (J. Clin. Lab Anal. 13: 205–208 (1999), the contents of which is incorporated herein by reference in its entirety).

Sample Preparation for Somatic Cells Genotyping: RT-PCR

The present invention provides a device and processes for genotyping a sample using reverse-transcriptase and nested PCR of expressed sequences (RT-nested PCR), followed by cycle sequencing (Happ et al., Vet. Immunol. Immunopathol. 69: 93–100 (1999), the contents of which is incorporated herein by reference in its entirety) which provides a degenerate PCR technique that can be used as a first step to identify and amplify the actual sequence when it is not completely known. Harwood et al. (J. Clin. Microbiol. 37: 3545–3555 (1999), the contents of which is incorporated herein by reference in its entirety). In one embodiment, amplification templates are produced by performing reverse-transcriptase PCR (RT-PCR) on total RNA. In one embodiment, the RT-PCR reaction is performed in a channel of the device, and reagents for subsequent reactions are added directly to the mixture in the device; alternately, RT-PCR may be performed outside the device, and an aliquot introduced into the device of the present invention.

Identifying Polymorphic Sites using Arbitrarily Primed PCR (AP-PCR)

The present invention provides a device and processes for performing arbitrarily primed PCR (AP-PCR), which is often useful as a preliminary step to find potential polymorphisms. Jonas et al. (J. Clin. Microbiol. 38: 2284–2291 (2000), the contents of which is incorporated herein by reference in its entirety). In this method, a primer is allowed to anneal to genomic DNA under conditions of low stringency, for example a cycle of 60 seconds at 36° C. After extension and amplification cycles, PCR products are sequenced to detect polymorphisms. Example 4 describes the use of the devices of the present invention to identify polymorphisms using AP-PCR.

Genotyping by the Methods of AFLP and fAFLP

In yet another embodiment, the present invention provides a device and processes for genotyping to be carried out in accordance with the present invention using AFLP (amplified fragment length polymorphism) fingerprinting. AFLP produces a distinctive DNA fingerprint by selective PCR amplification of restriction fragments from an entire genome. The AFLP fingerprint is generated by digesting chromosomal DNA with two different DNA restriction endonucleases, ligating adaptors to the sticky ends and amplifying the fragments with primers complementary to the adaptors. The present invention may also be a modification known as fAFLP (fluorescent amplified fragment length polymorphism) described in detail in the Examples below (Hookey et al., J. Microbiol. Meth. 37: 7–15 (1999); Goulding et al., J. Clin. Microbiol. 38: 1121–1126 (2000), the contents of which are incorporated herein by reference in their entirety).

To practice fAFLP in accordance with the present invention, a sample is introduced into feed basin 102, from whence it flows into a plurality of channels 108. Restriction enzymes and other reagents for digestion are introduced into reservoir 122a and mixed with sample. Alternatively, pre-digested DNA may be introduced into feed basin 102. Reagents for a ligation of digested DNA to adapters are introduced into reservoir 122b. Reagents for the amplification step, including fluorescent dye 5/6-FAM, are introduced into reagent reservoir 122c and mixed with the sample that has previously been digested and ligated to adapters. Following the amplification step, samples may be collected in outlet basin 104 and removed for analysis; alternately, a second device enabling electrophoretic separation can be connected to the microfluidic substrate of the presnt invention.

Genotyping using a Universal Heteroduplex Generator (UHG)

The present invention provides a device and processes for genotyping using a synthetic molecule called a universal heteroduplex generator (UHG) as a hybridization probe for PCR products. The UHG is an amplifiable copy of the target sequence containing strategic sequence modifications in close proximity to the mutation point. The UHG is mixed, denatured and reannealed with the amplicon containing the target sequence. Chromatographic or electrophoretic separation of homoduplexes and heteroduplexes is used to separate and identify homoduplexes formed by complementary strands of the same allele and heteroduplexes formed between the complementary regions of two distinct alleles (Bolla et al., J. Lipid Res. 40: 2340–2345 (2000), the contents of which is incorporated herein by reference in its entirety). The UHG is constructed by synthesis, fusion and subsequent amplification of four overlapping nucleotides for a significant number of cycles, for example 30 cycles of: 94° C. for 1 min; 57° C. for 1 min; 72° C. for 1 min. Genomic DNA to be probed with the UHG is likewise amplified by PCR methods. The UHG may be created in accordance with the device and processes of the present invention, where the sample mixture in continuous flow through channels 108 passes through temperature regulated zones where it undergoes thermal cycling. Alternately, the UHG may be previously constructed and added to an amplified DNA sample in channels 108 via reagent reservoir 122a or 122b or 122c.

Other Chemical, Biochemical and Biological Processes in Accordance with the Present Invention The present invention provides a device and processes for advantageously practicing novel methods for biochemical and biological analysis. Advantageous aspects of the present invention include, but are not limited to, the aspect of precise control of temperature in temperature regulated zones, the thermal cycling aspect of the present invention, comprising at least two different temperatures, the continuous flow aspect of the present invention, the ability to add reactants to a sample as it flows through the device, the ability to remove aliquots from a sample as it flows through the device, and the ability to integrate reaction, separation, and detection in channels 108 of the device of the present invention.

The present invention may generally be used advantageously for applications in the fields of proteomics, analysis of polysaccharides, synthesis of fine chemicals, polymer synthesis and drug screening. Such applications which deal with expensive or rare samples are carried out advantageously in a system of the invention which can provide small sample volume, a closed system preventing evaporation of sample, and high throughput.

Proteomics

Until recently, the sequence analysis of proteins in tissues, cells and biological fluids was a laborious exercise, in marked contrast with the sequence and expression analysis of genes (genomics), which for several years has been a rapid, automated process. Proteomics has the potential to enable proteins to be analyzed in a similar high throughput, automated fashion, having major implications for pharmaceutical research and development.

There is now a rapidly growing awareness of just how important proteomics is to understand and organise the human genome and so accelerate the discovery of medically important proteins and the genes from which they derive. By comparison of disease and control samples, it is possible to identify "disease specific proteins". These may have potential as targets for drug development or as molecular markers of disease.

Most disease processes are manifested not at the level of genes, but at the protein level, and there may be a poor correlation between the level of activity of different genes and the relative abundance of the corresponding proteins. Also, a protein and its post-translational modifications are not directly encoded for by the same gene, therefore the complete structure of individual proteins cannot be determined by reference to the gene alone. There is thus a need to analzye and manipulate proteins, particularly at high throughput or in large numbers of analyses in the field of proteomics.

Proteomics involves the separation, identification and characterization of proteins present in a biological sample. In one application, a protein signature can be obtained, by subjecting glycoproteins, preferably rare glycoproteins, to a tryptic digest in the microfluidic substrate, and peptides can be analysed in the microfluidic device or in a separate analysis device, such as an electrophoresis or chromatography device. Optionally, the peptides are derivatized in the microfluidic substrate with a detectable moiety for a subsequent detection step. In another application, oligosaccharides are cleaved from a glycoprotein in a channel and analysed either in an analysis zone of the microfluidic substrate or flow to another device.

Characterization of Post-Translational Modifications of Proteins

For instance, in accordance with the methods and device of the invention, it is possible to characterize the post-translational modification of proteins by elucidating a combination of the structural and positional (position on the protein) characteristics of an oligosaccharide on a protein. For example, proteins from cells are separated by 2D-gel electrophoresis. A given glycoprotein is transferred from a gel into a solution and introduc into a channel of the microfluidic substrate. Since the substrate has channels in parallel, many different proteins can be injected in parellel, and/or in series. An enzyme that cleaves oligosaccharides from a glycoprotein is introduced to the channel thorough a reagent basin or reservoir. The first glycoprotein sample moves to the first temperature regulated zone (37° C.) and flows through said temperature regulated zone for a given time, during which the oligosaccharides are realeased from the glycoprotein. While still in said first temperature regulated zone, the temperature of this temperature regulated zone is changed with a rapid transition from 37° C. (an optimal temperature for enzyme activity) to, e.g., 94° C. (for 10 minutes) to inactivate the enzyme. The first glycoprotein sample exits the first temperature regulated zone, the temperature of this first temperature regulated zone is rapidly changed to 37° C. and the second glycoprotein sample enters the first temperature regulated zone. Thus the first temperature regulated zone is cycling between 37° C., where enzymatic cleavage of polysaccharides or proteins occurs, and 94° C., where inactivation of enzymes-occurs. After the oligosaccharides are released from a glycoprotein, 1 $\mu$l of a mixture of a fluorescent dye (e.g., amino-pyrene three sulfonic acid (APTS) 20 mM) and $NaCNBH_3$ (0.4M) are added to the sample. The mixture enters a second temperature regulated zone that is equilibrated at 94° C. The sample moves through the second temperature regulated zone during a time period of 1 hour. The oligosaccharides from a glycoprotein are labeled by the fluorescence dye in the second temperature regulated zone. Finally, the sample is either collected and analyzed off-line by capillary electrophoresis with laser induced fluorescence detection and MALDI/TOF mass spectrometry, or it is injected into an electrophoretic microfluidic device that is integrated with the microfludic device used for the temperature treatment, and analyzed on-line.

Tryptic Digest

In another example, proteins from cells are separated by 2D-gel electrophoresis. A given glycoprotein is transferred from a gel into a solution and introduced into a channel of the microfluidic substrate. Since this substrate has channels in parallel many different proteins can be injected in parellel, and in series. An enzyme (e.g., pepsin, trypsin) is introduced to the channel via a first reagent feed basin or reservoir. The first sample enters into a first temperature regulated zone (37° C.) and it flows through this first temperature regulated for a given time, during which the proteins are cleaved and peptide molecules are formed. While still in the first temperature regulated zone, the temperature of this temperature regulated zone is transitioned rapidly from 37° C. (an optimal temperature for the enzyme) to, e.g., 94° C. (10 minutes) to inactivate the enzyme. Upon exit of the first sample from the first temperature regulated zone, the temperature of the first temperature regulated zone is rapidly changed to 37° C. and the second sample enters the first temperature regulated zone. Thus the first temperature regulated zone is cycling between 37° C., where enzymatic cleavage of polysaccharides or proteins occurs, and 94° C., where the inactivation of enzymes occurs. Optionally, more than one means of chemical or enymatic cleavage is used for different oligosaccharides (eg. O-linked and N-linked oligosaccharides), and additional temperature treatment steps may be included in a cycle to allow the optimization for different cleavage means. The peptide chains are fluorescently labeled with amino-sensitive fluorescent dyes (Molecular Probes) in the second temperature regulated zone. Finally, the sample is either collected and analyzed off-line by capillary electrophoresis with laser induced fluorescence detection or is introduced into an electrophoretisis microfluidic device that is integrated with the microfludic device or substrate used for the temperature treatment, and analyzed on-line. The peptides can also be spotted onto a metal plate just after they exit the first temperature regulated zone and analyze off-line by mass spectrometry (e.g., MALDI/TOF), or they can be directly electrosprayed to a mass spectrometer.

Structural Characterization of Complex Polysaccharides Mixtures (e.g. Hyaluronic Acid)

The microfluidic device of the invention may also be used for the stuctural characterization of complex polysaccharides. Polysaccharides are highly diverse and complex mixtures with distributions in molecular weight, degree of polymerization, sequence, branching and type of monosaccharide units, and their linkage (Yalpani, M. Polysaccharides: Synthesis, Modifications and Structure/Property Relations; Elsevier, Amsterdam, 1988). Due to the increasingly recognized importance of different polysaccharides in biological processes and industrial applications, there is a need to relate physical properties of these polymers to their structural attributes. It is now commonly perceived that the bulk measurements on such materials are often inadequate as the means of characterization. Modern separation techniques are being increasingly applied in characterization of polysaccharides, e.g., combination of size-exclusion chromatography with low-angle scattering (Jeng, et al., J. Appl. Polym. Sci. 49: 1359–1374 (1993)), ion-exchange chromatography with pulsed amperometric detection (Koizumi, et al., J. Chromatogr. 464: 365–373 (1989)), or capillary electrophoresis with laser-induced fluorescence detection (Stefansson and Novotny, Anal. Chem. 66: 1134–1140 (1994)); Sudor and Novotny, Anal. Chem. 67, 4205–4209 (1995) the disclosures of which are incorporated herein by reference in their entireties). In certain applications (e.g., when oligosaccharides cleaved from rare glycoprotein are characterized; Mechref et al., Glycobiology 9: 227–234 (1999)) there is a need to minimize the amount of samples used. Thus, a miniaturized integrated device providing a means of peforming chemical reactions for sample preparations and a subsequent means for sample characterization and detection would be advantageous in the characterization of poly- or oligosaccharide.

Elucidation of Hyaluronic Acid Structure

Hyaluronic acid (HA) is a linear polysaccharide with specific functions in assisting proteoglycan aggregation in numerous connective tissues. HA has also important roles in cellular regulation (Alho and Underhill, J. Cell Biol. 108: 1557–1565 (1989)) and cell protection (Underhill, and Toole, J. Cell. Physiol. 110: 123–128 (1982) the disclosures of which are incorporated herein by reference in their entireties). HA is also finding industrial and medical applications in ophtalmology, clinical diagnosis, drug delivery and cosmetic preparations.

The buffered solution of hyaluronic acid (10 mg/ml) and hyaluronidase (3 mg/ml) is introduced into a channel of the microfluidic substrate of the invention in parallel and in series. The volume of each reaction is about 1 $\mu$l. A first sample, or reaction, is moved to a first temperature regulated zone that is equilibrated at 37° C. The degree of enzymatic cleavage of the polysaccharide is specified by selecting the period of time during which the first sample flows through the first temperature regulated zone. After passing the first temperature regulated zone, the first sample enters second temperature regulated zone (94° C.) where hyaluronidase is inactivated. Alternatively, the first sample flows to the first temperature regulated zone at 37° C. and, while the sample is still in the first temperature regulated zone, the temperature of this first temperature regulated zone is transitioned rapidly from 37° C., the temperature where enzyme activity is optimal, to, e.g., 94° C. (for 10 minutes), to inactivate the enzyme. The first sample exits the first temperature regulated zone, the temperature of this zone is rapidly transitioned to 37° C. and a second sample enters the first temperature regulated zone. Optionally, the time during which the first temperature regulated zone is kept at 37° C. for the second or a subsequent sample is different from the time for the first sample. Varying the time of giving a possibility to study enzyme kinetics on-line; noting, this picture will be the same for digesting proteins and getting peptide maps). Thus the first temperature regulated zone is cycling between 37° C. (enzymatic cleavage of polysaccharides or proteins) and 94° C. (inactivation of enzymes). After the hyaluronic acid is enzymatically cleaved in the first temperature regulated zone, 1 $\mu$l of a mixture of a fluorescent dye (e.g., amino-pyrene three sulfonic acid (APTS) 20 mM) and NaCNBH$_3$ (0.4M) are added to the sample. The mixture enters a second (or a third) temperature regulated zone that is equilibrated at 94° C. The sample moves through the second temperature regulated zone during a time period of 1 hour. The oligosaccharides of hyaluronic acid are labeled by the fluorescence dye in the second temperature regulated zone. Finally, the sample is either collected and analyzed off-line by capillary electrophoresis with laser induced fluorescence detection and size-exclusion chromatography with light scattering detection or is injected into electrophoretic chip that is integrated with the thermal chip and analyzed on-line.

In other aspects, the microfluidic device of the present invention may be used generally to carry out the derivation of a glycoprotein, or peptide. For example, labelling of peptides or oligosaccharides can be carried out by injecting labelling reagents and subjecting the sample and labelling reagents to a predetermined temperature in a temperature regulated zone to allow the linking of the label to the peptides or oligosaccharides.

The present invention may be used in protocols where it is desired to sequentially activate and inactivate an enzyme. For example, it is well known that the enzyme ribonuclease loses activity upon heating but quickly regains it upon cooling, indicating the unfolded ribonuclease polypeptide snaps back into a native conformation upon cooling. (Stryer, *Biochemistry*, pg. 197 (1975), the contents of which is incorporated herein by reference in its entirety). Thermal cycling of a reaction containing ribonuclease would permit controlled transitions between the enzyme in an active state and in an inactive state. This aspect may be exploited to enhance substrate diffusion or prevent feedback inhibition; alternately, this aspect may be exploited to permit additional or novel substrate to be added. In one embodiment, a sample is introduced into a plurality of channels 108 via feed basin 102, and reagents including ribonuclease are added via reagent reservoir 122*a*. The sample moves through channels 108 to a zone of higher temperature in which ribonuclease is unfolded and inactive; at that point, additional substrate, or a new substrate, is added via reagent reservoir 122*b*. Alternately, aliquots of the reaction mixture may be removed via reservoir 122*b*, as the temporary quenching of ribonuclease active provides a means for determining an end-point. As the sample moves through channels 108 to a zone of lower temperature, ribonuclease refolds to its active configuration and begins to carry out reactions using the substrates added. Reaction products are collected in outlet basin and analyzed.

The present invention may be used inprotocols in which it is desired to regulate the rate, character, or direction of a chemical or biochemical reaction. This embodiment of the present invention exploits the fact that different reactions catalyzed by the same enzyme or inorganic catalyst may have different thermodynamic qualities including different temperature optima. Kishore et al. (*Biophys. Chem.* 73: 265–280 (1998), the contents of which is incorporated herein by reference in its entirety). Likewise, the forward and backward reactions of a single chemical or biochemical reaction may have different temperature optima. The present invention provides a device and processes for controlling the rates at which different reactions produce different products, or the rates at which forward and backward reactions proceed, by exposing samples in continuous flow to at least two temperatures.

Thermal "tuning" of chemical reactions in accordance with the present invention can be used to drive reactions in a certain direction. Sigbesma et al. (*Science* 278: 1601–1604 (1997), the contents of which is incorporated herein by reference in its entirety) disclose various aspects of the polymerization of 2-ureido-4-pyrimidone, where the thermal and environmental control of bond lifetime and bond strength makes many properties of the reaction, such as viscosity, chain length and composition, tunable in a way that is not accessible to traditional polymers. In one embodiment, a 0.04M solution of a bifunctional derivative of 2-ureido-4-pyrimidone in $CHCl_3$ is introduced into at least one channel 108 via feed basin 102. The sample moves through a temperature regulated zone and a small amount of chain stopper compound is added via reagent reservoir 122*a*. The sample then moves into a temperature regulated zone having a different temperature. Enough chain stopper compound is then added via reagent reservoir 122*b* to stop any further polymerization. When the sample elutes into the outlet basin 104, the sample is then analyzed to determine the degree of polymerization achieved at each temperature. In another embodiment, a mixture of a bifunctional methyl derivative of 2-ureido-4-pyrimidone and a bifunctional methyl-phenyl derivative of 2-ureido-4-pyrimidone in $CHCl_3$, where the two compounds have a 1000-fold difference in viscosity at 30° C., is introduced via feed basin 102. The sample moves in a channel 108 into a temperature regulated zone, and an aliquot of the mixture is removed through the opening for reservoir 122*a*, to measure viscosity and polymer formation. The sample moves into a plurality of temperature regulated zones having different temperature, and aliquots are removed through the opening for reagent reservoirs 122*b*, 122*c*, and so on, to measure viscosity and polymerization of the mixture at each temperature. The sample is then collected via outlet basin 104 and further analyzed.

Additionally, the microfluidic device can also be used generally for the synthesis of chemicals, particularly fine chemicals (ie produced in small volumes and/or of especially high quality. Furthermore, a microfluidic susbtrate or device according to the invention may be provided which includes more than one protocol, such synthesis of fine chemicals in combination with on-line screening (eg drug screening). Chemical synthesis may involve at least one temperature change for carrying out a particular reaction, which can be carried out in a temperature regulated zone according to the invention. Reactants are added introduced to the channel through a main inlet basin and/or one or more reagent basins or reservoirs as needed. The format, including but not limited to choice of substrate material, of the microfluidic device according to the invention are chosen such that they are compatible with the characteristics of the reaction to be carried out, such as reaction temperatures and solvent (eg. water, organic solvents) used in synthesis. Most preferably, reactions are carried out at between −5° C. and 150° C.

In one example, it is known that temperature changes can induce changes in the phosphorylation state of a protein. Heat treatment induces reversible dephosphorylation of retino-blastoma gene product (pRb), which affects the ability of pRb to inhibit SV40-induced DNA synthesis and bind T antigen. Khandjian (*Oncogene* 10: 359–367 (1995), the contents of which is incorporated herein by reference in its entirety). Exposure to 42.5° C. leads to the gradual disappearance of phosphorylated forms of pRB, and this dephosphorylation of pRb correlates with inhibition of SV40-induced DNA synthesis. In one embodiment, a sample containing 1 $\mu$g of pRb is introduced into a plurality of channels 108 via feed basin 102 and enters a temperature regulated zone at 42.5° C. In one set of channels, reagents for phosphorylation are added via reagent reservoir 122*a*; in a separate set of channels that contain the same initial sample and flow in parallel with the first, all the phosphorylation reagents are added except ATP via a separate reagent reservoir 122a'. All the samples move in parallel into a temperature regulated zone of 25° C. for 5 minutes. Samples are then collected from each channel 108 and the phosphorylation state of pRb is determined. Because the thermal effect on the phosphorylation state of pRb is reversible, the present invention provides a device and processes by which a pRb-mediated processes can be regulated by exposing a pRb-containing sample to thermal cycles.

The present invention may also be used in protocols in which it is desirable to regulate the association of macromolecular structures. For example, it is well known that liposome association is temperature-dependent, and this temperature dependence can be modified by addition of thermosensitive polymers. Hayashi et al. (*Bioconjugate Chem*. 9: 382–389 (1998), the contents of which is incorporated herein by reference in its entirety). The present invention provides a device and processes by which the association state of liposomes in a sample can be regulated by thermal cycling. Effects of thermosensitive polymers on liposome association may be measured by taking aliquots from each channel 108 of a sample containing liposomes and polymers. via the opening for reagent reservoirs 122a, 122b, 122c, and so on, following various steps of a temperature cycle. In another embodiment, sample containing liposomes in introduced into a plurality of channels 108 via feed basin 102, and thermosensitive polymers are added latter via reagent reservoir 122a, such that the effects of thermosensitive polymers can be studied by adding the thermopolymers at a later stage to a liposome sample that is undergoing thermal cycling in the device of the present invention.

The present invention further provide a device and processes for carrying out any biological process that utilizes at least one thermal cycle and continuous sample flow. A bacterial culture, a yeast culture, or a culture of suspended plant, insect, mammalian or other cultured cells can be introduced into at least one channel 108 of the device, via the feed basin. The biological sample in channel 108 may be subjected to at least one thermal cycle, and responses to the thermal cycle can be measured. Responses that could be measured include, but are not limited to, production of heat shock proteins, production of proteins that are indicative of stress in each cell system, initiation or inhibition of fission, budding or cell division, excretion of products into the medium, changes in membrane lipid composition, changes in cell wall composition. A biological sample may be subjected to one thermal cycle as it moves by continuous flow through the device, or may be subjected to numerous cycles. A method for thermally "pulsing" a biological sample could be carried out: for example, a sample comprising living cells may be exposed to 40 thermal cycles could be programmed to include, at a later point in the cycle, a brief exposure to temperatures that would normally be lethal to the cell, in order to test whether thermal conditioning of a cell can induce tolerance to higher temperatures. Thermal cycles can likewise be used to study the interaction between temperature and other environmental variables such as ionic strength and composition of the extracellular medium in determining the tolerance of a biological sample to environmental conditions.

In one representative embodiment, a living culture of *E. coli* is introduced into a plurality of channels 108 via feed basin 102. The sample moving in channel 108 is exposed to 10 cycles of 20° C. for 5 minutes, followed by 40° C. for 30 sec, followed by 25° C. for 15 minutes. An aliquot of the sample is removed following 10 cycles, via the opening for reagent reservoir 122a. After aliquots are removed, the salt concentration of the solution is increased by added NaCl solution via reagent reservoir 122a. The sample is then exposed to an additional 10 cycles as described previously. Samples are then collected via outlet basin 104 and the protein profiles of heat-shocked bacterial cells at physiological and elevated salt concentrations is compared.

EXAMPLES

Example 1

PCR Reaction in a Continuous Flow in a Microfluidic Device

A PCR reaction mixture was run through a channel in which a PCR was performed.

The microfluidic substrate comprised 10 channels in parallel chemically etched in silicone. The channels were rectilinear with a diameter of the order of about 600 $\mu$m in the reaction zones. The surface area of the section of a channel was of the order of about 0.25 mm$^2$.

The PCR was carried out in parallel in 3 channels. The volume of one PCR reaction was 1.2 $\mu$l, but ten identical PCR reactions (12 $\mu$l (10×1.2 $\mu$l)) were performed for out of the device post PCR sample analysis (quantification and size analysis).

The microfluidic substrate was siliconized just before the substrate was used. Before the PCR reaction, all the channels were filled with previously degassed and filtered water. A high flow rate of the order of 25 $\mu$l/min was applied for 15 minutes to remove all the air bubbles present in the circuits. A previously degassed and filtered solution of 10 mM Tris-HCl and 50 mM KCl pH 8.3 was then injected at a flow rate of 5 $\mu$l/min for 15 min, taking care not to form air bubbles.

Each DNA sample was diluted in a previously degassed and filtered 1 mM Tris-HCl, 0.1 mM EDTA pH 8.3 buffer, to obtain 10 $\mu$l of a final solution at 2 ng/$\mu$l in DNA. Each PCR reaction used 0.6 $\mu$l of this solution. This solution was placed in the device for injecting the samples in parallel and in series.

One pair of PCR primers was used and total of 30 $\mu$l of a solution was prepared and degassed just prior use: 0.6 $\mu$M of each unpurified PCR primer (Genset), 20 mM Tris-HCl and 100 mM KCl, pH 8.3, 4 mM MgCl$_2$, 0.2 mM of each dNTP (dATP, dCTP, dGTP, dTTP) and 4 U of Taq Gold. Each PCR reaction used 0.6 $\mu$l of this solution. These solutions were placed in the device for injecting the PCR primers in series and were stored at 4° C.

The flow rates in the substrate was 8.2 $\mu$l/hour, which made it possible to achieve ~35 cycles on a 2 cm of the PCR temparature regulated cycling zone.

The PCR reaction mixture was passed just prior the PCR cycling through a temparature regulated zone at 94° C. for 10 minutes to activate the polymerase. It then ran through a temparature cycling zone consisting of a step of 20 sec. at 94° C., then 20 sec. at 55° C. and 20 sec. at 72° C., for a duration corresponding to 35 cycles.

After the PCR was completed, the 10 identical PCR reactions from a given channel were mixed with each other and analyzed by fluorescence quantification and gel electrophoresis, off line (PCR reaction of 1.2 $\mu$l can not be analysed with standard methods). The flourescent quantification of the PCR (with picogreen (Molecular Probes) intercalating dye) showed 75% yield as compared to a positive control performed in a microtiter plate on a commercial thermal cycler (MJ Research). Results from an agarose slab-gel electrophoresis confirmed the specificity of the PCR reaction performed in the microfluidic device (size of the amplified fragment was 500 bp as expected).

Example 2

Integration of a Genotyping Protocol in a Continuous Flow Microfluidic Device

In one embodiment, the reaction mixture runs through a channel in which all the steps required for a genotyping protocol are performed: PCR, purification, microsequencing reaction and detection.

The microfluidic substrate comprises 100 channels in parallel. These channels are rectilinear and have a diameter of the order of 600 μm in the reaction zones. The surface area of the section of a channel is of the order of 0.25 $mm^2$.

The genotyping protocol is carried out in parallel in the 100 channels. 100 samples are injected in parallel into the channels, and 100 such injections of sample are carried out sequentially, so that each channel contains 100 injections of the same sample. The microfluidic substrate thus makes it possible, by means of a cross-distribution of 100 samples for 100 polymorphisms, to carry out 10,000 genotyping reactions on a microfluidic substrate.

The injection of the reagents is performed into different points of the channel; it is synchronized in a such a way as to be able to carry out the reactions in series, in parallel and in continuous flow.

To avoid any contamination, a given channel is fed in series with the same DNA. However, this DNA is analysed for 100 different polymorphisms.

The microfluidic substrate is siliconized according to the protocol described by Schoffner et al. (*Nucleic Acid Research*, Vol. 24, No. 2, p. 375–379 (1996), the disclosure of which is incorporated herein by reference in its entirety). The siliconized substrates can be stored as they are for several months. The substrate siliconization step can be carried out during the manufacture of the substrate. Before using the substrate, all the channels are filled with previously degassed and filtered water. A high flow rate of the order of 25 μl/min is applied for 15 minutes to remove all the air bubbles present in the circuits. A previously degassed and filtered solution of 10 mM Tris-HCl and 50 mM KCl pH 8.3 is then injected at a flow rate of 5 μl/min for 15 min, taking great care not to form air bubbles. This operation preferably takes place on a external apparatus which is able to treat several substrates in parallel.

Each DNA sample is diluted in a previously degassed and filtered 1 mM Tris-HCl, 0.1 mM EDTA pH 8.3 buffer, to obtain 30 μl of a final solution at 2 ng/μl in DNA. One DNA preparation per channel is required. Each genotyping reaction uses 0.25 μl of this solution; 30 μl corresponds to the amount required to carry out 100 successive genotypings on the same individual plus dead volume of the injection device. This solution is placed in the injection device for parallel injections.

For every polymorphic site a PCR reaction must be prepared and degassed just prior use (100 different PCR reaction mix). For each PCR rection mix, 30 μl of a solution must be prepared: 0.6 μM of each unpurified PCR primer (Genset), 20 mM Tris-HCl and 100 mM KCl pH 8.3, 4 mM $MgCl_2$, 0.2 mM of each dNTP (dATP, dCTP, dGTP, dTTP) and 2 U of Taq Gold. Each genotyping reaction uses 0.25 μl of this solution for a final reaction volume of 0.5 μl; 30 μl correspond to the amount required to carry out 100 genotypings in parallel on 100 different channels plus the dead volume of the injection device. These solutions are placed in the device for injecting the PCR primers in series, and are stored at 4° C.

The PCR purification reaction mixture is common to all genotyping reactions. A 5500 μl volume of a solution: 20 mM Tris-HCl pH 8.0, 10 mM $MgCl_2$, previously degassed and filtered, 550 U of shrimp alkaline phosphatase (SAP) and 550 U of exonuclease I, is prepared and stored at 4° C. in the injection device for the PCR purification reaction mixture. Each genotyping reaction uses 0.5 μl of this solution for a final reaction volume of 1 μl. 5500 μl correspond to the amount required to carry out 10,000 genotypings in parallel plus dead volume of the injection device.

One preparation per site to be genotyped is required (100 different microsequencing solution). For each microsequencing oligonucleotide, 120 μl of a microsequencing solution must be prepared and degased prior use: 1 μM of crude microsequencing oligonucleotide (Genset), 40 mM Tris-HCl pH 9.5, 8 mM $MgCl_2$, 10 nM of a ddNTP-Tamra and 10 nM of a ddNTP-Fam, each ddNTP corresponding to one allele of the site, and 6 U of thermosequenase. Each genotyping reaction uses 1 μl of this solution for a final reaction volume of 2 μl; 120 μl correspond to the amount required to carry out 100 genotypings in parallel on 100 different channels and the dead volume of the serial injection device. These microsequencing solutions are placed in the device for injecting the microsequencing primers in series, and are stored at 4° C.

The flow rates at the substrate outlet are 40 μl/hour. For reactions volumes of 2 μl separated by 2 μl separators, the overall reaction yield per channel is of 10 reactions/hour. The separating separators consist of liquid which is non-miscible with the reaction media, such as liquid petroleum jelly for example. They physically separate the reactions from each other all along the reaction course through the channel.

The DNA sample is distributed in a volume of 0.25 μl per genotyping reaction. It is injected with a flow rate of 5 μl/hour, which represents a time of 3 minutes and a length of 1 mm. Each sample injection is separated by 0.25 μl of non-miscible separator.

0.25 μl of PCR reagent are injected with a flow rate of 5 μl/hour and are mixed with the DNA samples. Each PCR reagent injection is separated by the injection of 0.25 μl of non-miscible separator. The PCR reaction thus represents a volume of 0.5 μl and a length in the channel of 2 mm, and moves with a flow rate of 10 μl/hour.

This reaction mixture runs through a zone which can be cycled, in which a cycle consists of a step of 20 sec. at 94° C., then 20 sec. at 55° C. and 20 sec. at 72° C., for a duration corresponding to 35 cycles.

After the PCR, 0.5 μl of PCR purification reagent is injected with a flow rate of 10 μl/hour. Each reagent injection is separated by the injection of 0.5 μl of separator. The PCR purification reaction thus represents a volume of 1 μl and a length in the channel of 4 mm, and moves with a flow rate of 20 μl/hour.

This reaction mixture then runs through a temperature regulated zone at 37° C. for 20 minutes for the purification reaction, then a temperature regulated zone at 94° C. for 10 minutes for the inactivation of the purification enzymes (SAP and EXO I).

Next, 1 μl of microsequencing reagent is injected with a flow rate of 20 μl/hour. Each microsequencing reagent injection is separated by the injection of 1 μl of non-miscible separator. The microsequencing reaction thus represents a volume of 2 µl and a length in the channel of 8 mm, and moves with a flow rate of 40 µl/hour. The microsequencing reagent must be injected with the right PCR amplified fragment, a good synchronisation between injection is therefore required.

This microsequencing reaction mixture (2 µl) runs through a zone which can be cycled, in which a cycle consists of a step of 10 sec. at 94° C., then 10 sec. at 55° C. and 10 sec. at 72° C., for a duration corresponding to 25 cycles.

The detection is carried out on line and continuously, after the microsequencing zone.

The detection is carried out by measuring the polarized fluorescence for the fluorophores Fam and Tamra. The excitation wavelengths are respectively 488 nm and 555 nm, while the emission wavelengths are respectively 520 nm and 575 nm. Two fluorescence measurements are carried out simultaneously, one in the plane of polarization of the excitation beam and the other in the plane which is perpendicular to this plane. The ratio of these two measurements makes it possible to differentiate the presence of a labelled oligonucleotide (microsequencing oligonucleotide lengthened during the reaction) from two to five times more free labels (fluorescent ddNTPs).

Example 3

Genotyping by the Method of Allele-Specific Ligase Chain Reaction (LCR)

Allele-specific LCR, as disclosed in Barany et al. (*PCR Meth. Appl.* 1: 5–16 (1991), the contents of which are incorporated herein by reference in its entirety), employs four oligonucleotides two of which hybridize to one strand of target DNA and a complementary set of adjacent oligonucleotides, which hybridize to the opposite strand. Thermostable DNA ligase will covalently link each set, provided there is complete complementarity at the junction. A single-base mismatch at the oligonucleotide junction will not be amplified and is therefore distinguished; a second set of mutant-specific olgionucleotides is used in a separate reaction to detect or confirm the mutant allele(s).

A homogeneous phase protocol for allele-specific LCR can be carried out in accordance with the present invention by introducing into each channel 10 µl of starting mixture comprising: the DNA with the target sequence to be analyzed; 40 femtomoles each of four complementary oligonucleotide primers; 15 nick-closing units of thermostable ligase such as that from *Thermus thermophilus*; at least 1 µM of each of dATP, dGTP, dCTP, dTTP; 4 µg carrier salmon sperm DNA; in a buffer solution of 20 mM Tris-HCl, 100 mM KCl, 10 mM $MgCl_2$, 10 mM DTT, 10 mM NAD+, 1 mM EDTA, at pH 7.6. In a first step of a cycle, the DNA is heat-denatured at 94° C. for 1 min. In a next step carried out at 65° C. for 4 min, the four complementary oligonucleotides will anneal to the target DNA at a temperature near their melting point, and thermostable ligase will ligate those oligonucleotides having a perfect. The reaction cycle is carried out 20 to 30 times by using continuous flow to move the reaction mixture through channels in a temperature regulated zone which has been programmed to cycle between 94° C. and 65° C. Parallel reactions utilizing a separate set of oligonucleotides specific for different alleles may be carried out in parallel, such that the same target DNA, enzyme, buffer, and nucleotides are introduced into each channel and different sets of allele-specific oligonucleotides are introduced simultaneously into individual channels; alternately, allele-specific reactions may be carried out sequentially in the same channel, using "separator" to separate one reaction from another.

Example 4

Identifying New Polymorphisms using Arbitrarily Primed PCR (AP-PCR)

The method of arbitrarily primed PCR (AP-PCR) is often useful as a preliminary step to find potential polymorphisms. Jonas et al. (*J. Clin. Microbiol.* 38: 2284–2291 (2000), the contents of which is incorporated herein by reference in its entirety). AP-PCR can be carried out as follows: a reaction volume of 2.5 µl comprising 0.1 µl of cell lysate; 10 mM HCl, 3 mM $MgCl_2$, 50 mM KCl, 0.2 mM dNTPs, 1 units Taq DNA polymerase, with M13 primer fluorescently labelled with Cy-5, at pH 9.0. In one embodiment, the reaction mixture is made prior to introducing it into a channel of the present invention; in another embodiment, components of the reaction mixture are introduced directly into the device. Continuously flowing through temperature regulated zones, the reaction mixture is exposed to 45 cycles of 95° C. for 60 s, 36° C. for 60 s, and 72° C. for 120 s. Reaction products may be sequenced to identify polymorphisms in situ in the device as described above, or alternately, removed for analysis.

Example 5

Genotyping by the TaqMan™ PCR Method

A homogeneous phase protocol for TaqMan™ PCR can be carried out in accordance with the present invention using a microfluidic substrate essentially as described in Example 2.

TaqMan™ is carried out in parallel in several (for example 3) channels. The volume of one PCR reaction is 0.6 µl. Alternatively, the product of a single PCR reaction is detected.

The microfluidic substrate is siliconized just before the substrate is used. Before using the substrate, all the channels are filled with previously degassed and filtered water. A high flow rate of the order of 25 µl/min is applied for 15 minutes to remove all the air bubbles present in the circuits. A previously degassed and filtered solution of 10 mM Tris-HCl and 50 mM KCl pH 8.3 is then injected at a flow rate of 5 µl/min for 15 min, taking care not to form air bubbles.

Each DNA sample is diluted in a previously degassed and filtered 1 mM Tris-HCl, 0.1 mM EDTA pH 8.3 buffer, to obtain 30 µl of a final solution at 2 ng/µl in DNA (enough to perform 50 different molecular beacon gentyping reactions with the same sample). One DNA preparation is used for all three channels. Each PCR reaction uses 0.6 µl of this solution. This solution is placed in a device for injecting the samples in parallel and in series.

A TaqMan™ PCR reagent mixture comprising one pair of PCR primers and two allele specific molecular probes (one for each allele of the target nucleotide) labelled with a reporter and quencher dye is used, and total of 6 µl of a solution is prepared: 0.6 µM of each unpurified PCR primer, 20 mM Tris-HCl and 100 mM KCl pH 8.3 (or TaqMan buffer A, PE Applied Biosystems), previously degassed and filtered, 4 mM $MgCl_2$, 0.2 mM of custom labelled probe and of each dNTP (dATP, dCTP, dGTP, dTTP), and 0.5 U of AmpliTaq Gold. Each PCR reaction used 0.6 µl of this solution. These solutions were placed in the device for injecting the PCR primers in series; and were stored at 4° C. Up to 50 different reaction mix corresponding to 50 different polymorphic sites, can be prepared by changing the PCR primers probes and TaqMan probes. Care will be taken to have PCR products with equivalent size and TaqMan probes with similar Tms in order to keep the same cycling temperatures for all the different reactions. The different reaction mix are injected one after the other in the device, however when injected the mix is injected in all the channels in parallel.

The flow rates in the substrate is 8.2 µl/hour, such that ~35 cycles are carried out on 2 cm of the PCR temperature regulated cycling zone.

This reaction mixture can be treated before injection into a device at 94° C. for 10 minutes if necessary to activate the polymerase. It is run through a zone which is cycled, in which a cycle consists of a step of 20 sec. at 94° C., then 20 sec. at 55° C. and 20 sec. at 72° C., for a duration corresponding to 35 cycles.

Once the PCR reaction flows out of the PCR temperature regulated zone, the PCR is completed, the reaction can then pass a thermostated detection zone consisting of a fluorimeter adapted to the TaqMan probes wave length and continuous flow detection. In an other embodiment the PCR reactions can be collected from the oulet basin and analyzed on an ABI Prism 7700 Sequence Detection System according to the manufacturers instructions.

Example 6

Genotyping using Molecular Beacons

A homogeneous phase protocol using molecular beacons can be carried out in accordance with the present invention using a microfluidic substrate essentially as described in Example 2.

The assay is carried out in parallel in several (for example 3) channels. The volume of one PCR reaction is 1.2 µl. Alternatively, the product of a single PCR reaction is detected.

The microfluidic substrate is siliconized just before the substrate is used. Before using the substrate, all the channels are filled with previously degassed and filtered water. A high flow rate of the order of 25 µl/min is applied for 15 minutes to remove all the air bubbles present in the circuits. A previously degassed and filtered solution of 10 mM Tris-HCl and 50 mM KCl pH 8.3 is then injected at a flow rate of 5 µl/min for 15 min, taking care not to form air bubbles.

Each DNA sample is diluted in a previously degassed and filtered 1 mM Tris-HCl, 0.1 mM EDTA pH 8.3 buffer, to obtain 30 µl of a final solution at 2 ng/µl in DNA (enough to perform 50 different molecular beacon gentyping reactions with the same sample). One DNA preparation is used for all three channels. Each PCR reaction uses 0.6 µl of this solution. This solution is placed in a device for injecting the samples in parallel and in series.

A PCR reagent mixture comprising one pair of PCR primers and two allele specific molecular beacon probes (one for each allele of the target nucleotide) labelled with a reporter (FAM) and quencher dye (TAMRA) is used, and a total of 6 µl of a solution is prepared: 0.6 µM of each unpurified PCR primer, 20 mM Tris-HCl and 100 mM KCl pH 8.3 previously degassed and filtered, 4 mM $MgCl_2$, 0.2 mM of molecular beacon probe and of each dNTP (dATP, dCTP, dGTP, dTTP), and 0.5 U of AmpliTaq Gold. Each PCR reaction used 0.6 µl of this solution. These solutions were placed in the device for injecting the PCR primers in series; and were stored at 4° C. Up to 50 different reaction mix corresponding to 50 different polymorphic sites, can be prepared by changing the PCR primers probes and molecular beacons probes. Preferably, the PCR products have equivalent sizes and the molecular beacon probes have similar Tms in order to keep the same cycling temperatures for all the different reactions. The different reaction mix are injected one after the other in the device, however when injected the mix is injected in all the channels in parallel.

The flow rates in the substrate is 8.2 µl/hour, such that 35 cycles are carried out on 2 cm of the PCR PCR temperature regulated cycling zone.

This reaction mixture can be treated before injection into a device at 94° C. for 10 minutes if necessary to activate the polymerase. It is run through a zone which is cycled, in which a cycle consists of a step of 20 sec. at 94° C., then 20 sec. at 55° C. and 20 sec. at 72° C., for a duration corresponding to 35 cycles.

Once the PCR reaction flows out of the PCR temperature regulated zone, the PCR is completed, the reaction can then pass a thermostated detection zone consisting of a fluorimeter adapted to the molecular beacon wave length and continuous flow detection. In an other embodiment the PCR reactions can be collected from the oulet basin and analyzed on an ABI Prism 7700 Sequence Detection System according to the manufacturers instructions.

Although this invention has been described in terms of certain preferred embodiments, other embodiments which will be apparent to those of ordinary skill in the art in view of the disclosure herein are also within the scope of this invention. Accordingly, the scope of the invention is intended to be defined only by reference to the appended claims. All documents cited herein are incorporated herein by reference in their entirety.

What is claimed is:

1. A device comprising:
  a microfluidic substrate comprising at least one sample pathway for sample flow; and
  said microfluidic substrate further comprising at least one temperature regulated zone that cycles between at least two different and predetermined temperatures, said at least one temperature regulated zone being adapted to bring at least a portion of said sample pathway to said at least two temperatures while a sample is unidirectionally flowing along said at least a portion of said sample pathway and said at least one temperature regulated zone comprising a metal bar in fluid communication with a plurality of water sources containing water at said at least two temperatures, said metal bar being in thermal communication with said at least a portion of said sample pathway and wherein a sample is cycled between said at least two different and predetermined temperatures while in said at least one temperature regulated zone.

2. The device of claim 1, further comprising a force supplying member operably linked to said at least one pathway for sample flow wherein said force supplying member applies a force to said sample such that said sample travels along said at least one pathway.

3. The device of claim 1, wherein said microfluidic substrate consists essentially of silicon.

4. The device of claim 1, further comprising a detector for measuring a physicochemical property of a biological sample.

5. The device of claim 1, wherein said device comprises a microfluidic substrate comprising at least one temperature regulated zone which is capable of cycling between at least two temperatures, and at least one constant temperature zone.

6. The device of claim 1, wherein said device comprises a microfluidic substrate comprising several temperature regulated zones capable of cycling between at least two temperatures.

7. The device of claim 1, wherein said flowing sample goes through a plurality of temperature cycles as it travels through the temperature regulated zone.

8. The device of claim 1, wherein said device comprises one temperature regulated zone.

9. The device of claim 1, wherein said device further comprises at least one thermostatting means that cycles said temperature regulated zone between said at least two different and predetermined temperatures.

10. The device of claim 1, wherein said at least one temperature regulated zone cycles between −5° C. and 150° C.

11. The device of claim 1, wherein said at least one temperature regulated zone cycles between 20° C. and 40° C.

12. The device of claim 1, wherein said at least one temperature regulated zone cycles between 57° C., 72° C., and 94° C.

13. The device of claim 1, wherein said at least one temperature regulated zone cycles between 37° C. and 94° C.

14. The device of claim 1, wherein said at least one temperature regulated zone cycles between 55° C. and 94° C.

15. The device of claim 1, wherein said at least one temperature regulated zone cycles between 65° C. and 94° C.

16. The device of claim 1, wherein said at least one of temperature regulated zone cycles at 25° C. and 42.5° C.

17. The device of claim 1, wherein said device further comprises temperature sensors in each temperature regulated zone.

18. The device of claim 17, wherein said temperature sensors are two thermocouples and a platinum sensor.

19. The device of claim 2, wherein the force generated by said force supplying member is pressure.

20. The device of claim 19, further comprising a sample supplier which supplies a sample to said at least one pathway.

21. The device of claim 20, further comprising at least one inlet basin positioned at a first end of said at least one pathway such that said sample supplier supplies said sample to said inlet basin and said sample travels from said inlet basin to said at least one pathway.

22. The device of claim 21, further comprising at least one outlet basin positioned at a second end of said pathway.

23. The device of claim 22, further comprising at least one reagent supplier positioned between said inlet basin and said outlet basin.

24. The device of claim 23, wherein said device comprises a plurality of said pathways.

25. The device of claim 24, wherein said pathways comprise channels arranged in parallel, and wherein said channels are fed in series with different samples separated from each other by separators.

26. The device of claim 25 wherein the portion of the channel which crosses the temperature regulated zone is rectilinear.

27. The device of claim 19, wherein said microfluidic substrate consists essentially of silicon.

28. The device of claim 19, further comprising a detector for measuring a physicochemical property of a biological sample.

29. The device of claim 19, wherein said device comprises a microfluidic substrate comprising at least one temperature regulated zone which is capable of cycling between at least two temperatures, and at least one constant temperature zone.

30. The device of claim 19, wherein said device comprises a microfluidic substrate comprising more than one temperature regulated zone capable of cycling between at least two temperatures.

31. The device of claim 19, wherein said flowing sample goes through a plurality of temperature cycles as it travels through the temperature regulated zone.

32. The device of claim 2, further comprising a sample supplier which supplies a sample to said at least one pathway.

33. The device of claim 32, further comprising at least one inlet basin positioned at a first end of said at least one pathway such that said sample supplier supplies said sample to said inlet basin and said sample travels from said inlet basin to said at least one pathway.

34. The device of claim 33, further comprising at least one outlet basin positioned at a second end of said pathway.

35. The device of claim 34, further comprising at least one reagent supplier positioned between said inlet basin and said outlet basin.

36. The device of claim 35, wherein said device comprises a plurality of said pathways.

37. The device of claim 36, wherein said pathways comprise channels arranged in parallel.

38. The device of claim 37, wherein the force generated by said force supplying member is pressure.

39. The device of claim 37, wherein said channels are fed in series with different samples separated from each other by separators.

40. The device of claim 37 wherein the portion of the channel which crosses the temperature regulated zone is rectilinear.

* * * * *

UNITED STATES PATENT AND TRADEMARK OFFICE
CERTIFICATE OF CORRECTION

PATENT NO. : 7,015,030 B1  
APPLICATION NO. : 09/627647  
DATED : March 21, 2006  
INVENTOR(S) : Yves Fouillet et al.

Page 1 of 1

It is certified that error appears in the above-identified patent and that said Letters Patent is hereby corrected as shown below:

<u>Column 23,</u>
Line 38, "Clin Microbiol" should read -- J Clin Microbiol --.
Lines 41 and 45, "Clin Microbiol" should read -- J Clin Microbiol --.

<u>Column 42,</u>
Line 63, "enzymes-occurs." should read -- enzymes occurs. --.

<u>Column 54,</u>
Line 10, "that 35" should read -- that ~35 --.

Signed and Sealed this

Twenty-seventh Day of June, 2006

JON W. DUDAS
*Director of the United States Patent and Trademark Office*